US012408913B2

(12) United States Patent
Phillips et al.

(10) Patent No.: US 12,408,913 B2
(45) Date of Patent: Sep. 9, 2025

(54) MAGNETIC SUTURE LOOP COMPRISING A SUTURE MAGNET, A BIFURCATED SUTURE, AND A CARTRIDGE TUBE

(71) Applicant: APPLIED MEDICAL TECHNOLOGY, INC., Brecksville, OH (US)

(72) Inventors: Grant Wesley Phillips, Richfield, OH (US); Steven Alfred Soeder, North Royalton, OH (US); George J. Picha, Brecksville, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 12 days.

(21) Appl. No.: 18/501,145

(22) Filed: Nov. 3, 2023

(65) Prior Publication Data

US 2024/0057998 A1   Feb. 22, 2024

Related U.S. Application Data

(63) Continuation of application No. 17/995,779, filed as application No. PCT/US2022/029627 on May 17, 2022, now Pat. No. 11,839,373.

(Continued)

(51) Int. Cl.
*A61B 17/062* (2006.01)
*A61B 17/04* (2006.01)
(Continued)

(52) U.S. Cl.
CPC .... *A61B 17/06166* (2013.01); *A61B 17/0469* (2013.01); *A61B 17/06004* (2013.01);
(Continued)

(58) Field of Classification Search
CPC ............ A61B 17/0469; A61B 17/0482; A61B 17/0485; A61B 17/06166; A61B 17/062;
(Continued)

(56) References Cited

U.S. PATENT DOCUMENTS

| 1,212,870 A | 1/1917 | Zolper |
|---|---|---|
| 3,762,418 A | 10/1973 | Wasson |

(Continued)

FOREIGN PATENT DOCUMENTS

| EP | 778004 B1 | 3/2003 |
|---|---|---|
| JP | 2006-25932 A | 2/2006 |

(Continued)

OTHER PUBLICATIONS

Owens, J., "How Does a Clicky Pen Work?" You Tube, pp. 1-8 (2022), available at https://www.youtube.com/watch?v=Zv5Qa2kGL04, last accessed Sep. 29, 2022.

(Continued)

*Primary Examiner* — Tuan V Nguyen
(74) *Attorney, Agent, or Firm* — EVENTIDE LAW LLC

(57) ABSTRACT

A magnetic suture loop comprising a suture magnet, a bifurcated suture, and a cartridge tube is disclosed. The bifurcated suture extends from the suture magnet and forms a suture loop. The cartridge tube comprises a cartridge tube proximal end, a cartridge tube distal end, and a cartridge tube wall extending therebetween. The cartridge tube has a cartridge tube proximal opening at the cartridge tube proximal end, a cartridge tube distal opening at the cartridge tube distal end, and a cartridge tube lumen extending from the cartridge tube proximal opening to the cartridge tube distal opening. The suture loop traverses the cartridge tube lumen based on having been inserted through the cartridge tube (Continued)

distal opening. The suture magnet is disposed outside of the cartridge tube lumen adjacent the cartridge tube distal opening.

11 Claims, 27 Drawing Sheets

Related U.S. Application Data

(60) Provisional application No. 63/268,596, filed on Feb. 25, 2022, provisional application No. 63/189,511, filed on May 17, 2021.

(51) Int. Cl.
  *A61B 17/06* (2006.01)
  *A61B 17/00* (2006.01)

(52) U.S. Cl.
  CPC ........... *A61B 2017/00349* (2013.01); *A61B 2017/00867* (2013.01); *A61B 2017/00876* (2013.01)

(58) Field of Classification Search
  CPC ...... A61B 17/0625; A61B 2017/06004; A61B 2017/00867; A61B 2017/00349; A61B 2017/047
  USPC ....... 606/139, 144, 145, 146, 147, 148, 149, 606/150
  See application file for complete search history.

(56) References Cited

U.S. PATENT DOCUMENTS

| | | | |
|---|---|---|---|
| 4,115,015 A | 9/1978 | Torii |
| 4,266,881 A | 5/1981 | Rubens |
| 4,540,300 A | 9/1985 | Midorikawa |
| 4,560,298 A | 12/1985 | Oki et al. |
| D292,297 S | 10/1987 | Bingham |
| 4,711,592 A | 12/1987 | Gregory |
| 4,759,650 A | 7/1988 | Granoff |
| 4,969,764 A | 11/1990 | Gregory |
| 4,986,682 A | 1/1991 | Lu |
| 5,022,773 A | 6/1991 | Waldinger et al. |
| 5,026,190 A | 6/1991 | Longarzo |
| D321,207 S | 10/1991 | Granoff |
| D321,718 S | 11/1991 | Ambasz |
| 5,131,775 A | 7/1992 | Chen |
| 5,152,626 A | 10/1992 | Eppler |
| 5,174,814 A | 12/1992 | Burwell et al. |
| 5,364,365 A | 11/1994 | Wortrich |
| 5,501,692 A | 3/1996 | Riza |
| 5,651,626 A | 7/1997 | Chen |
| 5,653,716 A | 8/1997 | Malo et al. |
| 5,722,981 A | 3/1998 | Stevens |
| 5,756,941 A | 5/1998 | Snell |
| 5,824,009 A | 10/1998 | Fukuda et al. |
| 5,864,490 A | 1/1999 | Van Bost |
| 5,928,250 A | 7/1999 | Koike et al. |
| 5,997,204 A | 12/1999 | Ducrocq |
| 6,159,224 A | 12/2000 | Yoon |
| 6,213,661 B1 | 4/2001 | Coon |
| 6,318,921 B1 | 11/2001 | Craine |
| D457,917 S | 5/2002 | Traut et al. |
| 6,450,721 B1 | 9/2002 | D'Amico et al. |
| 6,547,470 B2 | 4/2003 | Legg |
| 6,551,304 B1 | 4/2003 | Whalen et al. |
| 6,719,765 B2 | 4/2004 | Bonutti |
| D494,218 S | 8/2004 | Anand |
| D495,001 S | 8/2004 | Anand |
| 6,830,402 B2 | 12/2004 | Sunatori |
| 6,981,812 B1 | 1/2006 | Hsieh |
| D537,878 S | 3/2007 | Anand |
| D542,349 S | 5/2007 | Anand |
| 7,226,229 B1 | 6/2007 | Register |
| D548,788 S | 8/2007 | Anand |
| 7,334,954 B1 | 2/2008 | Rentz |
| D571,400 S | 6/2008 | Anand |
| D574,429 S | 8/2008 | Kusaba et al. |
| D591,136 S | 4/2009 | Cheldin |
| D616,497 S | 5/2010 | Shiina |
| 7,887,212 B2 | 2/2011 | Liu |
| 7,948,648 B2 | 5/2011 | Silverbrook et al. |
| 7,969,587 B2 | 6/2011 | Silverbrook |
| 8,031,177 B2 | 10/2011 | Lapstun et al. |
| 8,087,841 B2 | 1/2012 | Liu |
| 8,094,325 B2 | 1/2012 | Silverbrook |
| 8,182,167 B2 | 5/2012 | Liu |
| 8,197,497 B2 * | 6/2012 | Nobles ............... A61B 17/0487 606/232 |
| 8,240,931 B1 | 8/2012 | Collins |
| 8,262,241 B2 | 9/2012 | Liu |
| 8,267,947 B2 | 9/2012 | Pantages et al. |
| 8,287,204 B2 | 10/2012 | Silverbrook et al. |
| 8,297,868 B2 | 10/2012 | Underwood et al. |
| 8,360,669 B2 | 1/2013 | Underwood et al. |
| 8,414,210 B2 | 4/2013 | Silverbrook et al. |
| 8,632,270 B2 | 1/2014 | Liu |
| 8,702,753 B2 | 4/2014 | Mikkaichi et al. |
| D725,112 S | 3/2015 | Bo |
| 9,351,721 B2 | 5/2016 | Auerbach et al. |
| D758,988 S | 6/2016 | An et al. |
| 9,474,572 B2 | 10/2016 | Lowry |
| 9,770,238 B2 | 9/2017 | Bonutti |
| 10,245,021 B2 | 4/2019 | Phillips et al. |
| 10,299,786 B2 | 5/2019 | Levine et al. |
| 10,343,445 B2 | 7/2019 | Wu |
| 10,503,284 B1 | 12/2019 | Chang et al. |
| 10,960,705 B1 | 3/2021 | Yu |
| 10,974,540 B1 | 4/2021 | Yu |
| 11,241,904 B2 | 2/2022 | Yu |
| 11,672,530 B2 | 6/2023 | Williams et al. |
| 11,723,655 B2 | 8/2023 | Phillips et al. |
| 2003/0139752 A1 | 7/2003 | Pasricha et al. |
| 2003/0216613 A1 | 11/2003 | Suzuki et al. |
| 2004/0116963 A1 | 6/2004 | Lattouf |
| 2005/0154403 A1 | 7/2005 | Sauer et al. |
| 2006/0069398 A1 | 3/2006 | Suzuki et al. |
| 2007/0118153 A1 | 5/2007 | Funamura et al. |
| 2008/0154286 A1 | 6/2008 | Abbott et al. |
| 2008/0243148 A1 | 10/2008 | Mikkaichi et al. |
| 2008/0269783 A1 | 10/2008 | Griffith |
| 2009/0224561 A1 | 9/2009 | Jackson, III |
| 2009/0318958 A1 | 12/2009 | Ochiai |
| 2010/0280530 A1 | 11/2010 | Hashiba |
| 2011/0015653 A1 | 1/2011 | Bogart et al. |
| 2011/0112555 A1 | 5/2011 | Overes et al. |
| 2011/0118757 A1 | 5/2011 | Pierce |
| 2011/0144666 A1 | 6/2011 | Egle et al. |
| 2011/0245850 A1 | 10/2011 | van der Burg et al. |
| 2012/0277766 A1 | 11/2012 | Ferree |
| 2013/0074849 A1 | 3/2013 | Rousseau et al. |
| 2013/0317291 A1 | 11/2013 | Yamamoto |
| 2015/0038976 A1 | 2/2015 | Roschak et al. |
| 2015/0039027 A1 | 2/2015 | Broom et al. |
| 2015/0327850 A1 | 11/2015 | Kostrzewski |
| 2016/0324517 A1 | 11/2016 | Liu |
| 2017/0049439 A1 | 2/2017 | Keyser et al. |
| 2018/0049733 A1 | 2/2018 | Zhao et al. |
| 2018/0296201 A1 | 10/2018 | Holsten et al. |
| 2019/0076141 A1 | 3/2019 | Liu |
| 2019/0133591 A1 | 5/2019 | Dobashi et al. |
| 2020/0214695 A1 | 7/2020 | Liu |
| 2020/0360017 A1 | 11/2020 | Liu |
| 2021/0045735 A1 | 2/2021 | Nobles et al. |
| 2021/0059667 A1 | 3/2021 | Williams et al. |
| 2022/0104802 A1 | 4/2022 | Liu |

(56) References Cited

U.S. PATENT DOCUMENTS

| | | | |
|---|---|---|---|
| 2022/0104803 A1 | 4/2022 | Desjardin et al. | |
| 2023/0141192 A1 | 5/2023 | Phillips et al. | |

FOREIGN PATENT DOCUMENTS

| | | | | |
|---|---|---|---|---|
| JP | 2010514467 A | 5/2010 | | |
| WO | WO-0069342 A2 * | 11/2000 | ......... | A61B 17/0469 |
| WO | 2010129312 A2 | 11/2010 | | |
| WO | 2011025767 A1 | 3/2011 | | |
| WO | WO-2017111163 A1 * | 6/2017 | ......... | A61B 17/0057 |

OTHER PUBLICATIONS

Medacta International, "FastShuttle Suture Passer System Product Catalog," pp. 1-8 (2019), available at https://media.medacta.com/media/pc-99116sm180-rev-00.pdf, last accessed Sep. 29, 2022.

Imhoff, J., "Performing Incision-Less Hernia Repair for Kids," Michigan Health, pp. 1-5 (Feb. 17, 2020), available at https://labblog.uofmhealth.org/industry-dx/performing-incision-less-hernia-repairs-for-kids, last accessed Feb. 16, 2022.

Johnson, K.N., et al., "Ultrasound-Guided Pediatric Inguinal Hernia Repair," Journal of Pediatric Surgery, vol. 56, pp. 1240-1245 (epublished Mar. 11, 2021).

Young, R., "Rethinking the Simple Suture Passer," Orthopedics This Week, RRY Publications, pp. 1-8 (Apr. 29, 2016), available at https://ryortho.com/2016/04/rethinking-the-simple-suture-passer/, last accessed Apr. 25, 2022.

OrthoMed, Inc., "Suture Passer with Crochet Hook," pp. 1-2 (2022), available at https://www.orthomedinc.com/surgical-instruments/suture-passer-with-crochet-hook, last accessed Sep. 29, 2022.

Mediflex Surgical Products, "5mm Curved Maryland Dissector with Cross Serrations," pp. 1-4 (2022), available at https://mediflex.com/products/5mm-curved-maryland-dissector, last accessed Sep. 29, 2022.

CooperSurgical, Inc., "Carter-Thomason CloseSure System—Port Site Closure," pp. 1-2 (2022), available at https://www.coopersurgical.com/detail/carter-thomason-closesure-system-port-site-closure/, last accessed Sep. 29, 2022.

Endoscopy Superstore, "Arthro-Pro Suture Manipulator Grasper," Manufacturer: Advanced Endoscopy Devices, pp. 1-2 (2022), available at https://www.endoscopysuperstore.com/arthro-pro-suture-manipulator-grasper.aspx#, last accessed Sep. 29, 2022.

Arthrex, Inc., "Back Grasper with SR Handle," pp. 1-3 (2022), available at https://www.arthrex.io/products/AR-12531SR, last accessed Sep. 29, 2022.

Arthrex, Inc., "CrabClaw," pp. 1-3 (2022), available at https://www.arthrex.com/shoulder/crabclaw, last accessed Sep. 29, 2022.

Smith & Nephew, "Meniscus Mender II," pp. 1-2 (2022), available at https://www.smith-nephew.com/professional/products/all-products/meniscus-mender-ii/, last accessed Sep. 29, 2022.

DePuy Synthes, "Chia Percpasser Suture Passer," pp. 1-5 (2021), available at https://www.jnjmedtech.com/en-US/product/chia-percpasserr-suture-passer, last accessed Sep. 29, 2022.

DePuy Synthes, "Ideal Suture Shuttle," pp. 1-4 (2021), available at https://www.jnjmedtech.com/en-US/product/ideal-suture-shuttle, last accessed Sep. 29, 2022.

Arthrex, Inc., "SutureLasso," pp. 1-5 (2022), available at https://www.arthrex.com/shoulder/suturelassos, last accessed Sep. 29, 2022.

Medtronic, "Endoscopic Suturing Devices," pp. 1-3 (2022), available at https://www.medtronic.com/covidien/en-us/products/hand-instruments-ligation/endoscopic-suturing-devices.html, last accessed Sep. 29, 2022.

Zimmer Biomet, "SpeedSnare Surgical Suture Passer," pp. 1-7 (2022), available at https://www.zimmerbiomet.com/en/products-and-solutions/specialties/sports-medicine/speedsnare-surgical-suture-passer.html, last accessed Sep. 29, 2022.

Wikipedia, "Veress needle," pp. 1-3 (Apr. 3, 2022), available at https://en.wikipedia.org/wiki/Veress_needle, last accessed Sep. 29, 2022.

CooperSurgical, Inc., "Carter-Thomason II Port Site Closure System," pp. 1-2 (2022), available at https://www.coopersurgical.com/detail/carter-thomason-ii-port-site-closure-system/, last accessed Sep. 29, 2022.

Mediflex Surgical Products, "SafePass Suture Grasper," pp. 1-4 (2022), available at https://mediflex.com/products/safepass%E2%84%A2-suture-grasper-box-of-10-sterile, last accessed Sep. 29, 2022.

Zimmer Biomet, "Dragon Tongue Suture Passer," pp. 1-5 (2022), available at https://www.zimmerbiomet.com/en/products-and-solutions/specialties/sports-medicine/dragon-tongue-suture-passer.html, last accessed Sep. 29, 2022.

Medtronic, "Port-Site Closure Devices," pp. 1-4 (2022), available at https://www.medtronic.com/covidien/en-us/products/trocars-access/port-site-closure-devices.html; last accessed Sep. 20, 2022.

International Search Report and Written Opinion of PCT/US2022/029627, mailed Jul. 26, 2022, pp. 1-11.

* cited by examiner

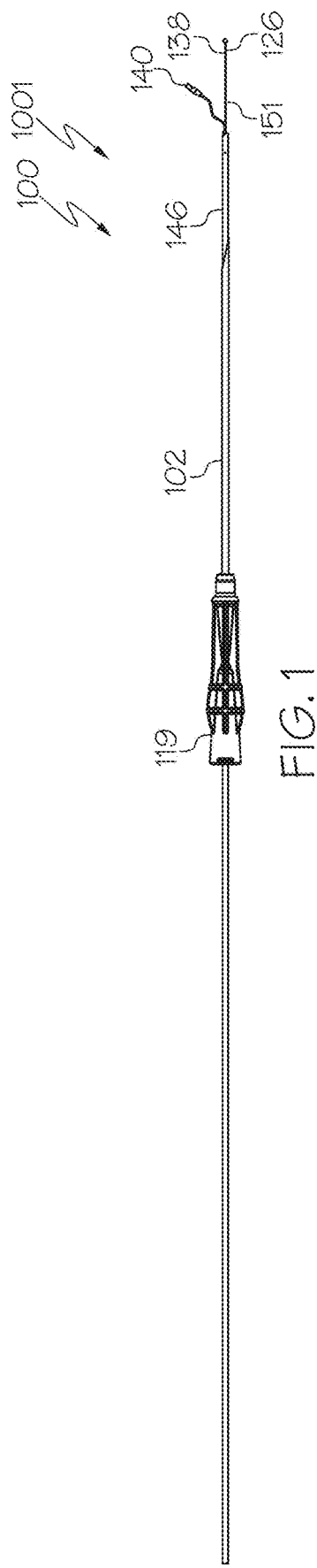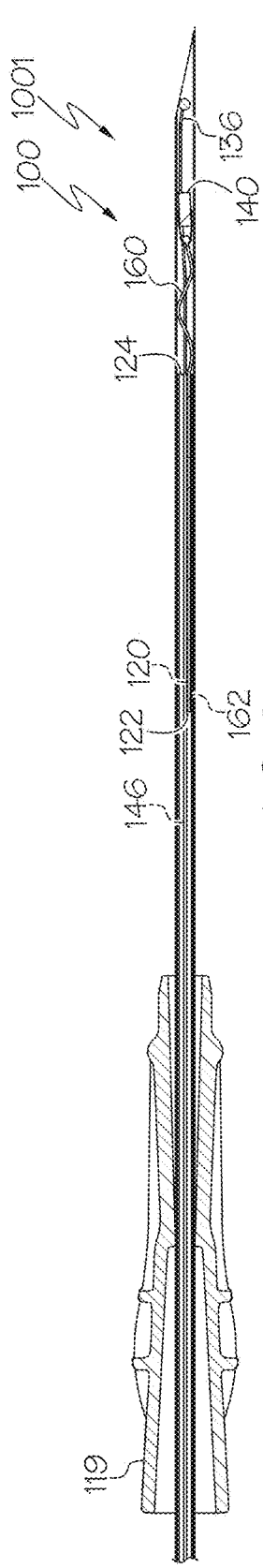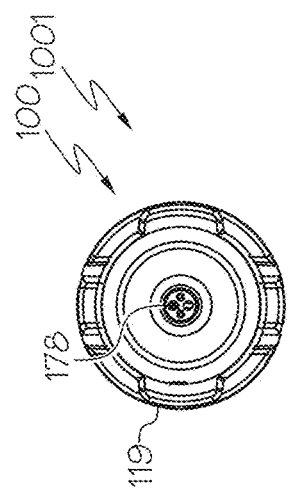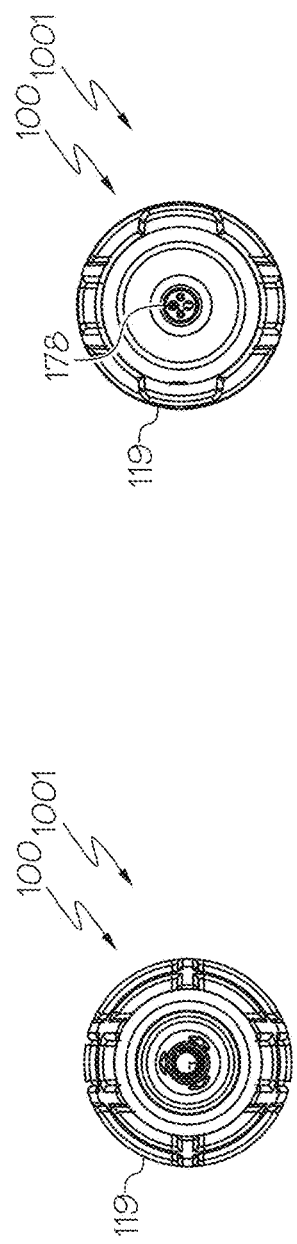

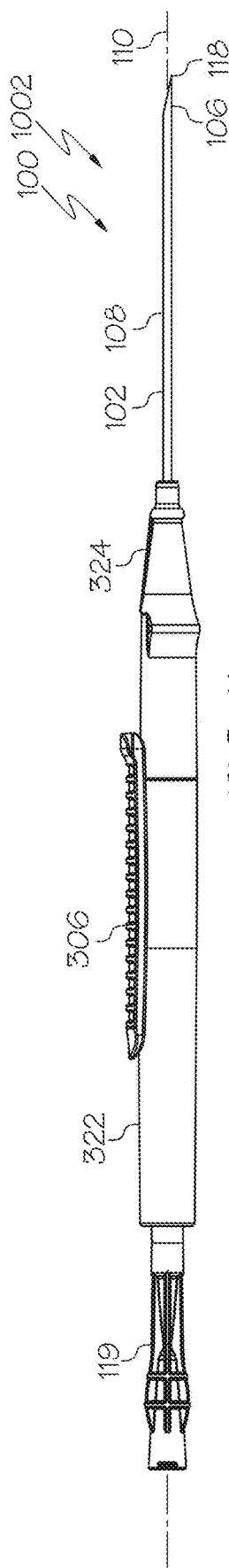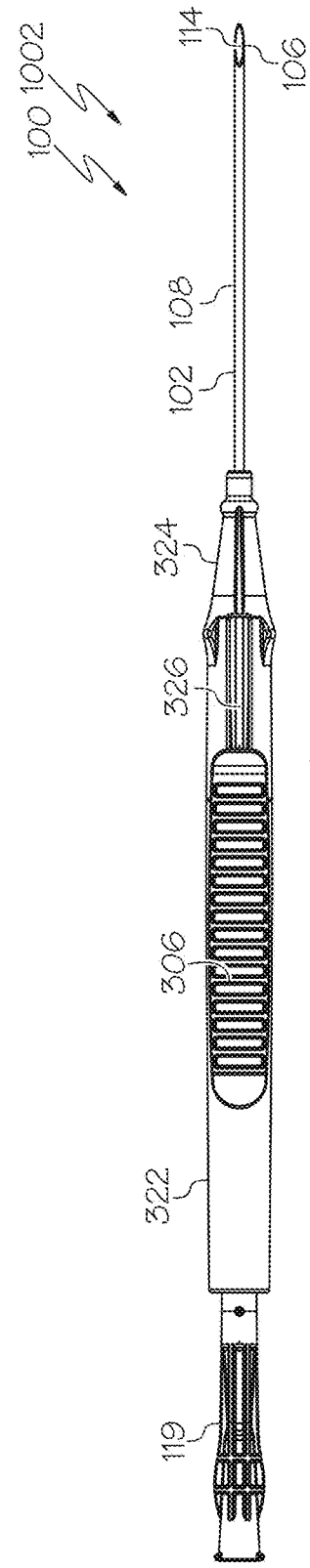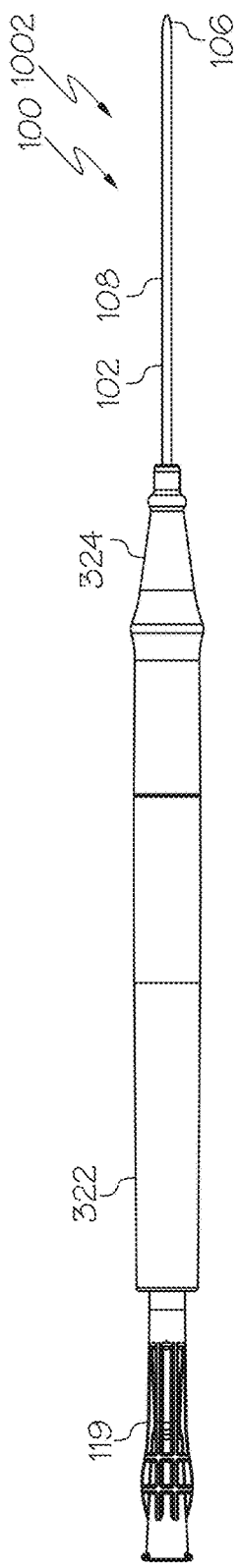

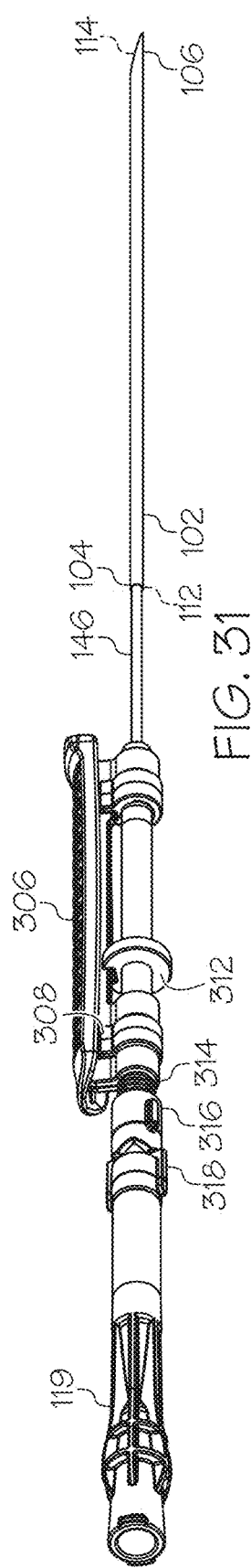
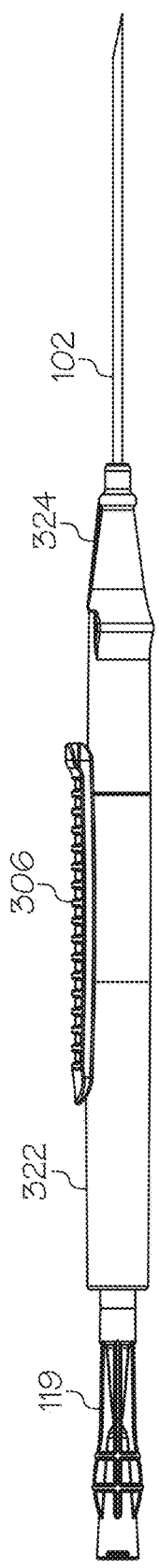
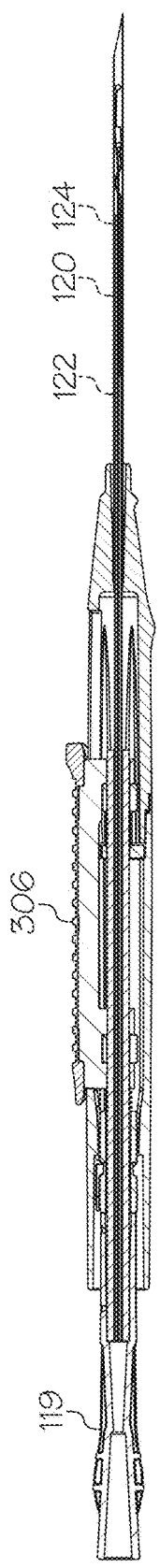
FIG. 31
FIG. 32
FIG. 33

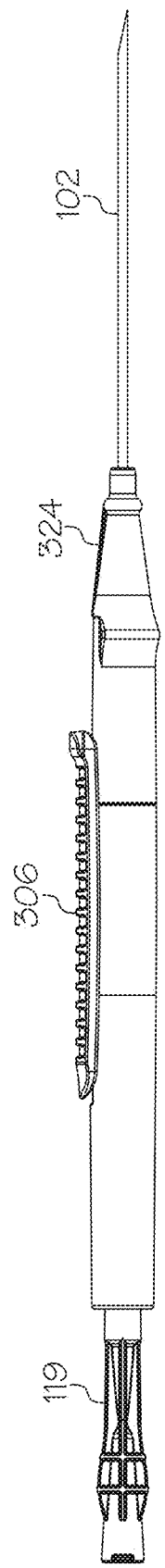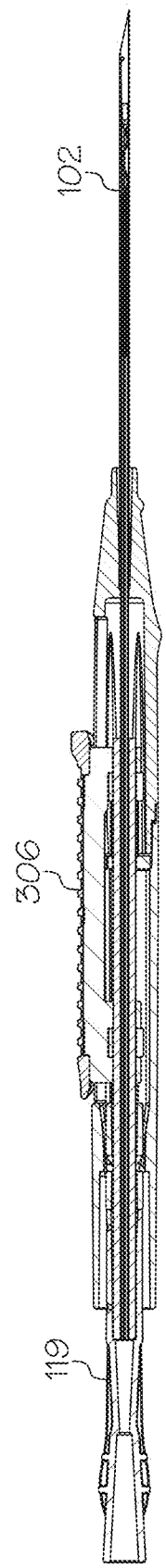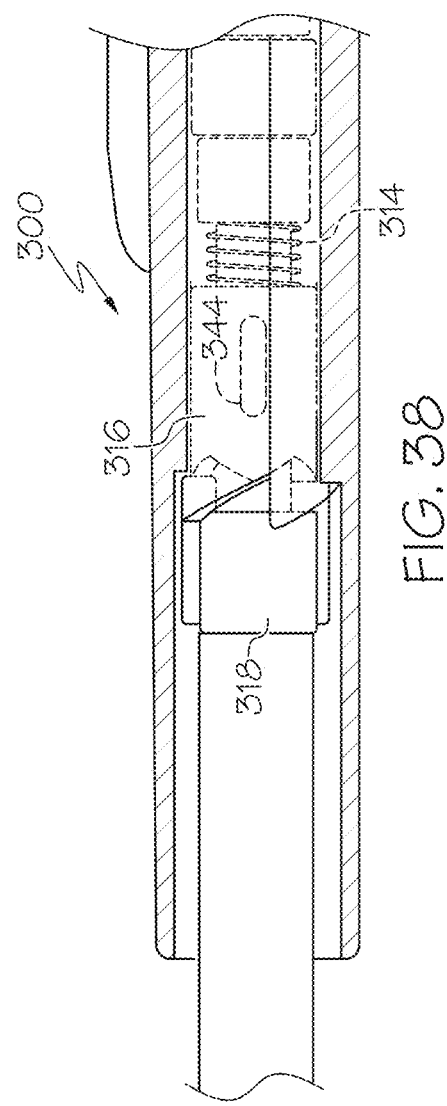

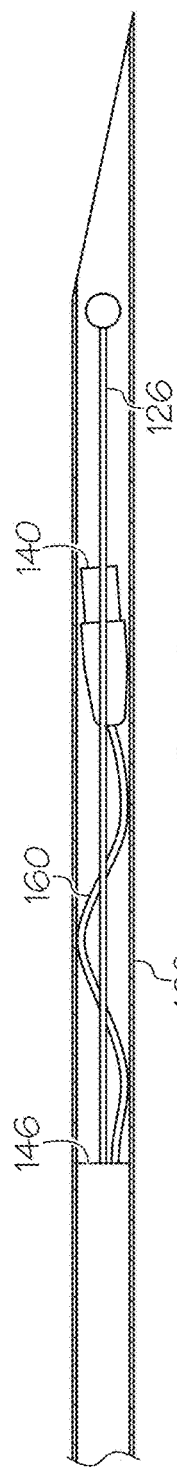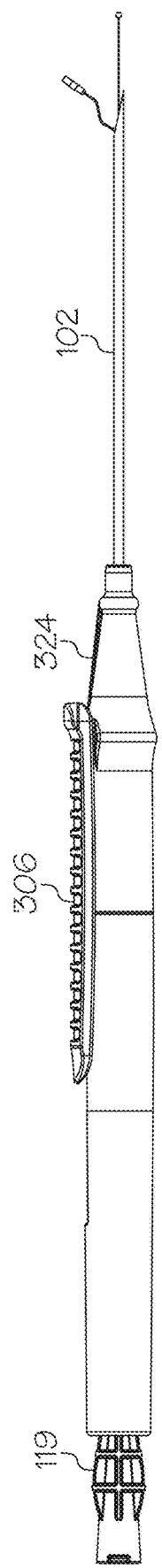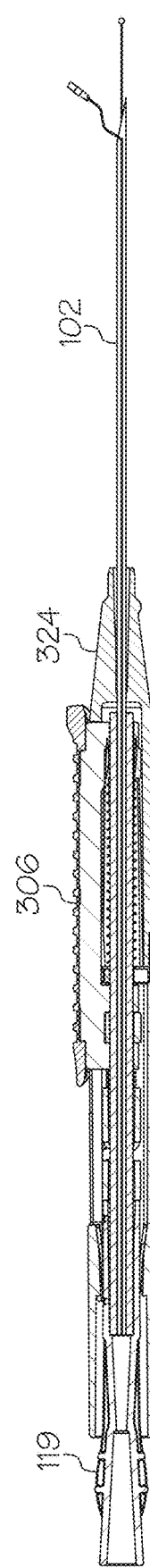

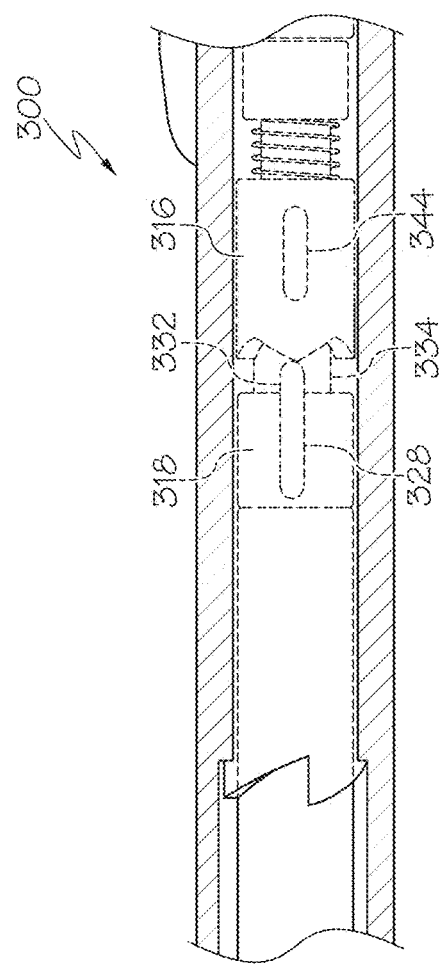
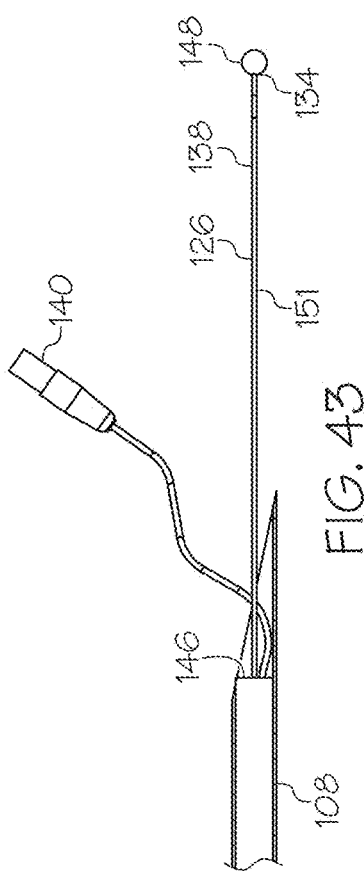

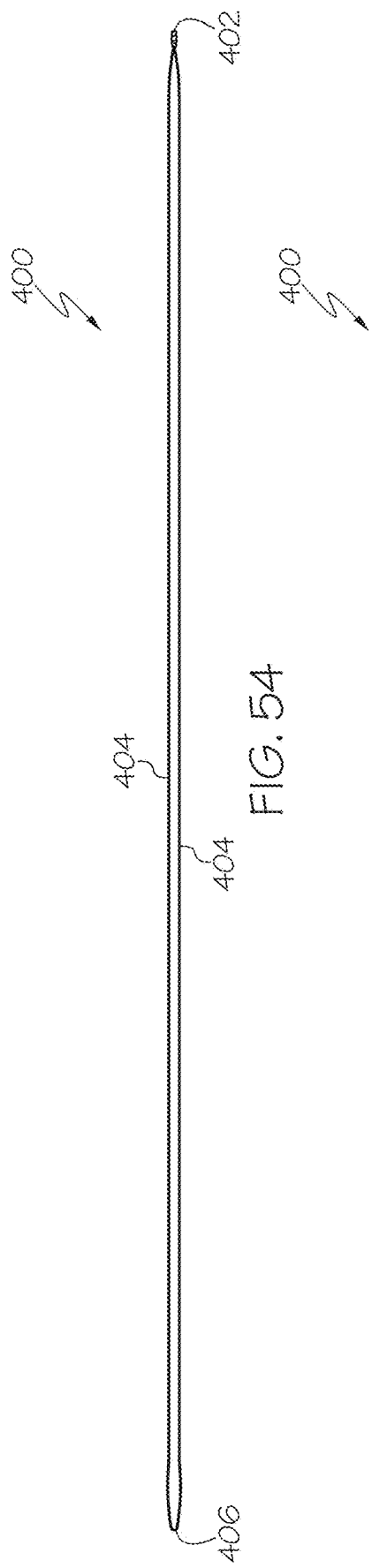
FIG. 54
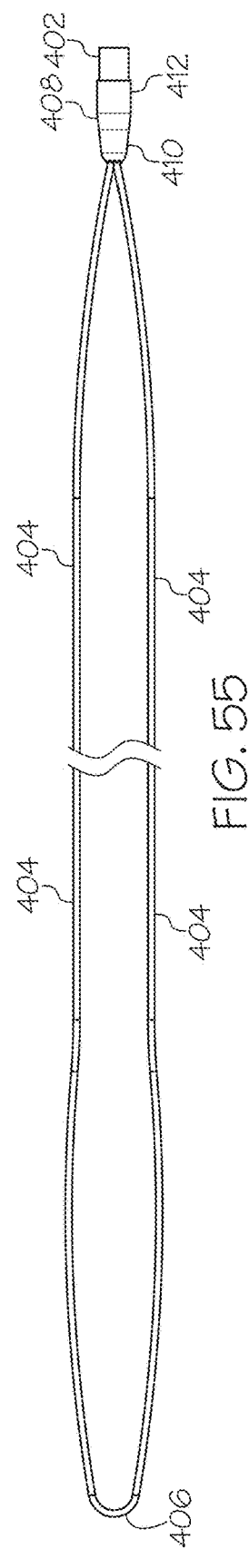
FIG. 55
FIG. 57
FIG. 56

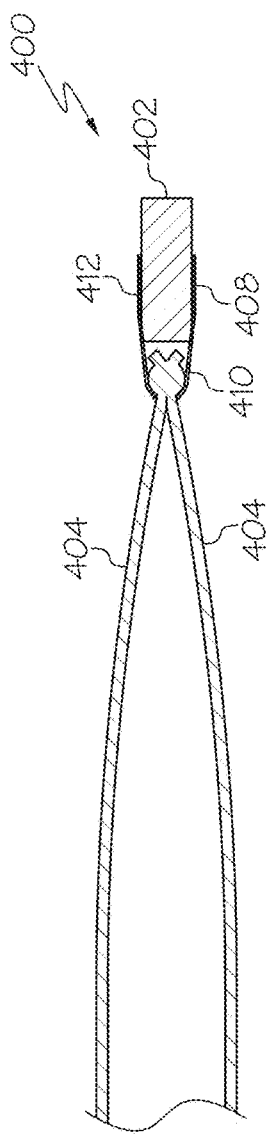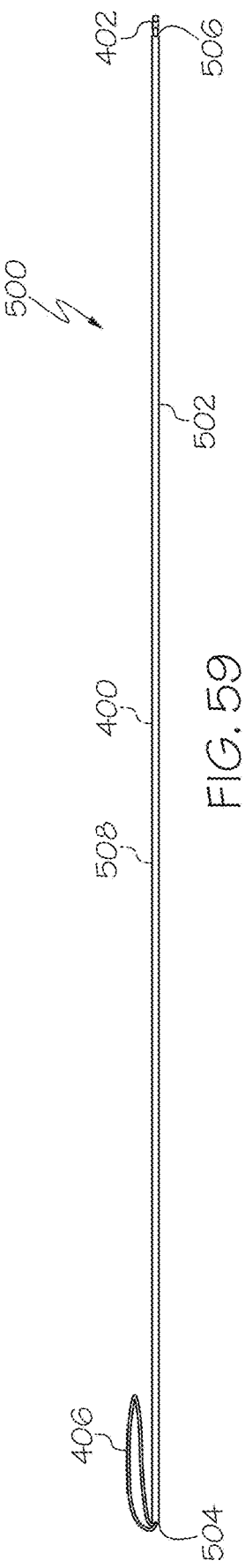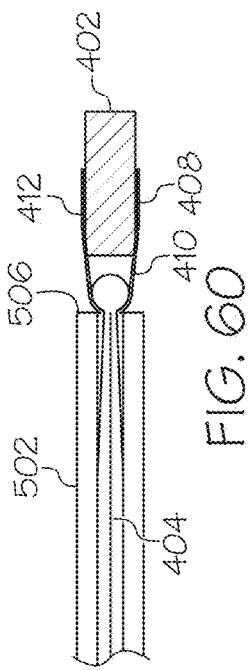

MAGNETIC SUTURE LOOP COMPRISING A SUTURE MAGNET, A BIFURCATED SUTURE, AND A CARTRIDGE TUBE

CROSS-REFERENCE TO RELATED APPLICATIONS

This application is a continuation of U.S. application Ser. No. 17/995,779, filed Oct. 7, 2022, now U.S. Pat. No. 11,839,373, which is a national stage application of International Appl. PCT/US2022/029627, filed May 17, 2022, and which claims the benefit of U.S. Provisional Application No. 63/268,596, filed Feb. 25, 2022, and U.S. Provisional Application No. 63/189,511, filed May 17, 2021, all of which are hereby incorporated by reference.

FIELD OF THE INVENTION

The invention relates to a magnet-assisted suture grasper for grasping a magnetic suture, and more particularly to a magnet-assisted suture grasper for grasping a magnetic suture comprising a suture retrieval needle, a retriever body, a grasper wire, a grasper arm, and a grasper magnet.

BACKGROUND OF THE INVENTION

Suture passing is required in many surgical procedures. A suture passer is a surgical instrument which provides a means of delivery and/or retrieval of a suture through some bodily tissue. There are many existing instruments on the market which utilize a mechanical solution to secure a suture for passing.

Increasingly, minimally invasive techniques are being employed over open surgery due to reduction in risk, faster recovery time, and generally better cosmesis. Minimally invasive techniques typically make use of a scope and specialized tools that can be inserted through existing openings of a patient (e.g., via endoscope, colonoscope, etc.) or artificially created openings of the patient (e.g., via laparoscope, arthroscope, etc.) to gain access to the targeted intracorporeal working space.

Working with indirect visualization of surgical instruments through a scope presents a significant technical challenge to the use of suture passers for retrieval. Retrieving a suture using a typical suture passer requires precise positioning and careful manipulation of the suture passer to position one or more grasping elements of the suture passer around the suture. The suture passer must be held relatively steady in position while the grasping elements are closed about the suture, capturing the suture and holding it firmly so it can be retrieved Skillful manipulation in this manner is hampered by the fact that most scopes employ a single camera and present a two-dimensional image to the suture passer operator and thus do not provide stereoscopic imaging. The lack of stereoscopic imaging hampers the operator's ability to perceive depth, which increases the level of difficulty associated with precisely positioning the grasping elements around the suture. While three-dimensional imaging systems exist, they are expensive and to date remain relatively rare in the field.

Most existing suture passer designs utilize a multi-arm design, where two or more arms are opened and brought around a suture, then closed around the suture to capture it. The arms may be separate, creating a pincer-style grasper with jaws to grasp a suture, or they may be connected, forming a snare-type grasper forming an eye through which a suture can be threaded.

Unfortunately, regardless of the arm design, these devices require precise positioning to get the jaws of the grasper around the suture, or to thread the suture through the eye of the snare before the suture can be captured. As noted, this is difficult under indirect visualization because camera systems for indirect visualization are typically non-stereoscopic. Without a three-dimensional image, a surgeon must rely on visual cues to judge the instrument position and depth, which makes it difficult to get the instrument positioned properly. Once the instrument is in position, the surgeon then needs to hold the instrument and the suture very steady while attempting to close the grasper around the suture. The long moment arm created by the length of the instrument magnifies even very minor movements, so that a small movement can bring the two components out of alignment. Failed attempts at grasping a suture can extend procedure times and lead to frustration in the operating room.

A magnetic U-stitch suturing device intended to address these difficulties has been disclosed in U.S. Pat. No. 10,245,021. The magnetic U-stitch suturing device is made of two hypodermic needles allowing one or more sutures, at the same time, and a retrieval probe to be advanced into a cavity, such as a stomach cavity, of a patient. The one or more sutures can be magnetic sutures, each including a suture magnet, as described in U.S. Pub. No. 2021/0059667. Both the suture and retrieval probe comprise magnets of opposite polarities on their leading ends. Thus, after the suture and retrieval probe are inside the stomach cavity, the suture and retrieval probe may mate and the suture may be transferred from one hypodermic needle to the other using magnetic attraction. In doing so, the suture forms a loop through the stomach. Once removed, this loop, having two ends that are positioned outside the patient's body, can be pulled tight in order to pull the stomach wall closer to the surface of the patient's body. With the stomach wall close to the surface of the patient's body, it is easier to insert a gastrostomy device.

Unfortunately, certain procedures, such as inguinal hernia repair through high ligation of the patent processus vaginalis, require passing of a suture in a space, e.g., a peritoneal cavity, that is not sufficiently large to permit advancement of the two hypodermic needles of the magnetic U-stitch suturing device simultaneously.

Other suture instruments and/or sutures including magnets also have been disclosed. For example, U.S. Pat. No. 10,299,786 discloses a suture insertion device utilizing small gauge needles for threading one or more sutures through subcutaneous tissue. The suture insertion device can include a magnetic capture mechanism for contacting a magnetically attractive strand in transverse alignment. U.S. Pat. Nos. 6,719,765 and 9,770,238 disclose instruments for passing a medical implement through tissue with magnetic forces. U.S. Pat. No. 8,702,753 and U.S. Pub. No. 2008/0243148 disclose sutures to which magnetic anchors are attached. U.S. Pub. No. 2020/0360017 discloses a suturing apparatus in which a suture thread may be automatically passed between a needle and a transfer tube. The suturing apparatus can include electromagnetic coils to engage and release a suture from the system. U.S. Pub. No. 2020/0214695 discloses a suturing system including a forceps arm and a suture that may be magnetic to thus engage with each other. U.S. Pub. No. 2022/0104802 discloses a suturing system including a rod having a magnetic tube extending from an end thereof and a magnetic needle having an end attracted into the tube to magnetically engage therewith. U.S. Pub. No. 2021/0059667 discloses a magnetic suture that has a ferrule with a tapered region in which a knotted suture is provided and secured with an adhesive and a straight region in which a magnet is provided.

Improved suture passers that reduce the technical difficulty associated with capturing and retrieving sutures under indirect non-stereoscopic visualization are needed.

BRIEF SUMMARY OF THE INVENTION

A magnet-assisted suture grasper for grasping a magnetic suture is disclosed. The magnet-assisted suture grasper comprises: (a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis; (b) a retriever body disposed within the needle lumen and translatable therein along the needle body axis; (c) a grasper wire having a proximal end and a distal end and being fixedly disposed within the retriever body; (d) a grasper arm comprising a proximal end, a proximal-to-intermediate portion, a distal portion, and a distal end, the grasper arm extending from the distal end of the grasper wire and being reversibly moveable between a first position and a second position; and (e) a grasper magnet being disposed adjacent the proximal-to-intermediate portion of the grasper arm, the magnet-assisted suture grasper sequestering the grasper magnet within the needle lumen when the grasper arm is in the first position and exposing the grasper magnet from the needle lumen when the grasper arm is in the second position. The distal end of the grasper arm extends further distally than the grasper magnet. Translation of the retriever body within the needle lumen in a first direction along the needle body axis causes the grasper arm to move from the first position to the second position, thereby exposing the grasper magnet and allowing contact between the grasper magnet and a magnetic suture attracted thereto. Translation of the retriever body within the needle lumen in a second direction opposite the first direction along the needle body axis causes the grasper arm to move from the second position to the first position, thereby sequestering the grasper magnet and grasping the magnetic suture within the needle lumen.

In some embodiments, the suture retrieval needle is a hypodermic needle.

In some embodiments, the suture retrieval needle is straight, the needle body axis thereby being straight.

In some embodiments the suture retrieval needle is curved, the needle body axis thereby being curved.

In some embodiments, the suture retrieval needle has a sharp tip.

In some embodiments, the suture retrieval needle further comprises a hub.

In some embodiments, the retriever body and the grasper wire are more flexible than the needle body.

In some embodiments, the retriever body comprises a proximal end, a distal end, and a retriever tube extending therebetween, the retriever tube defining a retriever tube axis between the proximal and distal ends of the retriever body, the retriever tube having a proximal hole, a distal hole, and a retriever tube lumen extending therebetween along the retriever tube axis; and the proximal hole of the retriever tube is in fluid communication with the distal hole of the needle body through the retriever tube lumen and the needle lumen.

In some embodiments, the grasper arm is integral to the grasper wire.

In some embodiments, the magnet-assisted suture grasper further comprises a magnet wire having a proximal end and a distal end, wherein the proximal end of the magnet wire is fixedly disposed within the retriever body and the grasper magnet is fixedly attached to the distal end of the magnet wire, either directly or indirectly.

In some of these embodiments, the magnet wire further comprises a magnet wire distal terminus at the distal end of the magnet wire, the magnet-assisted suture grasper further comprises a ferrule attached to the magnet wire distal terminus, and the grasper magnet is attached to the ferrule.

In some embodiments, the grasper magnet is fixedly attached to the grasper arm, either directly or indirectly.

In some embodiments, the grasper magnet is fixedly attached to the grasper wire, either directly or indirectly.

In some embodiments, the grasper arm further comprises an enlarged distal terminus at the distal end of the grasper arm; the grasper arm is reversibly moveable between the first position and the second position based on translation of the grasper arm from inside of the needle lumen to outside of the needle lumen through the distal hole of the needle body; and the enlarged distal terminus at the distal end of the grasper arm has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

In some embodiments, the grasper wire is a first grasper wire; the grasper arm is a first grasper arm; the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position; the first grasper arm further comprising an enlarged distal terminus at the distal end of the first grasper arm; the second grasper arm further comprising an enlarged distal terminus at the distal end of the second grasper arm; the first and second grasper arms are reversibly moveable between the first position and the second position based on translation of the first and second grasper arms from inside of the needle lumen to outside of the needle lumen through the distal hole of the needle body; and the enlarged distal termini of the first and second grasper arms have sizes sufficiently small to allow contact between the grasper magnet and a suture magnet of a magnetic suture attracted thereto when the first and second grasper arms are in the second position and to allow a suture of the magnetic suture to pass when the first and second grasper arms are in the first position, and sufficiently large to block the suture magnet of the magnetic suture from exiting the needle lumen through the distal hole of the needle body when the first and second grasper arms are in the first position.

In some of these embodiments, the magnet-assisted suture grasper further comprises at least one additional grasper wire and at least one additional grasper arm extending distally from the at least one additional grasper wire.

In some embodiments, the grasper wire is a first grasper wire; the grasper arm is a first grasper arm; the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position; the first and second grasper arms are connected at their distal ends, thereby forming a grasper arm loop; the grasper arm loop is reversibly moveable between the first position and the second position based on translation of the grasper arm loop from inside of the needle lumen to outside of the needle lumen through the distal hole of the needle body; the grasper arm loop circumscribes an area sufficiently large to allow contact between the grasper magnet and a suture magnet of a magnetic suture attracted thereto when the grasper arm loop is in the second position; and the grasper arm loop has a thickness sufficiently great to block the suture magnet of the magnetic suture from exiting the needle lumen through the distal hole of the suture retrieval needle when the grasper arm loop is in the first position.

In some embodiments, the grasper wire is a first grasper wire; the grasper arm is a first grasper arm; the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position; the first and second grasper arms are connected at their distal ends, thereby forming a grasper arm loop; the first and second grasper arms further comprise an enlarged distal terminus at the distal ends of the first and second grasper arms; the grasper arm loop is reversibly moveable between the first position and the second position based on translation of the grasper arm loop from inside of the needle lumen to outside of the needle lumen through the distal hole of the needle body; the grasper arm loop circumscribes an area sufficiently large, and the enlarged distal terminus at the distal ends of the first and second grasper arms has a size sufficiently small, to allow contact between the grasper magnet and a suture magnet of a magnetic suture attracted thereto when the grasper arm loop is in the second position; the enlarged distal terminus at the distal ends of the first and second grasper arms has a size sufficiently small to allow a suture of the magnetic suture to pass when the grasper arm loop is in the first position; and the enlarged distal terminus at the distal ends of the first and second grasper arms has a size sufficiently large to block the suture magnet of the magnetic suture from exiting the needle lumen through the distal hole of the needle body when the grasper arm loop is in the first position.

In some embodiments, the grasper wire is a first grasper wire; the grasper arm is a first grasper arm; the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position; the first and second grasper arms are connected at their distal ends, thereby forming a grasper arm loop; the grasper arm loop is reversibly moveable between the first position and the second position based on translation of the grasper arm loop from inside of the needle lumen to outside of the needle lumen through the distal hole of the needle body; the grasper arm loop is in an elastically deformed closed state when the grasper arm loop is in the first position; the grasper arm loop reversibly expands to an open state when the grasper arm loop is in the second position; the grasper arm loop circumscribes an area sufficiently large to allow contact between the grasper magnet and a suture magnet of a magnetic suture attracted thereto when the grasper arm loop is in the second position; and the grasper arm loop snares the suture magnet of the magnetic suture to block the suture magnet from exiting the needle lumen through the distal hole of the suture retrieval needle when the grasper arm loop is in the first position.

In some of these embodiments, the grasper arm loop is formed of a shape memory alloy.

In some embodiments, the grasper wire is a first grasper wire; the grasper arm is a first grasper arm; the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position; the first and second grasper arms comprise curved portions adjacent their distal ends; the first and second grasper arms are reversibly moveable between the first position and the second position based on translation of the first and second grasper arms from inside of the needle lumen to outside of the needle lumen through the distal hole of the needle body; the proximal-to-intermediate portions of the first and second grasper arms are substantially parallel to the needle body axis and the curved portions adjacent the distal ends of the first and second grasper arms curve inwardly toward the needle body axis when the first and second grasper arms are in the first position; at least one of the first or second grasper arms pivots reversibly outwardly from the needle body axis sufficiently far to allow contact between the grasper magnet and a magnetic suture attracted thereto when the first and second grasper arms are in the second position; and the curved portions adjacent the distal ends of the two grasper arms contact the magnetic suture to block the magnetic suture from exiting the needle lumen through the distal hole of the suture retrieval needle when the first and second grasper arms are in the first position.

In some embodiments, the magnet-assisted suture grasper further comprises a lock mechanism that can be reversibly engaged to prevent translation of the retriever body within the needle lumen in the first direction and/or the second direction.

In some of these embodiments, the lock mechanism can be reversibly engaged in a first setting that prevents translation of the retriever body within the needle lumen when the distal end of the grasper arm is inside the needle lumen and reversibly engaged in a second setting that prevents translation of the retriever body within the needle lumen when the grasper magnet is outside of the needle lumen.

In some of these embodiments, maintaining the lock mechanism in the first setting or the second setting does not require energy input.

A system for passing a magnetic suture also is disclosed. The system comprises the magnet-assisted suture grasper. The system also comprises a magnetic suture comprising a suture magnet and a suture extending from the suture magnet.

Another system for passing a magnetic suture also is disclosed. The system comprises the magnet-assisted suture grasper. The system also comprises a magnetic suture loop comprising a suture magnet and a bifurcated suture extending from the suture magnet and forming a suture loop.

In some embodiments, the system further comprises a cartridge tube, wherein the cartridge tube comprises a cartridge tube proximal opening, a cartridge tube distal opening, and a cartridge tube lumen therebetween; the suture loop traverses the cartridge tube lumen based on having been inserted through the cartridge tube distal opening; and the suture magnet is disposed outside of the cartridge tube lumen adjacent the cartridge tube distal opening.

BRIEF DESCRIPTION OF THE DRAWINGS

These and other features, aspects, and advantages of the present disclosure are better understood when the following detailed description is read with reference to the accompanying drawings, which are as follows.

FIG. 1 is a side view of a first embodiment of a magnet-assisted suture grasper comprising a suture retrieval needle, a retriever body, a grasper wire, a grasper arm, and a grasper magnet, as disclosed herein, in which the grasper arm is in a position exposing the grasper magnet and allowing contact between the grasper magnet and a magnetic suture attracted thereto, termed the second position, as discussed herein.

FIG. 2 is a sectional view of the magnet-assisted suture grasper of FIG. 1, in which the grasper arm is in a position sequestering the grasper magnet within the needle lumen, termed the first position, as discussed herein.

FIG. 3 is a front view of the magnet-assisted suture grasper of FIG. 1, in which the grasper arm is in the first position.

FIG. 4 is a back view of the magnet-assisted suture grasper of FIG. 1.

FIG. 11 is a side view of a second embodiment of a magnet-assisted suture grasper comprising a suture retrieval needle, a retriever body, a grasper wire, a grasper arm, and a grasper magnet as disclosed herein, in which the grasper arm is in the first position.

FIG. 12 is a top view of the magnet-assisted suture grasper of FIG. 11, in which the grasper arm is in the first position.

FIG. 13 is a bottom view of the magnet-assisted suture grasper of FIG. 11, in which the grasper arm is in the first position.

FIG. 31 is a perspective view of an advancer assembly of the magnet-assisted suture grasper of FIG. 11.

FIG. 32 is a side view of the magnet-assisted suture grasper of FIG. 11, in which the advancer assembly is in an unlocked retracted position and the grasper arm is in the first position.

FIG. 33 is a side view of the magnet-assisted suture grasper of FIG. 11, in which the advancer assembly is in the unlocked retracted position and the grasper arm is in the first position.

FIG. 36 is a side view of the magnet-assisted suture grasper of FIG. 11, in which the advancer assembly is in a locked intermediate position and the grasper arm is in a position intermediate between the first position and the second position.

FIG. 37 is a side view of the magnet-assisted suture grasper of FIG. 11, in which the advancer assembly is in the locked intermediate position and the grasper arm is in a position intermediate between the first position and the second position.

FIG. 38 is a partial sectional view of a subset of components of the advancer assembly of the magnet-assisted suture grasper of FIG. 11, in which the advancer assembly is in the locked intermediate position.

FIG. 39 is a side view of the distal end of the magnet-assisted suture grasper of FIG. 11, in which the advancer assembly is in the locked intermediate position and the grasper arm is in a position intermediate between the first position and the second position.

FIG. 40 is a side view of the magnet-assisted suture grasper of FIG. 11, in which the advancer assembly is in a locked extended position and the grasper arm is in the second position.

FIG. 41 is a side view of the magnet-assisted suture grasper of FIG. 11, in which the advancer assembly is in the locked extended position and the grasper arm is in the second position.

FIG. 42 is a partial sectional view of a subset of parts of the advancer assembly of the magnet-assisted suture grasper of FIG. 11, in which the advancer assembly is in the locked extended position.

FIG. 43 is a side view of the distal end of the magnet-assisted suture grasper of FIG. 1, in which the grasper arm is in the second position. This also is a side view of the distal end of the magnet-assisted suture grasper of FIG. 11, in which the advancer assembly is in the locked extended position and the grasper arm is in the second position.

FIG. 44 is a side view of the distal end of the magnet-assisted suture grasper of FIG. 1, in which the grasper arm is in the second position and the grasper magnet is attracting a magnetic suture. This also is a side view of the distal end of the magnet-assisted suture grasper of FIG. 11, in which the advancer assembly is in the locked extended position, the grasper arm is in the second position, and the grasper magnet is attracting a magnetic suture.

FIG. 54 is a top view of a magnetic suture loop as disclosed herein.

FIG. 55 is an expanded view of a loop-end and a magnet-end of the magnetic suture loop of FIG. 54.

FIG. 56 is a front view of the magnetic suture loop of FIG. 54.

FIG. 57 is a back view of the magnetic suture loop of FIG. 54.

FIG. 58 is an expanded sectional view of the magnet-end of the magnetic suture loop of FIG. 54.

FIG. 59 is a side view of a preloaded magnetic suture cartridge as disclosed herein.

FIG. 60 is a sectional view of the magnet-end of the preloaded magnetic suture cartridge of FIG. 59.

DETAILED DESCRIPTION

Figure 5:
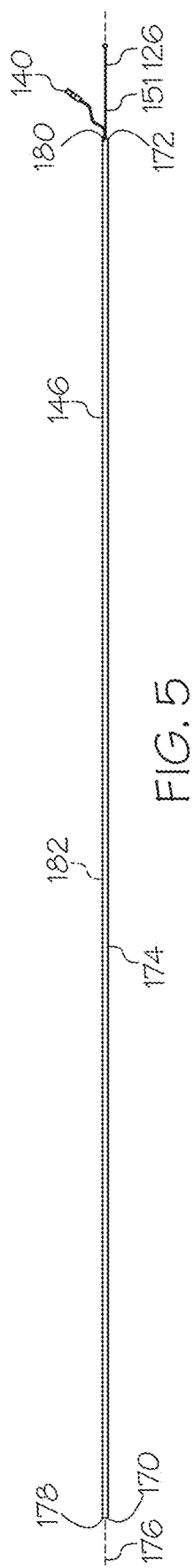
FIG. 5 is a side view of a portion of the magnet-assisted suture grasper of FIG. 1 comprising the retriever body, the grasper wire, the grasper arm, and the grasper magnet, in which the grasper arm is in the second position.
Figure 6:
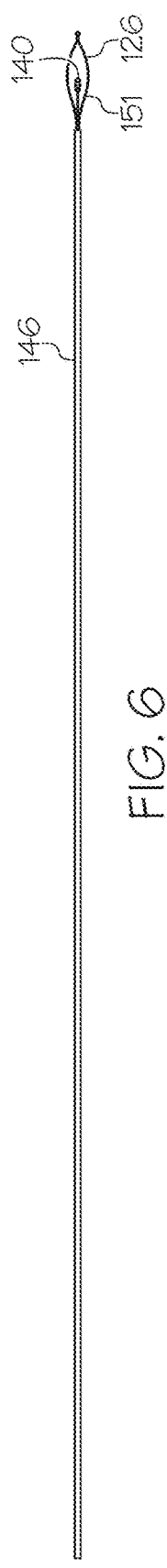
FIG. 6 is a top view of the portion of the magnet-assisted suture grasper of FIG. 5, in which the grasper arm is in the second position.

A magnet-assisted suture grasper for grasping a magnetic suture is disclosed. The magnet-assisted suture grasper comprises: (a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis; (b) a retriever body disposed within the needle lumen and translatable therein along the needle body axis; (c) a grasper wire having a proximal end and a distal end and being fixedly disposed within the retriever body; (d) a grasper arm comprising a proximal end, a proximal-to-intermediate portion, a distal portion, and a distal end, the grasper arm extending from the distal end of the grasper wire and being reversibly moveable between a first position and a second position; and (e) a grasper magnet being disposed adjacent the proximal-to-intermediate portion of the grasper arm, the magnet-assisted suture grasper sequestering the grasper magnet within the needle lumen when the grasper arm is in the first position and exposing the grasper magnet from the needle lumen when the grasper arm is in the second position. The distal end of the grasper arm extends further distally than the grasper magnet. Translation of the retriever body within the needle lumen in a first direction along the needle body axis causes the grasper arm to move from the first position to the second position, thereby exposing the grasper magnet and allowing contact between the grasper magnet and a magnetic suture attracted thereto. Translation of the retriever body within the needle lumen in a second direction opposite the first direction along the needle body axis causes the grasper arm to move from the second position to the first position, thereby sequestering the grasper magnet and grasping the magnetic suture within the needle lumen.

Our magnet-assisted suture grasper addresses the technical difficulty associated with capturing and retrieving sutures under indirect non-stereoscopic visualization. Our magnet-assisted suture grasper involves use of two dipole magnets, a grasper magnet of a magnet-assisted suture grasper and a suture magnet of a magnetic suture, to assist with the initial positioning and holding of a magnetic suture while the magnetic suture is captured by a secondary mechanical means of the magnet-assisted suture grasper. The use of the two dipole magnets allows for a self-aligning feature, whereby the attractive forces of the northern and southern poles of the grasper magnet and the suture magnet cause the two magnets to align in a predictable manner, improving aspects of repeatability and reliability of function. Our magnet-assisted suture grasper greatly reduces the need to precisely position a suture passer, as the two magnetic aspects need only be brought near enough to one another that the magnetic fields can interact. The magnetic aspect of the suture is pulled into contact with the grasper magnet. This occurs without need for precise positioning to make contact. The secondary mechanical means then provides a steady-state connection between the magnetic suture and the magnet-assisted suture grasper that serves to hold the suture to the magnet-assisted suture grasper, allowing retrieval of the suture through soft tissue of a patient without needing to rely on magnetic attraction between the grasper magnet and the suture magnetic during the retrieval.

While we initially envisioned that sutures would be retrieved from a patient's body relying on the magnetic attraction between the grasper magnet and the suture magnet, in vitro testing revealed a problem whereby frictional drag associated with pulling a suture through soft tissues was greater than the attractive force between the grasper magnet and the suture magnet, resulting in separation of the magnets. The two magnets were too small. The size of the magnets is restricted by the need to pass them through a cannula for delivery, and the desire to minimize the size of the cannula to minimize trauma associated with tissue penetration by the cannula. We could not increase the size of the magnets to provide a greater attractive strength. We realized, though, that we could solve this problem by using a mechanical trap that works in conjunction with the walls of the cannula to secure the suture against greater loads than the magnetic connection can withstand.

More specifically, initially we intended to incorporate a magnetic suture, including a suture magnet, such as the magnetic suture described in U.S. Pub. No. 2021/0059667, and a device including a magnetic suture retriever with a magnetic end, similar to the retrieval probe of the magnetic U-stitch suturing device described in U.S. Pat. No. 10,245,021. The suture would be introduced using a 17 gauge hypodermic needle. For certain procedures, such as the inguinal hernia repair technique referenced above, the needle must then be removed before introduction of a retriever. In the inguinal hernia repair procedure, the suture would be deposited with the magnetic end inside the peritoneal cavity, and the suture extending through the abdominal wall. The magnetic suture retriever would then be introduced through the same percutaneous site, using a 17 gauge needle. This could be a second needle, or it could be the same needle that was used to introduce the suture. The magnetic suture retriever would then be brought near the magnetic end of the suture so that the magnets would connect. Once the magnets were connected, the magnetic retriever would be withdrawn, pulling the suture with it.

While prototyping this device, we determined that the attractive force between the magnets of the magnetic suture retriever and the magnetic suture was not strong enough to resist the frictional drag that results from pulling the suture through soft tissue. For comparison, for the magnetic U-stitch device described in U.S. Pat. No. 10,245,021, the suture never contacts tissue during retrieval. Instead, the suture travels through one cannula, into an open space, and then back through another cannula. There is minimal drag created by passing the suture through these cannulas. However, in the case of the inguinal hernia procedure, which is typically done on pediatric patients, there is not sufficient room for two needles to occupy relevant space in the patient simultaneously. The suture needs to be dropped first from an introducer needle. Then the introducer needle needs to be removed. Then the magnetic suture retriever would need to be able to retrieve the suture.

We realized, though, that the frictional drag created by pulling the suture through soft tissue is a problem. The drag creates a tensile load on the suture which is greater than the attractive force between the magnets, causing the magnets to disconnect and the suture to be dropped. Due to the small size of the pediatric patients, increasing the size of the introducer needle would be disadvantageous. However, without increasing the size of the needle, the diameter of magnets that can be used is limited, which limits the strength of the attractive force between the magnets. A current design for the magnetic U-stitch device uses a 17 gauge XT wall hypodermic needle that has an inner lumen diameter of 0.049-0.051 inches (1.24 to 1.30 mm), accounting for manufacturing tolerances. The corresponding magnet has a nominal outer diameter of 0.035 inches (0.889 mm), and a ferrule diameter of 0.037±0.001 inches (0.940±0.025 mm). Each magnet has a pull force of approximately 0.102 lbf (0.454 N). Even increasing the magnet diameter to the theoretical max of 0.042 inches (1.07 mm), allowing for manufacturing tolerances and a minimal clearance of only 0.001 inches (0.025 mm), would only increase that pull force to approximately 0.145 lbf (0.645 N). A much larger magnet would be needed to overcome the drag of the soft tissue, but a larger magnet cannot be used due to the limitation imposed on needle size.

We have solved this problem, among other ways, by pairing the magnet on the retrieval device, termed a grasper magnet, with a mechanical arm, termed a grasper arm, with an enlarged distal terminus, a loop configuration, and/or other features that can mechanically block the exit path of the magnetic suture once the suture has been pulled into the needle of the retrieval device. With the mechanical block in place, the ability to retain the magnetic suture against a tensile load is limited only by the strength of the mechanical arm, which can be far greater than the attractive force between the small grasper magnet and the small suture magnet. Our testing shows that the grasper arm advantageously retains the magnetic suture against forces far greater than the grasper magnet and the suture magnet can withstand. Indeed, the grasper arm advantageously retains the magnetic suture against forces great enough to break the suture, which is required to have a tensile strength of at least 3 lbf (13 N) by USP standards. The mechanical solution is therefore at least approximately 30 times stronger than the grasper magnet and suture magnet alone.

Importantly, we realized that the retrieval instrument with a grasper magnet only needs to be brought near enough to the magnetic suture for the magnetic fields of the grasper magnet and the suture magnet to interact. Advantageously, this does not require very precise positioning. The magnetic fields are oriented such that when the fields begin to interact, the suture magnet is pulled towards the grasper magnet and the magnets self-align and connect in the same orientation each time. While the strength of the grasper magnet and the suture magnet is not great enough to pull the magnetic suture through soft tissue on its own, we realized that it is strong enough to keep the magnets in contact with each other while the retrieval instrument is manipulated, allowing the user to mechanically capture the magnetic suture, even if the retrieval instrument and the magnetic suture are not held very steady.

Optionally, the magnet-assisted suture grasper can further comprise a lock mechanism that can be reversibly engaged to prevent translation of the retriever body within the needle lumen.

Our magnet-assisted suture grasper that optionally includes the lock mechanism can incorporate an incompressible and reversible mechanical lock that, when engaged, fixes the longitudinal position of the grasper arm in at least one direction, and thereby also fixes the position of a magnetic suture being grasped by the grasper arm in the same direction. When engaged, the mechanical lock advantageously bears fully any tensile load applied to the magnetic suture in the same direction. The mechanical lock provides for a single equipoised position. Moreover, a return spring may be added to the magnet-assisted suture grasper to advantageously provide a second equipoised position, allowing the magnet-assisted suture grasper to be switched between positions with a momentary energy input, but requiring no additional energy input to maintain either position.

For comparison, conventional suture passers make use of a spring located between a moveable plunger element and a fixed body element. According to designs of the conventional suture passers, depressing the plunger element by the application of external force compresses the spring, causing the suture passer to transition from a closed position to an open position. Upon release of the plunger element, and thus in the absence of external force, the spring exerts a counterforce back upon the plunger, which returns the suture passer from the open position to the closed position. The conventional suture passers lack a mechanical lock, and thus rely solely on the spring to resist tensile loading of the suture in the direction which acts to pull the suture out of the suture passer. The spring thus needs to be stiff enough that the force required to compress the spring to a position where the suture passer opens sufficiently far to release the suture is greater than the expected loads that will be placed on the suture during retrieval. Additionally, since the conventional suture passers provide for only one equipoised position, which is the closed position, the operator must continually apply an external force great enough to compress the spring in order to maintain an open position of the suture passer while retrieving a suture.

With our magnet-assisted suture grasper including the lock mechanism, these loads are born by the mechanical lock rather than a spring. As a result, a lighter spring can be used, which reduces the operational force needed to move our magnet-assisted suture grasper between open and closed positions. This allows our magnet-assisted suture grasper to be slidingly operated with a single finger, which allows for a more precise gripping style better suited to delicate procedures, such as, for example, dissection and mobilization of the spermatic cord structures away from the peritoneum, such as in percutaneous inguinal ring suturing. Moreover, because the mechanical lock provides an equipoised closed position, the spring action can be reversed to also create an equipoised open position. This advantageously allows an operator to manipulate our magnet-assisted suture grasper in an open position without having to hold forcefully against a spring.

To quantify the significance of this change, consider the design of a suture passer needed to retrieve a 3-0 polyester suture. The minimum tensile strength of a non-absorbable class I suture of 3-0 size, as required by USP <881> is 0.96 kgf (approximately 9.4 N), while the typical tensile strength of a 3-0 polyester braided suture has been observed to be around 1.5-2.0 kgf (approximately 15 to 20 N). In designing our magnet-assisted suture grasper, we realized that it would be desirable to make our magnet-assisted suture grasper such that it could retain sutures up to the full tensile capacity of the sutures.

Using a conventional suture passer, for which the return spring must retain a suture against tensile loading, the spring must be sufficiently stiff to resist compression to a point where the suture passer opens enough to release the suture at up to 2.0 kgf (approximately 20 N). This in turn means that an input force of >2.0 kgf (greater than approximately 20 N) will be required to compress the spring to the open position. Additionally, the operator must apply this >2.0 kgf (greater than approximately 20 N) force continually to maintain the open position.

In our design, the spring only needs to overcome the frictional drag between sliding components. We have found that an input force of 0.045 kgf (approximately 0.44 N) provides sufficient force with an adequate safety factor to assure that our magnet-assisted suture grasper is always returned to the fully open position by the spring. This is the minimum force required by the spring at the lower bound of travel. The maximum force that the spring generates occurs at the upper bound of travel. Working within the geometric constraints of our current design, we may select a typical open-ended music wire spring having an outer diameter of 0.195 inches (4.95 mm) and a wire diameter of 0.008 inches (0.2 mm) and a free length of 3.500 inches (88.90 mm), with 21 coils disposed between ends. We find this spring has a calculated spring rate of 0.195 kgf (1.91 N), resulting in a preload of 0.046 kgf (0.45 N) at the minimal extent of travel, meeting our 0.045 kgf (0.44 N) requirement, and a calculated peak load of 0.063 kgf (0.618 N) at the maximal extent of travel.

Compared to the conventional suture passer, our magnet-assisted suture passer including the lock mechanism advantageously results in a 96.8% decrease in the force needed to move the device between open and closed positions. Additionally, since our magnet-assisted suture passer including the lock mechanism provides for equipoised closed and open positions, this force is only needed momentarily to change positions, and does not need to be continually applied while maneuvering our magnet-assisted suture passer including the lock mechanism.

FIG. 1, with reference to FIGS. 43-47, illustrates a magnet-assisted suture grasper 100 for grasping a magnetic suture 200 corresponding to a first embodiment 1001 that does not comprise a lock mechanism. FIG. 11, with reference to FIGS. 43-47, illustrates a magnet-assisted suture grasper 100 for grasping a magnetic suture 200 corresponding to a second embodiment 1002 that comprises a lock mechanism. Additional views of the first embodiment 1001 are shown in FIGS. 2-10. Additional views of the second embodiment 1002 are shown in FIGS. 12-42, FIG. 48, and FIG. 49A-C. The first embodiment 1001 and the second embodiment 1002 are discussed together with respect to features and variations that apply to both. The first embodiment 1001 also is discussed with respect to a hub, a handle, and a return mechanism and operation of the first embodiment 1001. The second embodiment 1002 also is discussed with respect to features and variations that relate to the lock mechanism and operation of the second embodiment 1002.

With reference to FIG. 44, the magnetic suture 200 to be grasped can comprise a suture magnet 202 and a suture 204 extending from the suture magnet 202. The magnetic suture 200 can be, for example, a magnetic suture as described in U.S. Pub. No. 2021/0059667, which is incorporated herein by reference. Thus, the magnetic suture 200 can further comprise a ferrule 206 with a tapered region 208 in which the suture 204 is provided knotted and secured with an adhesive and a straight region 210 in which the suture magnet 202 is provided.

Figure 9:
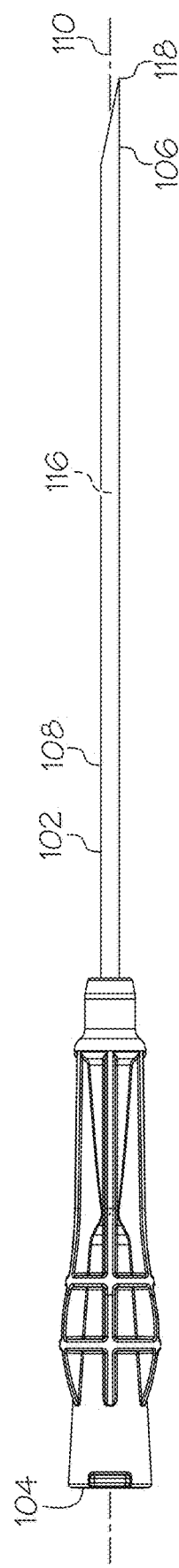
FIG. 9 is a side view of the suture retrieval needle of the magnet-assisted suture grasper of FIG. 1.
Figure 10:
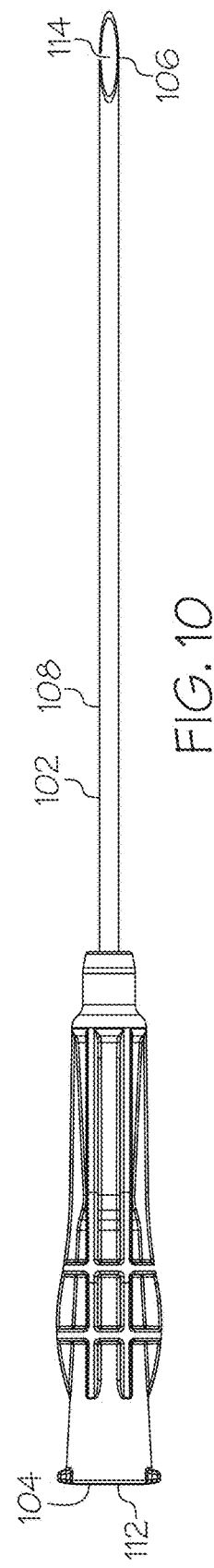
FIG. 10 is a top view of the suture retrieval needle of FIG. 9.

As shown in FIG. 1, FIG. 9, and FIG. 10 for the first embodiment 1001 and in FIGS. 11-13 for the second embodiment 1002, the magnet-assisted suture grasper 100 comprises a suture retrieval needle 102 comprising a proximal end 104, a distal end 106, and a needle body 108 extending therebetween. The needle body 108 defines a needle body axis 110 between the proximal end 104 and distal end 106 of the suture retrieval needle 102. The needle body 108 has a proximal hole 112, a distal hole 114, and a needle lumen 116 extending therebetween along the needle body axis 110.

As shown in FIG. 1, FIG. 9, and FIG. 10 for the first embodiment 1001 and in FIGS. 11-13 for the second embodiment 1002, the suture retrieval needle 102 can be a hypodermic needle. For example, the suture retrieval needle 102 can be an introducer needle designed for introducing guide wires into a vessel, applied here as the suture retrieval needle 102. Also for example, the suture retrieval needle 102 can be a 24-gauge needle, a 21-gauge needle, an 18-gauge needle, a 17-gauge needle, a 16-gauge needle, or a 14 gauge needle.

Accordingly, in some embodiments, the suture retrieval needle 102 is a hypodermic needle. In some embodiments, the suture retrieval needle 102 is an introducer needle. In some embodiments, the suture retrieval needle 102 is a 24-gauge needle, a 21-gauge needle, an 18-gauge needle, a 17-gauge needle, a 16-gauge needle, or a 14 gauge needle.

As shown in FIG. 1, FIG. 9, and FIG. 10 for the first embodiment 1001 and in FIGS. 11-13 for the second embodiment 1002, in some embodiments the suture retrieval needle 102 is straight. In accordance with these embodiments, the needle body axis 110 thereby is straight. Alternatively, in some embodiments, the suture retrieval needle 102 is curved. In accordance with these embodiments, the needle body axis 110 thereby is curved. In some embodiments, one or more portions of the suture retrieval needle 102 can be straight, and one or more portions can be curved. For example, in some embodiments, the suture retrieval needle 102 includes a curve at or near its distal end 106 but otherwise is straight. In accordance with these embodiments, the needle body axis 110 also includes a curve at or near the distal end 106 of the suture retrieval needle 102, but otherwise is straight.

As shown in FIG. 9 for the first embodiment 1001 and in FIG. 11 for the second embodiment 1002, in some embodiments the suture retrieval needle 102 has a sharp tip 118. This can be advantageous for piercing tissue during insertion of the suture retrieval needle 102 into a patient.

As shown in FIG. 1 for the first embodiment 1001 and in FIG. 11 for the second embodiment 1002, in some embodiments the suture retrieval needle 102 further comprises a hub 119. The hub 119 can have an open lumen.

Figure 35:
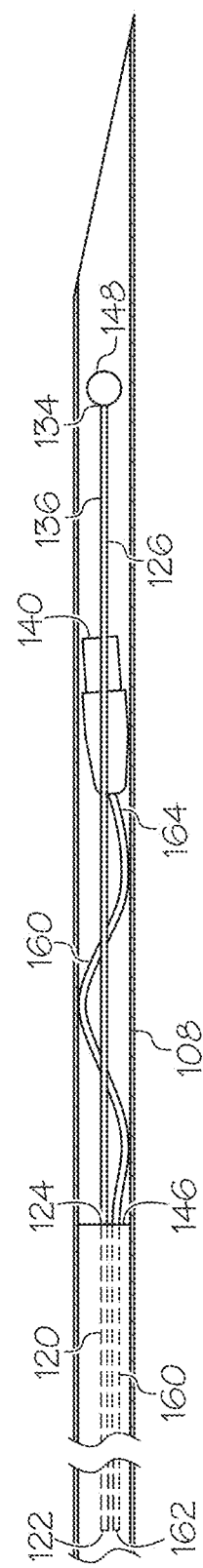
FIG. 35 is a side view of the distal end of the magnet-assisted suture grasper of FIG. 11, in which the advancer assembly is in the unlocked retracted position and the grasper arm is in the first position.

As shown in FIG. 1 and FIG. 5 for the first embodiment 1001 and in FIG. 35 for the second embodiment 1002, the magnet-assisted suture grasper 100 also comprises a retriever body 146. The retriever body 146 is disposed within the needle lumen 116 and translatable therein along the needle body axis 110. The retriever body 146 can be made from a polymer, such as nylon, polyether ether ketone, polycarbonate, or acrylonitrile butadiene styrene, or a metal, such as stainless steel or Nitinol.

Figure 48:
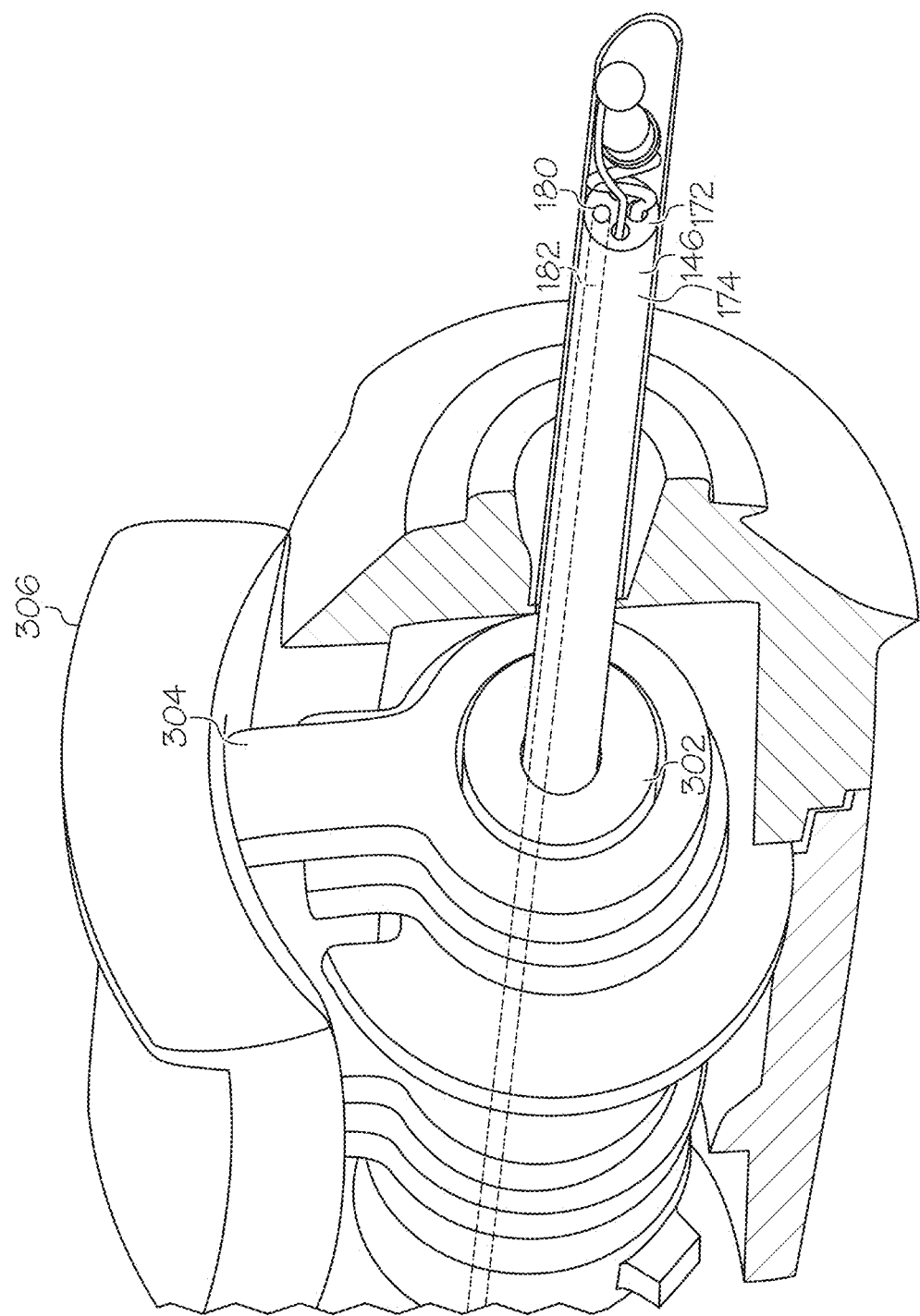
FIG. 48 is a partial sectional view of a subset of parts of the magnet-assisted suture grasper of FIG. 11, in which the advancer assembly is in the locked intermediate position and the grasper arm is in a position intermediate between the first position and the second position.
Figure 49A:
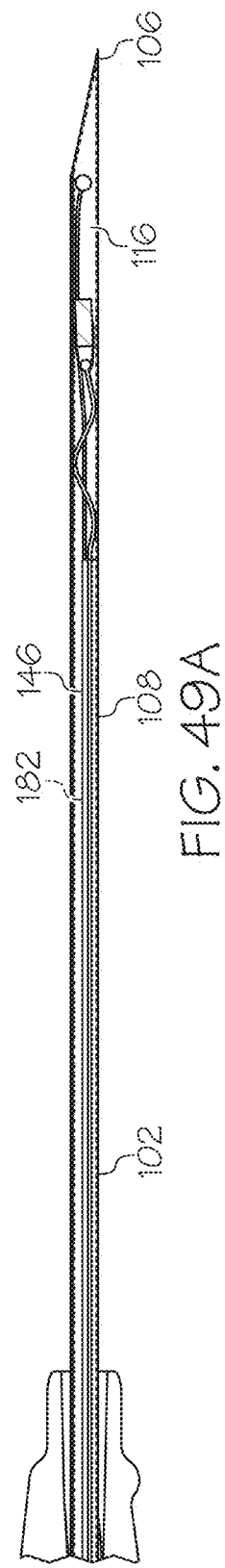
FIG. 49A-C is a sectional view of the magnet-assisted suture grasper of FIG. 11, in which the advancer assembly is in the locked intermediate position and the grasper arm is in a position intermediate between the first position and the second position.
Figure 49B:
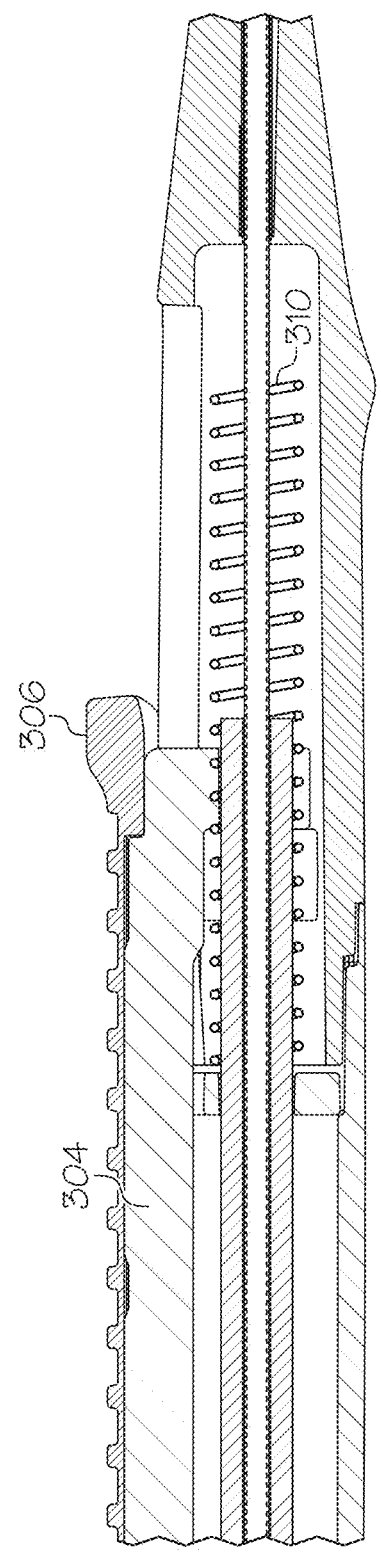
Figure 49C:
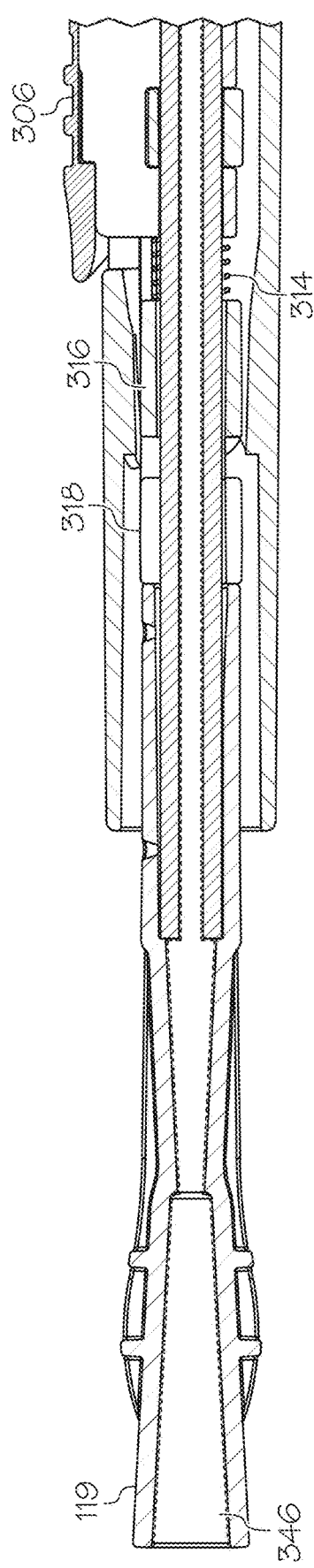

As shown in FIG. 5 for the first embodiment 1001 and in FIG. 48 for the second embodiment 1002, in some embodiments, the retriever body 146 comprises a proximal end 170, a distal end 172, and a retriever tube 174 extending therebetween. In these embodiments, the retriever tube 174 defines a retriever tube axis 176 between the proximal end 170 and distal end 172 of the retriever body 146, the retriever tube 174 has a proximal hole 178, a distal hole 180, and a retriever tube lumen 182 extending therebetween along the retriever tube axis 176. In these embodiments, the proximal hole 178 of the retriever tube 174 is in fluid communication with the distal hole 114 of the needle body 108 through the retriever tube lumen 182 and the needle lumen 116. In these embodiments, the retriever body 146 preferably is made from a polymer such as nylon to facilitate making the retriever body 146 including the retriever tube lumen 182.

This can be advantageous by allowing recovery of liquids and/or gasses from a surgical site of a patient and/or delivery of contrast agents to the surgical site through the retriever tube lumen 182 of the retriever body 146. Providing the ability to exchange fluids through the retriever body 146 and thus through the magnet-assisted suture grasper 100 broadens the applicability of the magnet-assisted suture grasper 100 for use with interventional techniques that employ fluid exchange to confirm the intracorporeal position of the distal end 106 of the suture retrieval needle 102 of the magnet-assisted suture grasper 100. For example, a need exists within the field of interventional radiology for the ability to confirm the location of cannulas inside the gastric lumens of patients during gastropexy. With the magnet-assisted suture grasper 100 comprising the retriever body 146 comprising the retriever tube lumen 182, following introduction of the suture retrieval needle 102 into a patient, aspiration of a small amount of stomach juice or air can be used to confirm the intraluminal position of the distal end 106 of the suture retrieval needle 102. Alternatively, a small amount of liquid radiographic contrast agent can be injected through the retriever tube lumen 182 of the retriever body 146 into the gastric lumen of the patient, allowing the intraluminal position to be confirmed through radiographic imaging.

Also in some embodiments the retriever body 146 can be transparent. This allows for the use of photo-initiated adhesives, which can be advantageous for assembly of components. Photo-initiated adhesives provide more open time for component positioning, while requiring minimal fixture time due to a very rapid cure profile.

Figure 50:
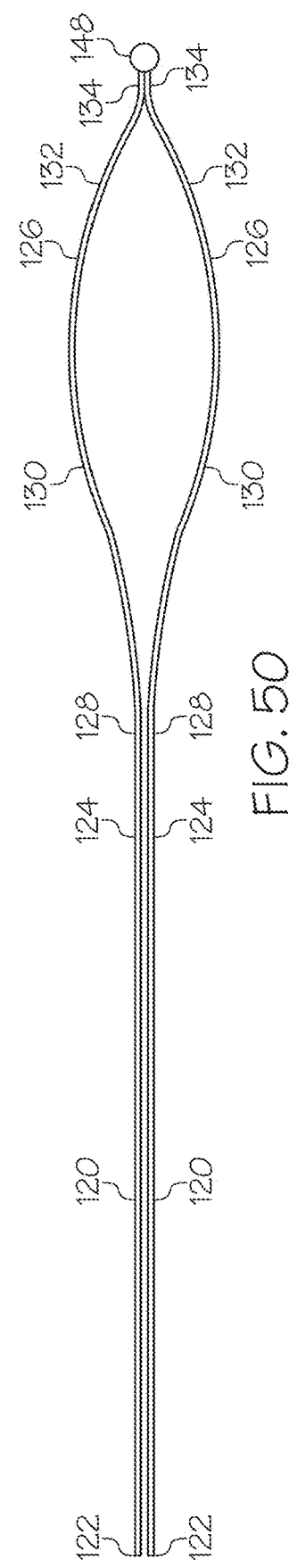
FIG. 50 is a top view of the grasper arm of the magnet-assisted suture grasper of FIG. 11, in which the grasper arm is in the second position.
Figure 51:
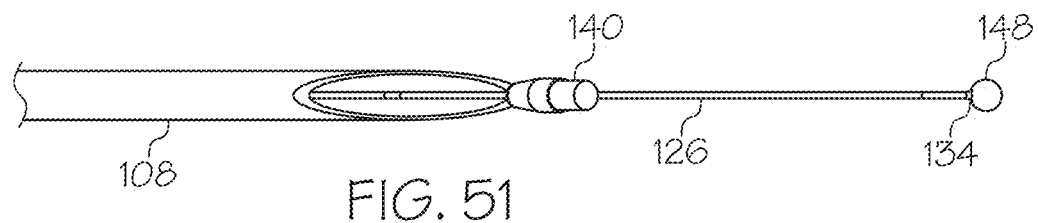
FIG. 51 is a side view of a first alternate embodiment of a grasper arm of a magnet-assisted suture grasper as disclosed herein.

As shown in FIG. 2 for the first embodiment 1001 and in FIG. 33 and FIG. 35 for the second embodiment 1002, with reference to FIG. 50 for both the first embodiment 1001 and the second embodiment 1002, the magnet-assisted suture grasper 100 also comprises a grasper wire 120 having a proximal end 122 and a distal end 124.

The grasper wire 120 is fixedly disposed within the retriever body 146. This can be accomplished by inserting the proximal end 122 of the grasper wire 120 into the retriever body 146 and securing the grasper wire 120 to the retriever body 146 so that it is translationally and rotationally fixed to the retriever body 146. The preferred method of assembly is to insert the grasper wire 120 into a lumen of the retriever body 146 and apply an adhesive to join the grasper wire 120 to the retriever body 146. However, other means of attachment are also suitable, and may be preferable based on size, shape, or application. Such other means include mechanical means, e.g., swaged, interference fit, or pinned, or other means, such as brazing, welding, soldering, etc.

The grasper wire 120 can be, for example, a metal wire, such as a Nitinol wire or a stainless steel wire, or a plastic wire, among other types of wire. The grasper wire 120 can be formed, for example, as a solid wire, a stranded wire, or a braided wire. The grasper wire 120 can have a shape, for example, based on being a shaped wire and/or a stamped wire. The grasper wire 120 can comprise, for example, one or more wires joined together at one or more common points, for example, by welding, soldering, braiding, crimping, adhesive, or other means.

Figures 14, 15, 16, 17:
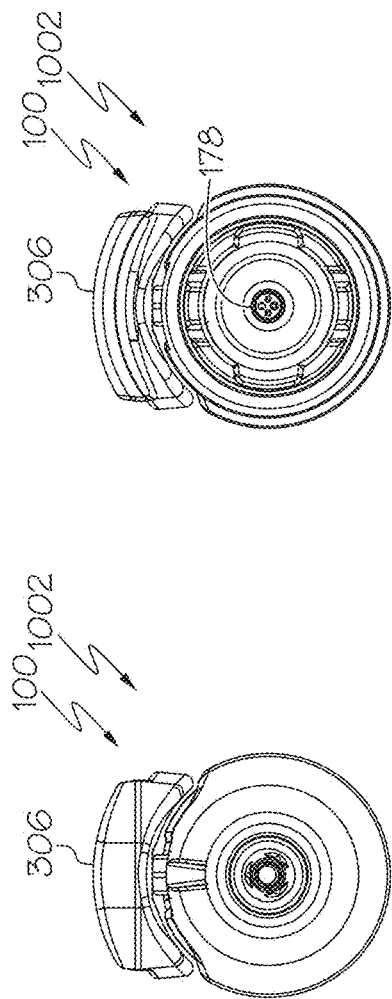
FIG. 14 is a front view of the magnet-assisted suture grasper of FIG. 11, in which the grasper arm is in the first position.
FIG. 15 is a back view of the magnet-assisted suture grasper of FIG. 11, in which the grasper arm is in the first position.
FIG. 16 is a side view of the magnet-assisted suture grasper of FIG. 11, in which the grasper arm is in the second position.
FIG. 17 is a top view of the magnet-assisted suture grasper of FIG. 11, in which the grasper arm is in the second position.
Figure 18:
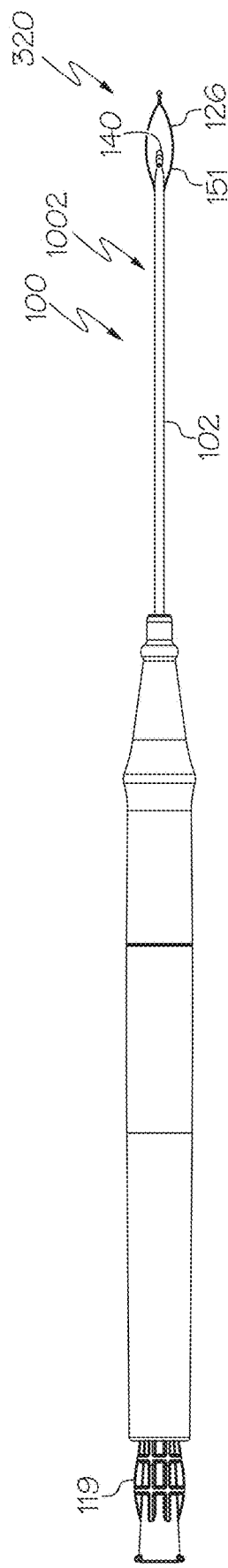
FIG. 18 is a bottom view of the magnet-assisted suture grasper of FIG. 11, in which the grasper arm is in the second position.
Figure 19:
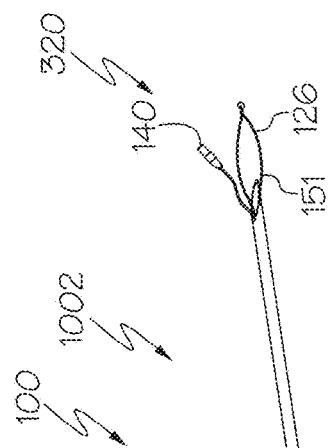
FIG. 19 is a front view of the magnet-assisted suture grasper of FIG. 11, in which the grasper arm is in the second position.
Figure 20:
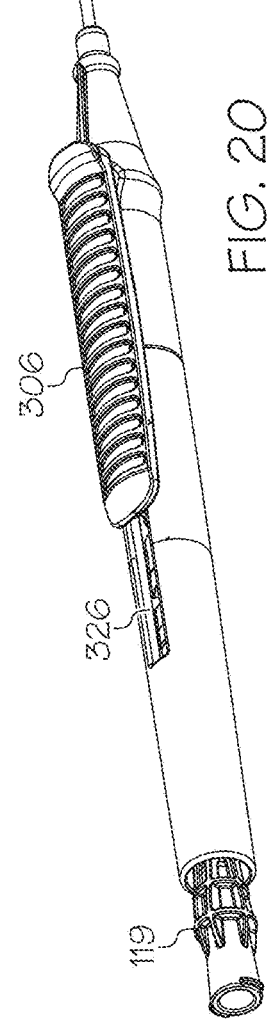
FIG. 20 a perspective view of the magnet-assisted suture grasper of FIG. 11, in which the grasper arm is in the second position.
Figure 22:
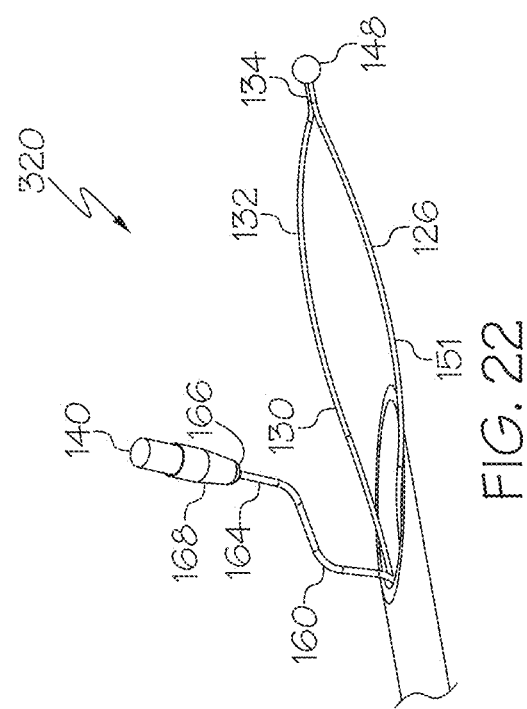
FIG. 22 is an expanded perspective view of the distal end of the magnet-assisted suture grasper of FIG. 11, in which the grasper arm is in the second position.
Figure 23:
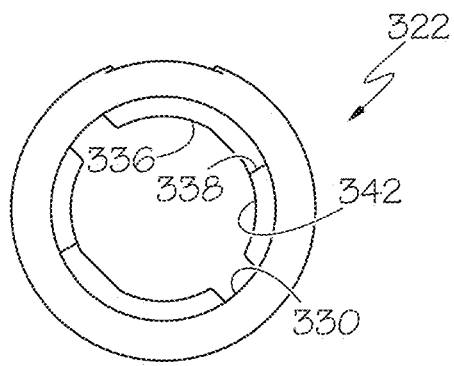
FIG. 23 is a proximal end view of a barrel of the magnet-assisted suture grasper of FIG. 11.
Figure 24:
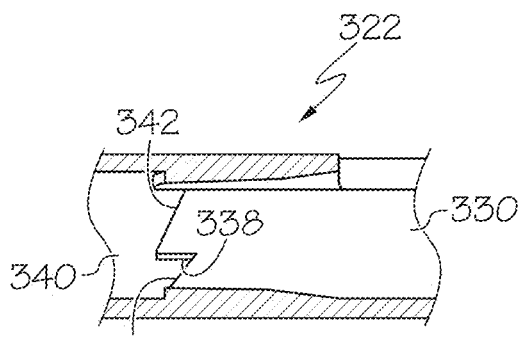
FIG. 24 is a partial longitudinal view of the barrel of FIG. 23.
Figure 25:
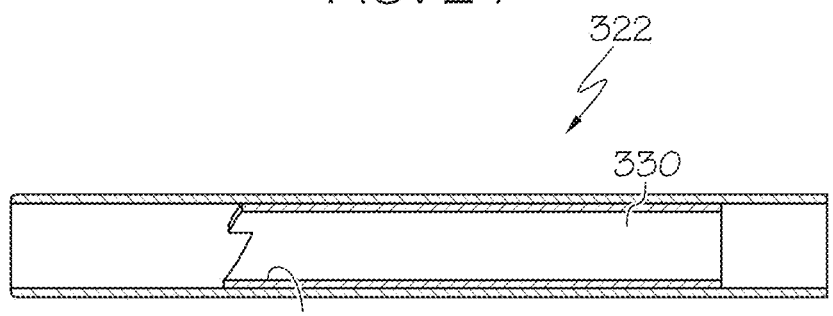
FIG. 25 is a partial sectional view of the barrel of FIG. 23 through guide channels of the barrel.
Figure 26:
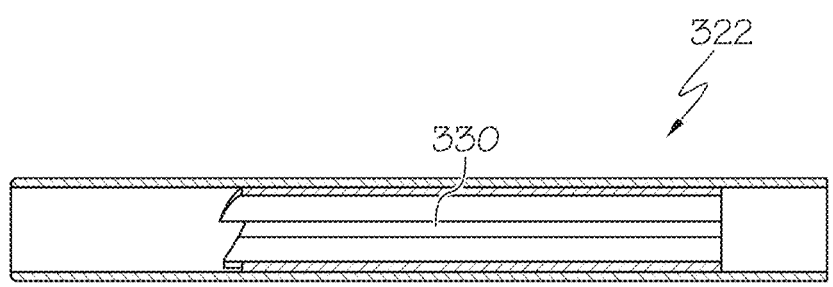
FIG. 26 is a partial sectional view of the barrel of FIG. 23 perpendicular to guide channels of the barrel.
Figure 27:
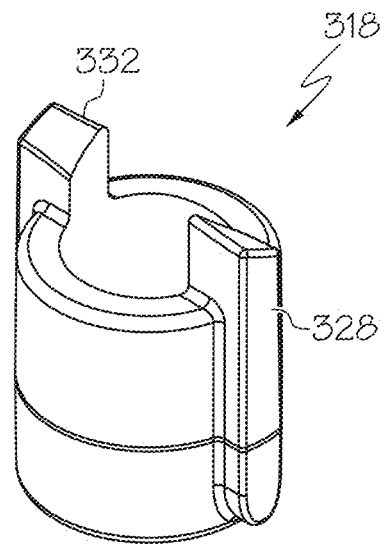
FIG. 27 is a perspective view of a lock cam of the magnet-assisted suture grasper of FIG. 11.
Figure 28:
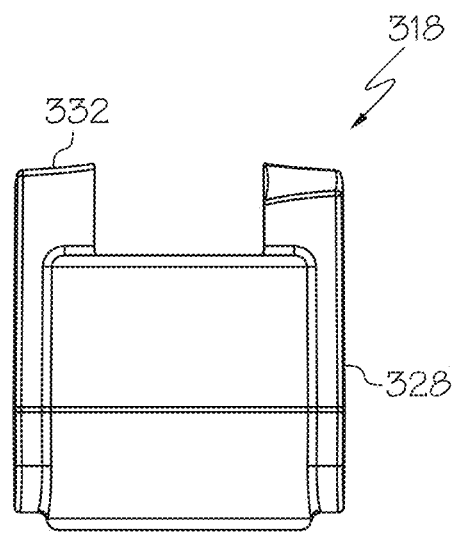
FIG. 28 is a side view of the lock cam of FIG. 27.
Figure 29:
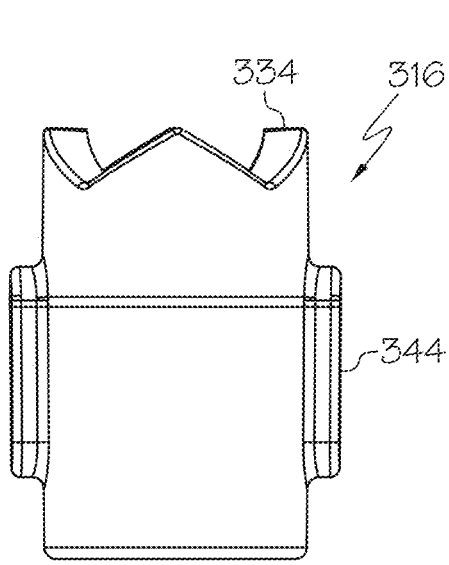
FIG. 29 is a side view of a drive cam of the magnet-assisted suture grasper of FIG. 11.
Figure 30:
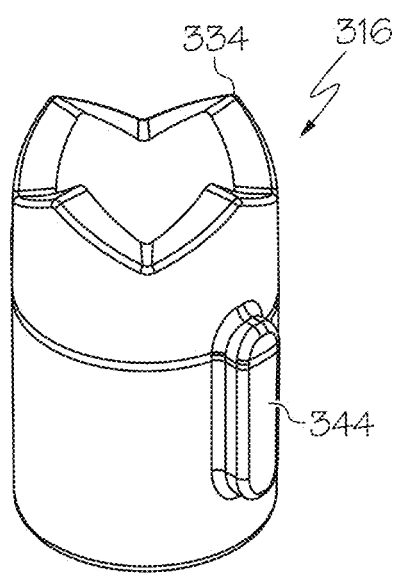
FIG. 30 is a perspective view of the drive cam of FIG. 29.
Figure 34:
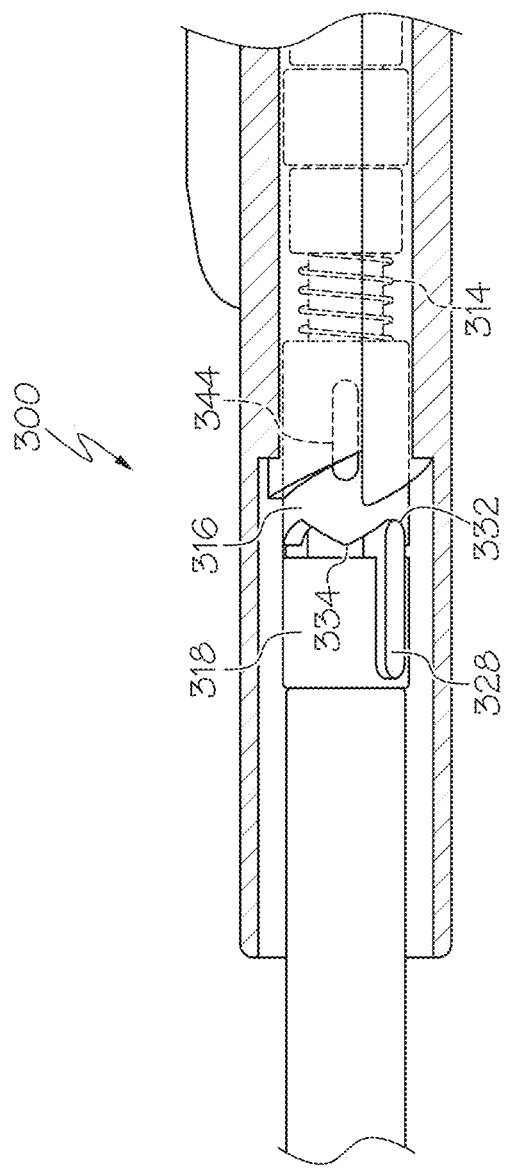
FIG. 34 is a partial sectional view of a subset of components of the advancer assembly of the magnet-assisted suture grasper of FIG. 11, in which the advancer assembly is in the unlocked retracted position.

As shown in FIG. 1, FIG. 2, and FIGS. 5-8 for the first embodiment 1001 and in FIG. 16 and FIG. 22 for the second embodiment 1002, with reference to FIG. 50 for both the first embodiment 1001 and the second embodiment 1002, the magnet-assisted suture grasper 100 also comprises a grasper arm 126 comprising a proximal end 128, a proximal-to-intermediate portion 130, a distal portion 132, and a distal end 134. Like the grasper wire 120, the grasper arm 126 also can be, for example, a wire, although other structures, such as a tube or other elongated member can be suitable too. Regarding the grasper arm 126 being a wire, the grasper arm 126 can be, for example, a metal wire, such as a Nitinol wire or a stainless steel wire, or a plastic wire, and can be formed, for example, as a solid wire, a stranded wire, or a braided wire, and can have a shape, for example, based on being a shaped wire and/or a stamped wire, and can comprise, for example, one or more wires joined together at one or more common points, for example, by welding, soldering, braiding, crimping, adhesive, or other means.

As shown in FIG. 1 and FIG. 2 for the first embodiment 1001 and in FIG. 16 and FIG. 35 for the second embodiment 1002, the grasper arm 126 extends from the distal end 124 of the grasper wire 120 and is reversibly moveable between a first position 136 and a second position 138.

As shown for in FIG. 50 for both the first embodiment 1001 and the second embodiment 1002, the grasper arm 126 can extend from the distal end 124 of the grasper wire 120, among other ways, based on the grasper arm 126 being integral to the grasper wire 120. By this it is meant that the grasper arm 126 and the grasper wire 120 can be adjacent portions of a single segment of wire, e.g., a solid, stranded, or braided wire segment from which the grasper wire 120 and the grasper arm 126 have been formed. In such examples the grasper arm 126 extends from the distal end 124 of the grasper wire 120 based on the grasper arm 126 and the grasper wire 120 forming a continuous wire segment through the distal end 124 of the grasper wire 120.

Also for example, the grasper arm 126 can extend from the distal end 124 of the grasper wire 120 directly, based on adhesion or other direct attachment of the grasper arm 126 to the grasper wire 120. In these examples the grasper arm 126 can extend from the distal end 124 of the grasper wire 120 based on the grasper arm 126 and the grasper wire 120 forming wire segments connected at the distal end 124 of the grasper wire 120 by adhesion or other direct attachment.

Also for example, the grasper arm 126 can extend from the distal end 124 of the grasper wire 120 indirectly, based on attachment through one, two, or more intermediate parts, such as a ferrule, a ring, or a sleeve, among other intermediate parts. In these examples the grasper arm 126 can extend from the distal end 124 of the grasper wire 120 based on the grasper arm 126 and the grasper wire 120 forming wire segments connected at the distal end 124 of the grasper wire 120 via intermediate parts.

As shown in FIG. 1 and FIGS. 5-8 for the first embodiment 1001 and in FIG. 16, FIG. 17, FIG. 22, and FIG. 35 for the second embodiment 1002, the magnet-assisted suture grasper 100 also comprises a grasper magnet 140 disposed adjacent the proximal-to-intermediate portion 130 of the grasper arm 126. The magnet-assisted suture grasper 100 sequesters the grasper magnet 140 within the needle lumen 116 when the grasper arm 126 is in the first position 136 and exposes the grasper magnet 140 from the needle lumen 116 when the at least grasper arm 126 is in the second position 138. The grasper magnet 140 can be, for example, a permanent dipole magnet.

Figure 7:
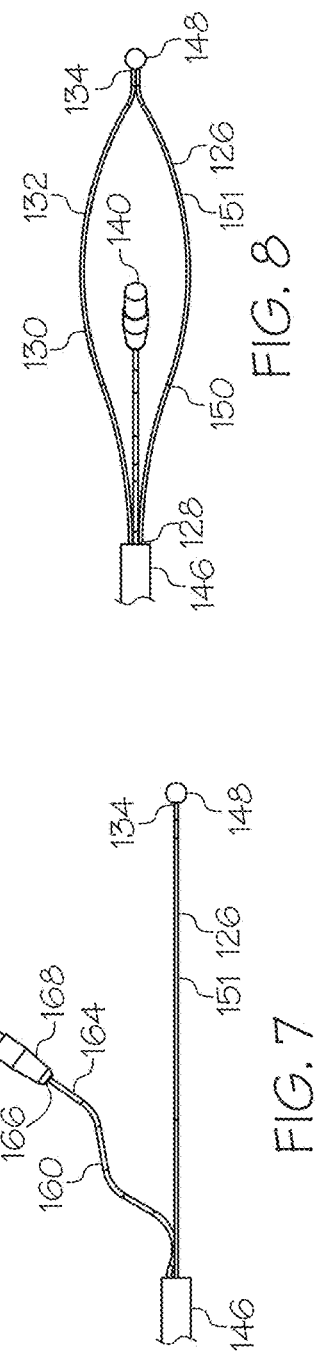
FIG. 7 is an expanded side view of a distal end of the portion of the magnet-assisted suture grasper of FIG. 5, in which the grasper arm is in the second position.

As shown in FIG. 2 and FIG. 7 for the first embodiment 1001 and in FIG. 16, FIG. 22, and FIG. 35 for the second embodiment 1002, in some embodiments the magnet-assisted suture grasper 100 further comprises a magnet wire 160 having a proximal end 162 and a distal end 164, wherein the proximal end 162 of the magnet wire 160 is fixedly disposed within the retriever body 146 and the grasper magnet 140 is fixedly attached to the distal end 164 of the magnet wire 160, either directly, e.g., based on adhesion or other direct attachment, or indirectly, e.g., based on attachment through one or more intermediate parts, such as a ferrule, ring, or sleeve, among other intermediate parts. In accordance with these embodiments, translation of the retriever body 146 also results in translation of the magnet wire 160, and thus also the grasper magnet 140.

The magnet wire 160 can be fixedly disposed within the retriever body 146 by inserting the proximal end 162 of the magnet wire 160 into the retriever body 146 and securing the magnet wire 160 to the retriever body 146 so that the magnet wire 160 is translationally and rotationally fixed to the retriever body 146. Like for the grasper wire 120, the preferred method of assembly is to insert the magnet wire 160 into a lumen of the retriever body 146 and apply an adhesive to join the magnet wire 160 to the retriever body 146, but other means of attachment are also suitable.

As shown in FIG. 7 for the first embodiment 1001 and in FIG. 22 for the second embodiment 1002, in some of these embodiments the magnet wire 160 further comprises a magnet wire distal terminus 166 at the distal end 164 of the magnet wire 160, the magnet-assisted suture grasper 100 further comprises a ferrule 168 attached to the magnet wire distal terminus 166 at the distal end 164 of the magnet wire 160, and the grasper magnet 140 is attached to the ferrule 168.

The magnet wire 160 can be, for example, a metal wire, such as a Nitinol wire or a stainless steel wire, or a plastic wire, and can be formed, for example, as a solid wire, a stranded wire, or a braided wire, and can have a shape, for example, based on being a shaped wire and/or a stamped wire, and can comprise, for example, one or more wires joined together at one or more common points, for example, by welding, soldering, braiding, crimping, adhesive, or other means.

Considering attachment of the grasper magnet 140 to the magnet wire 160 in more detail, the grasper magnet 140 can be attached to the magnet wire 160, for example, similarly as described in U.S. Pub. No. 2021/0059667 for attachment of a magnet to a suture. This can be accomplished as follows. The grasper magnet 140 can be attached to a ferrule 168, which is attached to a magnet wire 160 having an enlarged magnet wire distal terminus 166. With reference to U.S. Pub. No. 2021/0059667, the enlarged magnet wire distal terminus 166 would replace the knot tied in a suture. A ball end is the preferred shape for the magnet wire distal terminus 166 and a mono-filament with a round cross-section is the preferred shape of the magnet wire 160. However, as long as the magnet wire 160 and the magnet wire distal terminus 166 are sized appropriately, other constructions and final shapes would also be suitable. The magnet wire distal terminus 166 may be formed into any shape, e.g., cubic, cylindrical, pyramidal, organic, etc., and the magnet wire 160 may be of any cross sectional shape, e.g., square, rectangular, cruciform, etc., and may be of mono- or multi-filament construction.

The magnet wire 160 must be sized small enough to fit through the small opening of the ferrule 168, while the magnet wire distal terminus 166 must be sized larger than the small opening of the ferrule 168 and smaller than the large opening of the ferrule 168. The magnet wire distal terminus 166 may be integrated into the magnet wire 160, e.g., the magnet wire distal terminus 166 can be melt formed, coined, bent, etc., or it may be a separate component. If a separate component, it may be attached by mechanical means, e.g., swaged, threaded, interference fit, pinned, etc., by adhesive means, or by other means, e.g., welding, soldering, brazing, etc.

To assemble the grasper magnet 140, the ferrule 168, and the magnet wire 160, the magnet wire 160 is first passed through the ferrule 168 from its distal end 164 to its proximal end 162, so that the magnet wire distal terminus 166 becomes positioned inside the ferrule 168. The grasper magnet 140 is then installed from the distal end, and attached to the ferrule 168. The grasper magnet 140 can be attached by mechanical means, e.g., swaged, threaded, interference fit, pinned, etc., or adhesive means or other means, e.g., welding, brazing, etc. Once the grasper magnet 140 is attached, the magnet wire distal terminus 166 is permanently captured between the grasper magnet 140 and the ferrule 168, and the sub-assembly is complete.

As shown in FIG. 2 and FIG. 7 for the first embodiment 1001 and in FIG. 16, FIG. 22, and FIG. 35 for the second embodiment 1002, in some embodiments of the magnet-assisted suture grasper 100 that further comprises a magnet wire 160 to which the grasper magnet 140 is fixedly attached as described, the grasper magnet 140 is displaced radially from the needle body axis 110 when the grasper arm 126 is in the second position 138. This can be advantageous by providing an operator of the magnet-assisted suture grasper 100 an additional range of motion to move the grasper magnet 140 within a site of a patient by rotation of the magnet-assisted suture grasper 100 and thus greater versatility in positioning the grasper magnet 140 relative to a magnetic suture 200 in the site.

Figure 8:
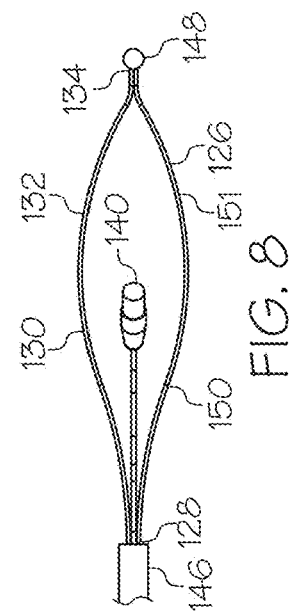
FIG. 8 is an expanded top view of a distal end of the portion of the magnet-assisted suture grasper of FIG. 5, in which the grasper arm is in the second position.

Alternatively or additionally, in some embodiments the grasper magnet 140 is fixedly attached to the grasper wire 120 and/or the grasper arm 126, again either directly, e.g., based on adhesion or other direct attachment, or indirectly, e.g., based on attachment through one or more intermediate parts, such as a ferrule, ring, or sleeve, among other intermediate parts. This can be advantageous by allowing for use of a shorter grasper arm 126 relative to embodiments in which the grasper magnet 140 is fixedly attached to a grasper wire 120. As shown in FIG. 7 and FIG. 8 for the first embodiment 1001 and in FIG. 22 and FIG. 35 for the second embodiment 1002, the distal end 134 of the grasper arm 126 extends further distally than the grasper magnet 140. This means that when the grasper arm 126 is in the first position 136 that the distal end 134 of the grasper arm 126 extends further distally within the needle lumen 116 than does any portion of the grasper magnet 140. This also means that when the grasper arm 126 is in the second position 138 that the distal end 134 of the grasper arm 126 extends further distally from the suture retrieval needle 102 than does any portion of the grasper magnet 140. This also means that when the grasper arm 126 is in the second position 138 that the grasper magnet 140 is closer to the distal end 106 of the suture retrieval needle 102 than is the distal end 134 of the grasper arm 126.

Figure 45:
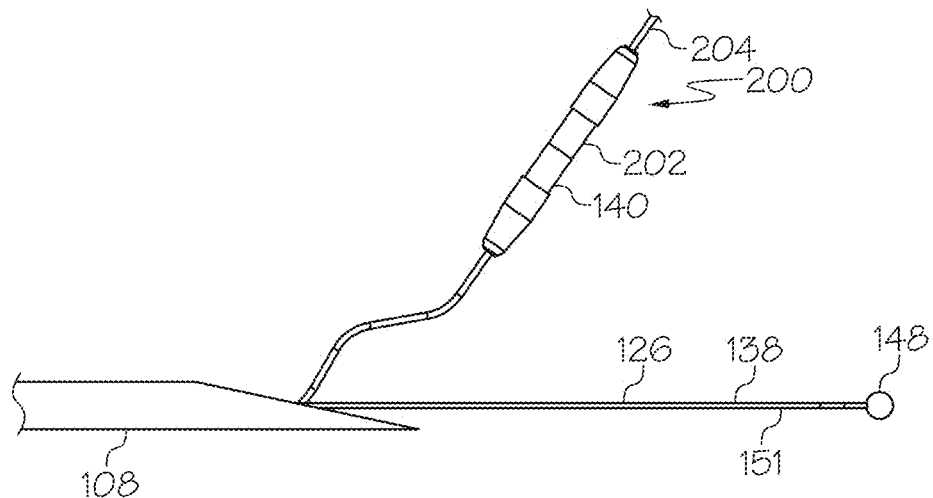
FIG. 45 is a side view of the distal end of the magnet-assisted suture grasper of FIG. 1, in which the grasper arm is in the second position and the grasper magnet is attracting a magnetic suture and in contact with the magnetic suture. This also is a side view of the distal end of the magnet-assisted suture grasper of FIG. 11, in which the advancer assembly is in the locked extended position, the grasper arm is in the second position, and the grasper magnet is attracting a magnetic suture and in contact with the magnetic suture.

As shown by comparison of FIG. 2 with FIG. 1 for the first embodiment 1001 and by comparison of FIG. 35 with FIG. 16 for the second embodiment 1002, and with reference to FIG. 9 for the first embodiment 1001, FIG. 11 for the second embodiment 1002, and FIGS. 43-45 for both, translation of the retriever body 146 within the needle lumen 116 in a first direction along the needle body axis 110 causes the grasper arm 126 to move from the first position 136 to the second position 138, thereby exposing the grasper magnet 140 and allowing contact between the grasper magnet 140 and a magnetic suture 200 attracted thereto. The translation of the retriever body 146 results in translation of the grasper wire 120 and thus translation of the grasper arm 126. The translation of the retriever body 146 in the first direction can be translation of the retriever body 146 within the needle lumen 116 in a direction from the proximal end 104 of the suture retrieval needle 102 toward the distal end 106 of the suture retrieval needle 102. When the grasper arm 126 is in the first position 136 the grasper magnet 140 can be disposed entirely inside the needle lumen 116, and thus sequestered within the needle lumen 116. In accordance with these embodiments, such translation of the retriever body 146 within the needle lumen 116 in the first direction can move the grasper magnet 140 from inside the needle lumen 116 to outside the needle lumen 116, thus exposing the grasper magnet 140.

The grasper arm 126 can be sufficiently stiff so that translation of the retriever body 146 within the needle lumen 116 in the first direction moves the grasper arm 126 from inside the needle lumen 116 to outside the needle lumen 116, thus exposing the grasper magnet 140. This may be accomplished by making the grasper arm 126 sufficiently stiff so as to moveable by translation of retriever body 146.

Figure 46:
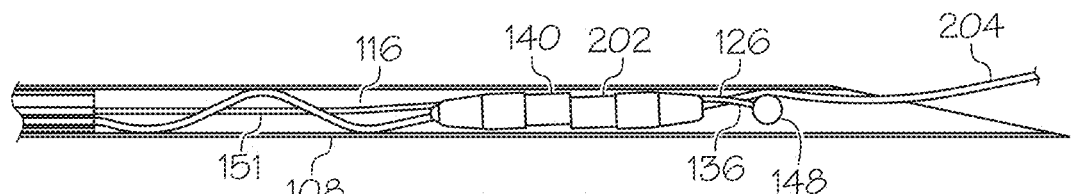
FIG. 46 is a sectional view of the distal end of the magnet-assisted suture grasper of FIG. 1, in which the grasper arm is in the first position, and the grasper magnet is attracting a magnetic suture and in contact with the magnetic suture, such that the magnetic suture has been captured within the needle lumen of the suture retrieval needle of the magnet-assisted suture grasper. This also is a sectional view of the distal end of the magnet-assisted suture grasper of FIG. 11, in which the advancer assembly is in the unlocked retracted position, the grasper arm is in the first position, and the grasper magnet is attracting a magnetic suture and in contact with the magnetic suture, such that the magnetic suture has been captured within the needle lumen of the suture retrieval needle of the magnet-assisted suture grasper.

As shown by comparison of FIG. 1 with FIG. 2 for the first embodiment 1001 and by comparison of FIG. 16 with FIG. 35 for the second embodiment 1002, and with reference to FIG. 9 for the first embodiment 1001, FIG. 11 for the second embodiment 1002, and FIG. 45 and FIG. 46 for both, translation of the retriever body 146 within the needle lumen 116 in a second direction opposite the first direction along the needle body axis 110 causes the grasper arm 126 to move from the second position 138 to the first position 136, thereby sequestering the grasper magnet 140 and grasping the magnetic suture 200 within the needle lumen 116. The translation of the retriever body 146 in the second direction can be translation of the retriever body 146 within the needle lumen 116 in a direction from the distal end 106 of suture retrieval needle 102 toward the proximal end 104 of the suture retrieval needle 102. Such translation of the retriever body 146 within the needle lumen 116 in the second direction can move the grasper magnet 140 from outside the needle lumen 116 to inside the needle lumen 116, thus sequestering the grasper magnet 140 again and grasping the magnetic suture 200 within the needle lumen 116.

This can be accomplished as follows. Because the grasper magnet 140 is closer to the distal end 106 of the suture retrieval needle 102 than is the distal end 134 of the grasper arm 126 while the grasper arm 126 is in the second position 138, when a suture magnet 202 of a magnetic suture 200 contacts the grasper magnet 140 and the retriever body 146 is translated in the second direction to the first position 136, the grasper magnet 140 and the suture magnet 202 of the magnetic suture 200 enter the needle lumen 116 before the distal end 134 of the grasper arm 126 does. Once the distal end 134 of the grasper arm 126 has followed the suture magnet 202 into the needle lumen 116, the suture magnet 202 cannot exit the needle lumen 116 while the distal end 134 of the grasper arm 126 remains in the needle lumen 116. The grasper arm 126 blocks exit of the suture magnet 202, thereby mechanically capturing the magnetic suture 200. The suture magnet 202 of the magnetic suture 200 thus can be grasped by the grasper arm 126 as the magnet-assisted suture grasper 100 is used to pull the magnetic suture 200 through soft tissue of a patient. The grasper wire 120 and the grasper arm 126 are sufficiently strong to resist the frictional drag that results from pulling the magnetic suture 200 through the soft tissue.

As noted above, the grasper arm 126 comprises a proximal end 128, a proximal-to-intermediate portion 130, a distal portion 132, and a distal end 134. Also as noted, the grasper magnet 140 is disposed adjacent the proximal-to-intermediate portion 130 of the grasper arm 126. The distal portion 132 of the grasper arm 126 has a length and orientation sufficient to allow the suture magnet 202 of a magnetic suture 200 to fit between the grasper magnet 140 and the distal end 134 of the grasper arm 126 when the grasper arm 126 is in the second position 138, so that the suture magnet 202 of the magnetic suture 200 can contact the grasper magnet 140 for magnetic attraction, and when the grasper arm 126 has been returned to the first position 136, so that the suture magnet 202 of the magnetic suture 200 can fit within the needle lumen 116 along with the grasper magnet 140 and the grasper arm 126 for mechanical capture. The proximal-to-intermediate portion 130 of the grasper arm 126 adjacent to which the grasper magnet 140 is disposed can be any portion of the grasper arm 126 distal to the proximal end 128 and proximal to the distal portion 132, so long as sufficient space is provided for a suture magnet 202 to fit between the grasper magnet 140 and the distal end 134 of the grasper arm 126.

In some embodiments, the retriever body 146 and the grasper wire 120 are more flexible than the needle body 108. This can be advantageous for suture retrieval needles 102 in which one or more portions of the suture retrieval needle 102 are curved, e.g., a suture retrieval needle 102 that includes a curve at or near its distal end 106 but otherwise is straight. Then the retriever body 146 and the grasper wire 120 are preferentially made of a polymeric material, or a metal with a high proportional limit, such as Nitinol, to allow the retriever body 146 and the grasper wire 120 to elastically deform around the curve of the suture retrieval needle 102.

As noted above, the grasper arm 126 extends from the distal end 124 of the grasper wire 120. For a grasper arm 126 that is integral to a grasper wire 120, the distal end 124 of the grasper wire 120 is the portion of the grasper wire 120 adjacent the distal end 172 of the retriever body 146, and the grasper arm 126 begins and extends distally from this distal end 124 of the grasper wire 120. For a grasper arm 126 that otherwise extends from the distal end 124 of the grasper wire 120 based on attachment that is direct or indirect, the distal end 124 of the grasper wire 120 is the part of the grasper wire 120 at which the grasper arm 126 is attached.

As shown in FIG. 1 and FIGS. 5-8 for the first embodiment 1001 and in FIG. 16 and FIG. 22 for the second embodiment 1002, and with reference to FIG. 50 for both, the magnet-assisted suture grasper 100 can include a first grasper arm 126 that is integrally attached to a first grasper wire 120 and a second grasper arm 126 that is integrally attached to a second grasper wire 120, with the first and second grasper arms 126 being connected at their distal ends 134, thereby forming a grasper arm loop 150. Also as shown, the first and second grasper arms 126 can comprise an enlarged distal terminus 148 at their distal ends 134.

This configuration, termed a trap wire 151, is thus formed from two free ends of wire which meet at a single point at the distal end, i.e., first and second grasper arms 126 extending from first and second grasper wires 120, respectively, and connected at their distal ends 134, at which point a large spheroid feature, i.e., an enlarged distal terminus 148, is located.

The enlarged distal terminus 148 is sized to allow contact between the grasper magnet 140 and a suture magnet 202 of a magnetic suture 200 attracted thereto when the grasper arm loop 150 is in the second position 138 outside the needle lumen 116. The enlarged distal terminus 148 also is sized such that when the grasper arm loop 150 is in the first position 136 inside the needle lumen 116, a suture 204 of the magnetic suture 200 can pass by the enlarged distal terminus 148, but the suture magnet 202 of the magnetic suture 200 cannot. For example, for a magnet-assisted suture grasper 100 that includes an extra-thin-wall 17 gauge suture retrieval needle 102, having a nominal inner diameter of 0.050 inches (1.27 mm) and a loop of 3-0 suture, having a mean diameter of 0.0079 to 0.0098 inches (0.20 to 0.25 mm), with a magnetic ferrule having a major outer diameter of 0.040 inches (1.0 mm), the preferred size for this spheroid member is between 0.016 to 0.040 inches (0.41 to 1.0 mm), nominally. More generally, the enlarged distal terminus 148 can have a size corresponding to about 10% to about 90% of the inner diameter of the needle lumen 116, preferably about 20% to about 80% of the inner diameter of the needle lumen 116, and more preferably about 30% to about 60% of the inner diameter of the needle lumen 116. For example, for an enlarged distal terminus 148 corresponding to a spheroid feature, the enlarged distal terminus 148 can have a diameter of about 10% to about 90%, about 20% to about 80%, or about 30% to about 60% of the inner diameter of the needle lumen 116. Also for example, for an enlarged distal terminus 148 corresponding to an alternative shape, the enlarged distal terminus 148 can have a width transverse to the needle body axis 110 of about 10% to about 90%, about 20% to about 80%, or about 30% to about 60% of the inner diameter of the needle lumen 116. An enlarged distal terminus 148 within this size range will generally be sufficiently small to allow contact between the grasper magnet 140 and a suture magnet 202 of a magnetic suture 200 attracted thereto when the grasper arm loop 150 is outside the needle lumen 116. An enlarged distal terminus 148 within this size range also will generally be sufficiently small to allow a suture 204 of a magnetic suture 200, even a suture 204 having a relatively large mean diameter, to pass by the enlarged distal terminus 148, and sufficiently large to prevent the suture magnet 202 of the magnetic suture 200, even a suture magnet 202 of a relatively small size, from passing by the enlarged distal terminus 148.

Additionally, in this configuration the two strands of wire of the grasper arm loop 150, i.e., the first grasper arm 126 that is integrally attached to the first grasper wire 120 and the second grasper arm 126 that is integrally attached to the second grasper wire 120, flare out before coming back together at the distal ends 134. This flare is sized so that the width measured across the outer diameter of the wires at this point exceeds the inner diameter of the suture retrieval needle 102. For example, for an extra-thin-wall 17 gauge suture retrieval needle 102, the flare is sized so that the width measured across the outer diameter of the wires is greater than 0.050 inches (greater than 1.27 mm). This creates an interference fit between the grasper arm loop 150 and the suture retrieval needle 102, which results in the wires being squeezed together as they are drawn into the needle lumen 116. The elastic deformation of the wires generates a reaction force which pushes back against the inner surface of the needle lumen 116. Because the inner surface of the needle lumen 116 is round, the translation of this force vector by the curved surface acts to push the wires towards the hemisphere of the needle lumen 116, i.e. the wires are disposed across a center line of the distal hole 114 of the needle body 108. This self-centering action helps prevent the spheroid feature from being caught in the crotch of distal hole 114 that is created by the bevel at the sharpened tip of the suture retrieval needle 102.

The grasper arm loop 150 can have a length and shape such that the grasper arm loop 150 circumscribes an area sufficiently large to allow contact between the grasper magnet 140 and a suture magnet 202 of a magnetic suture 200 attracted thereto when the grasper arm loop 150 is in the second position 138. For example, the grasper arm loop 150 can have a length and shape such that the corresponding circumscribed area is sufficiently large to fit both the grasper magnet 140 and the suture magnet 202 when the grasper magnet 140 and the suture magnet 202 are in contact at their respective poles.

The grasper arm loop 150 also can be sized such that the grasper arm loop 150 has a thickness, e.g., a mean diameter, sufficiently great to block the suture magnet 202 of the magnetic suture 200 from exiting the needle lumen 116 through the distal hole 114 of the suture retrieval needle 102 when the grasper arm loop 150 is in the first position 136. The grasper arm loop 150 can be thinner than the enlarged distal terminus 148 and still block a suture magnet 202 from exiting a needle lumen 116 based on the grasper arm loop 150 being disposed across a center line of the distal hole 114 of the needle body 108 due to an interference fit between the grasper arm loop 150 and the suture retrieval needle 102 as discussed above for the trap wire 151. Suitable thicknesses, e.g., mean diameters, for the grasper arm loop 150 otherwise can be determined similarly as for the enlarged distal terminus 148. For example, for a magnet-assisted suture grasper 100 that includes an extra-thin-wall 17 gauge suture retrieval needle 102, having a nominal inner diameter of 0.050 inches (1.27 mm) and a loop of 3-0 suture, having a mean diameter of 0.0079 to 0.0098 inches (0.20 to 0.25 mm), with a magnetic ferrule having a major outer diameter of 0.040 inches (1.0 mm), the preferred mean diameter for the wire is about 0.0060 inches (0.15 mm). More generally, the grasper arm loop 150 can have a mean diameter, for example, corresponding to about 0.5% to about 10% of the inner diameter of the needle lumen 116, preferably about 2% to about 4% of the inner diameter of the needle lumen 116, and more preferably about 2.3% to about 3.5% of the inner diameter of the needle lumen 116. A grasper arm loop 150 within this size range generally will have a thickness, e.g., a mean diameter, sufficiently great to block a suture magnet 202 of a magnetic suture 200 from exiting the needle lumen 116 through the distal hole 114 of the suture retrieval needle 102 when the grasper arm loop 150 is in the first position 136.

The preferred material for the first grasper arm 126 that is integrally attached to the first grasper wire 120 and the second grasper arm 126 that is integrally attached to the second grasper wire 120 is Nitinol. This is due to the pseudo-elastic nature of Nitinol, which allows wires made from Nitinol to recover their shape after relatively large deformations. The preferred method of manufacture is to hold the two corresponding strands of wire together with the distal ends 134 of their corresponding grasper arms 126 aligned flush, and apply sufficient energy to melt the distal ends 134. The resulting molten metal at the distal ends 134 thereby pools together, and surface tension pulls the liquid metal into a spheroidal shape. As the metal cools, this shape is naturally maintained, resulting in an autogenous weld between the two strands of wire that is terminated by a spheroidal member.

The trap wire 151 serves as a mechanical plug, creating a blockage within the needle lumen 116 by which the suture magnet 202 of the magnetic suture 200 cannot pass. This can be accomplished various additional ways too. For example, rather than two grasper arms 126, a single grasper arm 126 could be employed with an enlarged spheroid end. This provides an advantage of being simpler to manufacture. Alternatively, more than two grasper arms 126 could be employed. The provides an advantage that multiple grasper arms 126 of a smaller cross-section could be employed to obtain an equivalent strength to a single grasper arm 126 of a larger cross-section, but the multiple grasper arms 126 would not intrude as far into the needle lumen 116, allowing for maximization of the diameter of the grasper magnet 140. A similar effect could be achieved by using a grasper arm 126 with a non-round profile for the grasper arm 126. Also alternatively, the plug element does not need to be melt-formed. A separate component may be attached, such as by swaging, or by employing an adhesive. The plug element also does not need to be spheroid, as its shape is not critical to its function. Thus the plug element alternatively could be shaped as, for example, an elongated cylinder, or a pyramid, or a toroid. Also alternatively, the grasper arm 126 could simply terminate in a pig-tailed coil, forming a basket-like shape.

Accordingly, as shown in FIG. 8 for the first embodiment 1001 and in FIG. 22 for the second embodiment 1002, with reference to FIGS. 43-47 and FIG. 50 for both embodiments, in some embodiments the grasper wire 120 is a first grasper wire 120 and the grasper arm 126 is a first grasper arm 126. In these embodiments, the magnet-assisted suture grasper 100 further comprises: (a) a second grasper wire 120 having a proximal end 122 and a distal end 124 and being fixedly disposed within the retriever body 146; and (b) a second grasper arm 126 comprising a proximal end 128, a proximal-to-intermediate portion 130, a distal portion 132, and a distal end 134, the second grasper arm 126 extending from the distal end 124 of the second grasper wire 120 and being reversibly moveable between the first position 136 and the second position 138. In these embodiments, the first and second grasper arms 126 are connected at their distal ends 134, thereby forming a grasper arm loop 150. In these embodiments, the first and second grasper arms 126 further comprises an enlarged distal terminus 148 at the distal ends 134 of the first and second grasper arms 126. In these embodiments, the grasper arm loop 150 is reversibly moveable between the first position 136 and the second position 138 based on translation of the grasper arm loop 150 from inside of the needle lumen 116 to outside of the needle lumen 116 through the distal hole 114 of the needle body 108. In these embodiments, the grasper arm loop 150 circumscribes an area sufficiently large, and the enlarged distal terminus 148 at the distal ends 134 of the first and second grasper arms 126 has a size sufficiently small, to allow contact between the grasper magnet 140 and a suture magnet 202 of a magnetic suture 200 attracted thereto when the grasper arm loop 150 is in the second position 138. In these embodiments, the enlarged distal terminus 148 at the distal ends 134 of the first and second grasper arms 126 has a size sufficiently small to allow a suture 204 of the magnetic suture 200 to pass when the grasper arm loop 150 is in the first position 136. In these embodiments, the enlarged distal terminus 148 at the distal ends 134 of the first and second grasper arms 126 has a size sufficiently large to block the suture magnet 202 of the magnetic suture 200 from exiting the needle lumen 116 through the distal hole 114 of the needle body 108 when the grasper arm 126 is in the first position 136. These embodiments are advantageous for allowing use of grasper arms 126 having relatively smaller diameters. In some examples of these embodiments, the size of the enlarged distal terminus 148 is about 10% to about 90%, preferably about 20% to about 80%, more preferably about 30% to about 60% of the inner diameter of the needle lumen 116. For example, the enlarged distal terminus 148 can have a diameter that is about 10% to about 90%, preferably about 20% to about 80%, more preferably about 30% to about 60% of the inner diameter of the needle lumen 116. Also in some of these embodiments the mean diameter of the grasper arm loop 150 is about 0.5% to about 10%, preferably about 2% to about 4%, more preferably about 2.3% to about 3.5% of the inner diameter of the needle lumen 116.

Alternatively or additionally, as shown in FIGS. 64-69, in some embodiments the grasper wire 120 is a first grasper wire 120 and the grasper arm 126 is a first grasper arm 126. In these embodiments, the magnet-assisted suture grasper 100 further comprises: (a) a second grasper wire 120 having a proximal end 122 and a distal end 124 and being fixedly disposed within the retriever body 146; and (b) a second grasper arm 126 comprising a proximal end 128, a proximal-to-intermediate portion 130, a distal portion 132, and a distal end 134, the second grasper arm 126 extending from the distal end 124 of the second grasper wire 120 and being reversibly moveable between the first position 136 and the second position 138. In these embodiments, the first and second grasper arms 126 comprise curved portions 152 adjacent their distal ends 134. In these embodiments, the first and second grasper arms 126 are reversibly moveable between the first position 136 and the second position 138 based on translation of the first and second grasper arms 126 from inside of the needle lumen 116 to outside of the needle lumen 116 through the distal hole 114 of the needle body 108. The proximal-to-intermediate portions 130 of the first and second grasper arms 126 are substantially parallel to the needle body axis 110 and the curved portions 152 adjacent the distal ends 134 of the first and second grasper arms 126 curve inwardly toward the needle body axis 110 when the first and second grasper arms 126 are in the first position 136. In these embodiments, at least one of the first or second grasper arms 126 pivots reversibly outwardly from the needle body axis 110 sufficiently far to allow contact between the grasper magnet 140 and a magnetic suture 200 attracted thereto when the first and second grasper arms 126 are in the second position 138. In these embodiments, the curved portions 152 adjacent the distal ends 134 of the two grasper arms 126 contact the magnetic suture 200 to block the magnetic suture 200 from exiting the needle lumen 116 through the distal hole 114 of the suture retrieval needle 102 when the first and second grasper arms 126 are in the first position 136. In these embodiments, the two grasper arms 126 can function as a pincer that includes a crotch. In such embodiments, the grasper magnet 140 can advantageously be attached to the crotch of the pincer to attract and hold a magnetic suture 200 in place, thereby easing capture by the pincer. In some examples of these embodiments, both the first and second grasper arms 126 pivot reversibly outwardly from the needle body axis 110 when the first and second grasper arms 126 are in the second position 138.

As shown in FIG. 50, in some embodiments the grasper arm 126 further comprises an enlarged distal terminus 148 at the distal end 134 of the grasper arm 126. In accordance with these embodiments, the grasper arm 126 is reversibly moveable between the first position 136 and the second position 138 based on translation of the grasper arm 126 from inside of the needle lumen 116 to outside of the needle lumen 116 through the distal hole 114 of the needle body 108. In accordance with these embodiments, the enlarged distal terminus 148 at the distal end 134 of the grasper arm 126 has a size sufficiently small to allow contact between the grasper magnet 140 and a suture magnet 202 of a magnetic suture 200 attracted thereto when the grasper arm 126 is in the second position 138 and to allow a suture 204 of the magnetic suture 200 to pass when the grasper arm 126 is in the first position 136. In these embodiments, the enlarged distal terminus 148 at the distal end 134 of the grasper arm 126 has a size sufficiently large to block the suture magnet 202 of the magnetic suture 200 from exiting the needle lumen 116 through the distal hole 114 of the needle body 108 when the grasper arm 126 is in the first position 136. In these embodiments, it is the enlarged distal terminus 148 that prevents the magnetic suture 200 from being pulled out of the needle lumen 116. Accordingly, such a grasper arm 126 only needs to be advanced so far as to free the enlarged distal terminus 148 from the constraint of the suture retrieval needle 102. If a force is then applied to the magnetic suture 200, and if the magnetic suture 200 includes a tapered ferrule 206, then the enlarged distal terminus 148 will ride up the tapered ferrule 206, which will deflect the grasper arm 126 away from the tapered ferrule 206, and allow the magnetic suture 200 to pass from the needle lumen 116. This can be advantageous for suturing at sites within a patient in which space is limited, since it is not necessary for the entire grasper arm 126 to travel beyond the distal end 106 of the suture retrieval needle 102 in order to release the magnetic suture 200. In some examples of these embodiments, the size of the enlarged distal terminus 148 is about 10% to about 90%, preferably about 20% to about 80%, more preferably about 30% to about 60% of the inner diameter of the needle lumen 116. For example, the enlarged distal terminus 148 can have a diameter that is about 10% to about 90%, preferably about 20% to about 80%, more preferably about 30% to about 60% of the inner diameter of the needle lumen 116.

Figure 52:
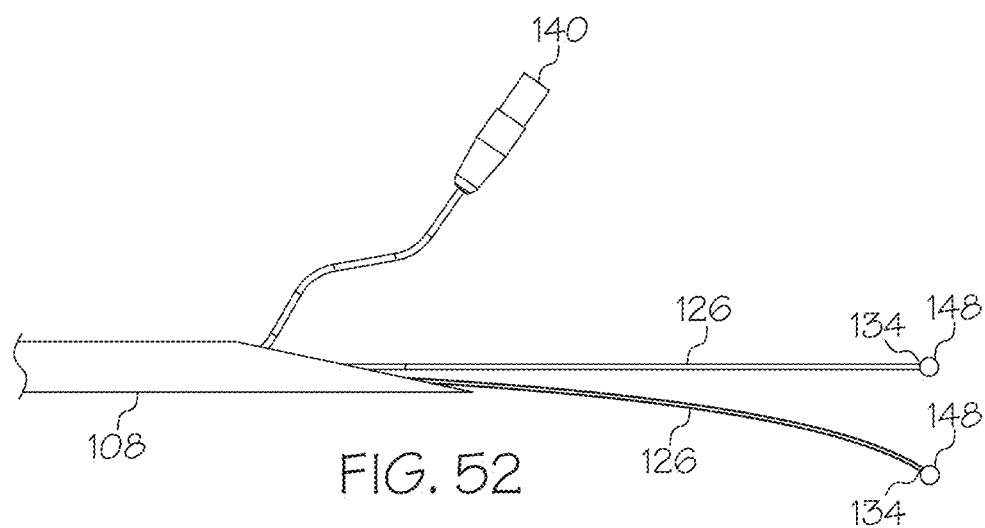
FIG. 52 is a side view of a second alternate embodiment of a grasper arm of a magnet-assisted suture grasper as disclosed herein.
Figure 53:
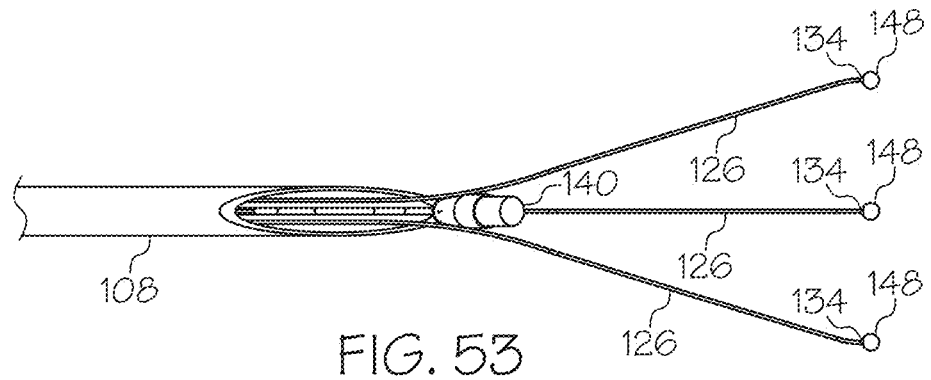
FIG. 53 is a side view of a third alternate embodiment of a grasper arm of a magnet-assisted suture grasper as disclosed herein.
Figure 61:
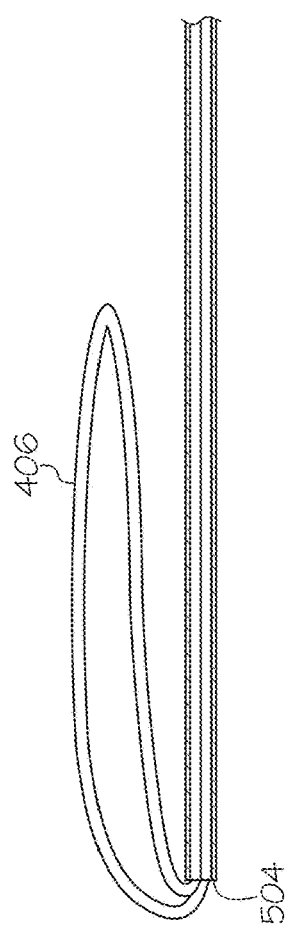
FIG. 61 is a sectional view of the loop-end of the preloaded magnetic suture cartridge of FIG. 59.
Figure 62:
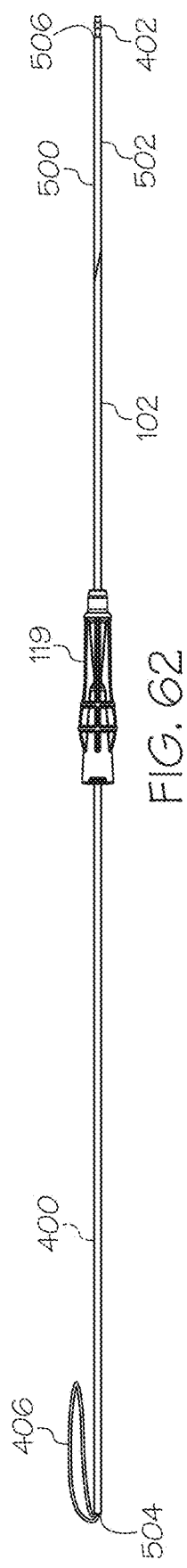
FIG. 62 is a side view of the preloaded magnetic suture cartridge of FIG. 59 in an introducer needle.
Figure 63:
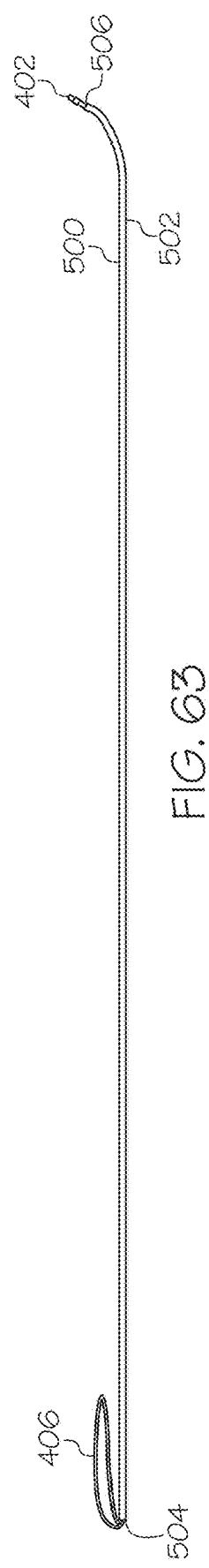
FIG. 63 is a side view of an alternate embodiment a preloaded magnetic suture cartridge as disclosed herein in which the magnet-end of the preloaded magnetic suture cartridge is curved.
Figure 64:
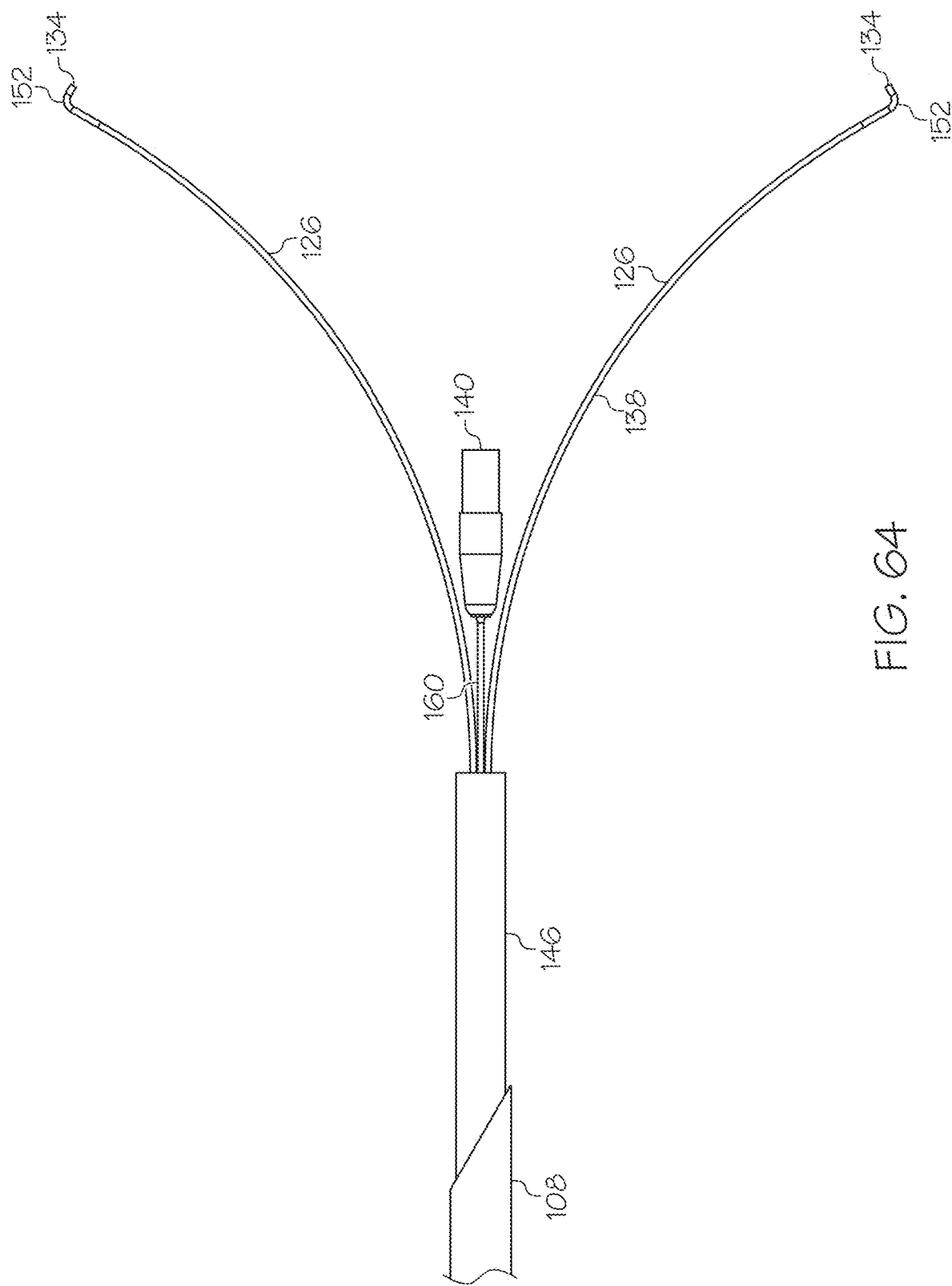
FIG. 64 is a side view of a fourth alternate embodiment of a grasper arm of a magnet-assisted suture grasper as disclosed herein.
Figure 65:
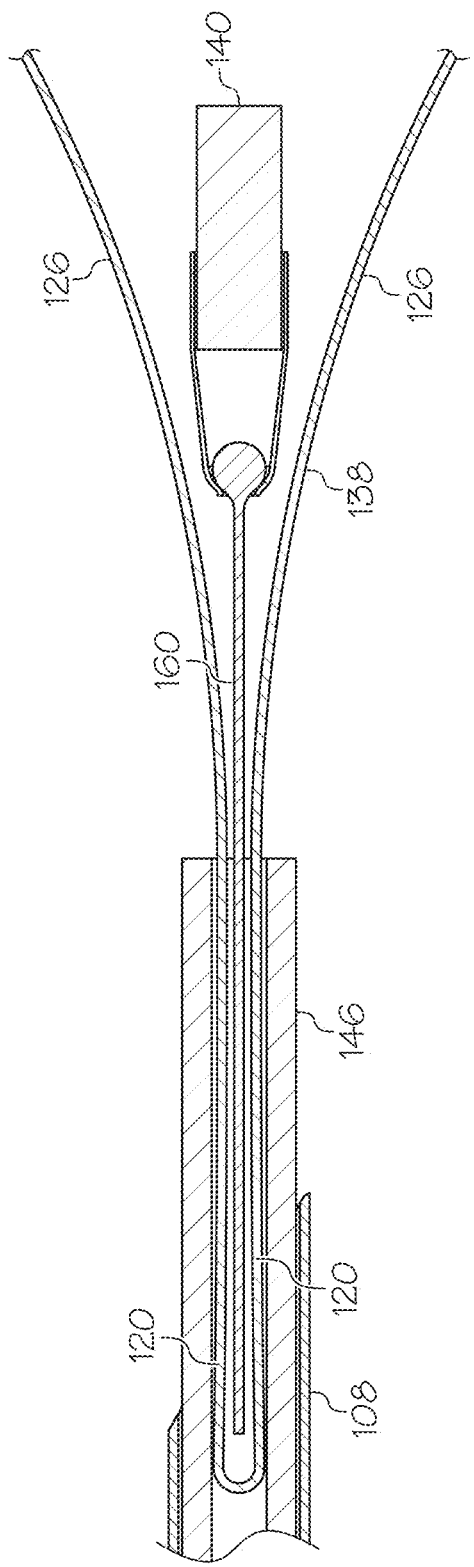
FIG. 65 is a sectional view of the fourth alternate embodiment of the grasper arm of FIG. 64.
Figure 66:
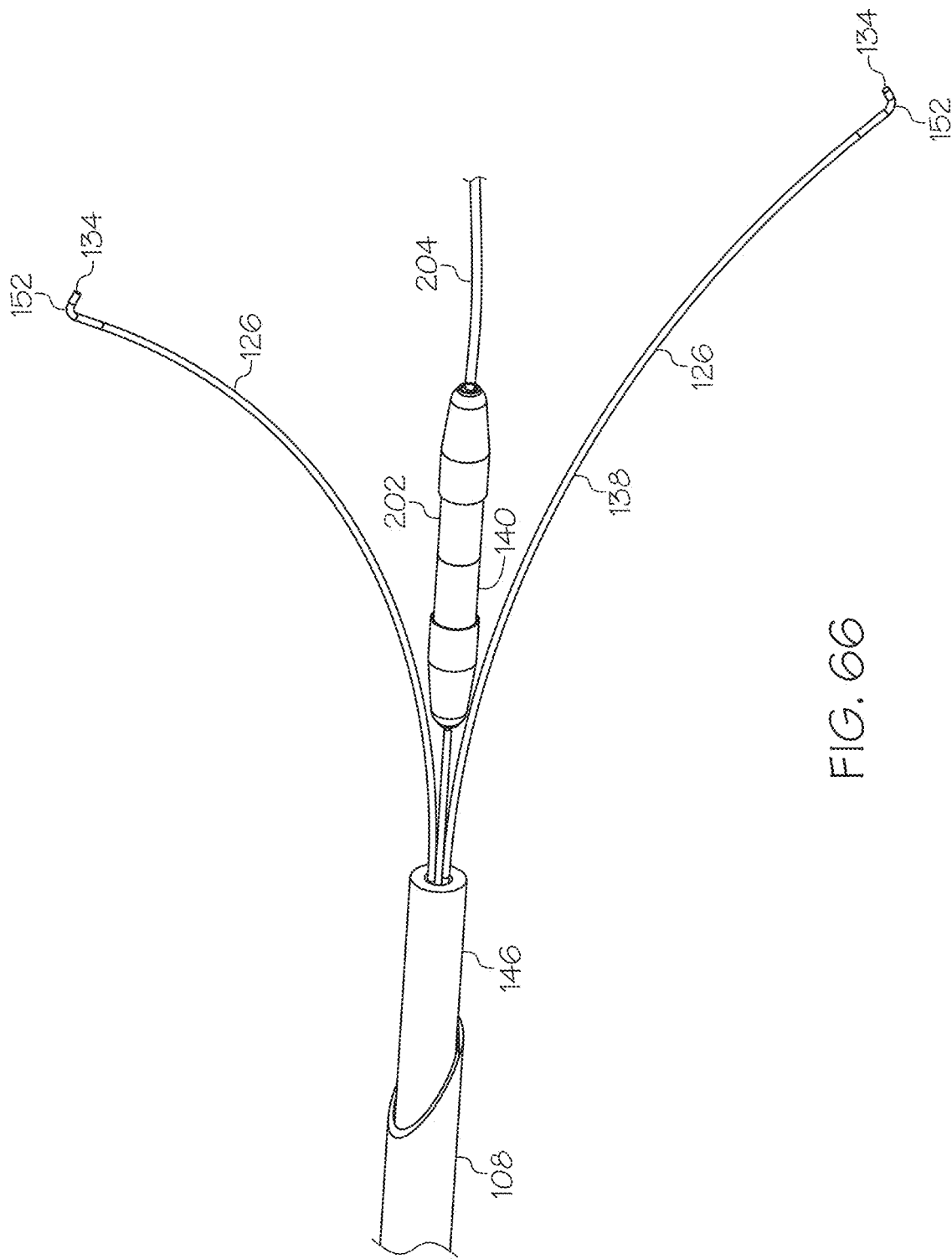
FIG. 66 is a perspective view of the fourth alternate embodiment of the grasper arm of FIG. 64, in which the grasper magnet of the magnet-assisted suture grasper is attracting a magnetic suture and in contact with the magnetic suture.
Figure 67:
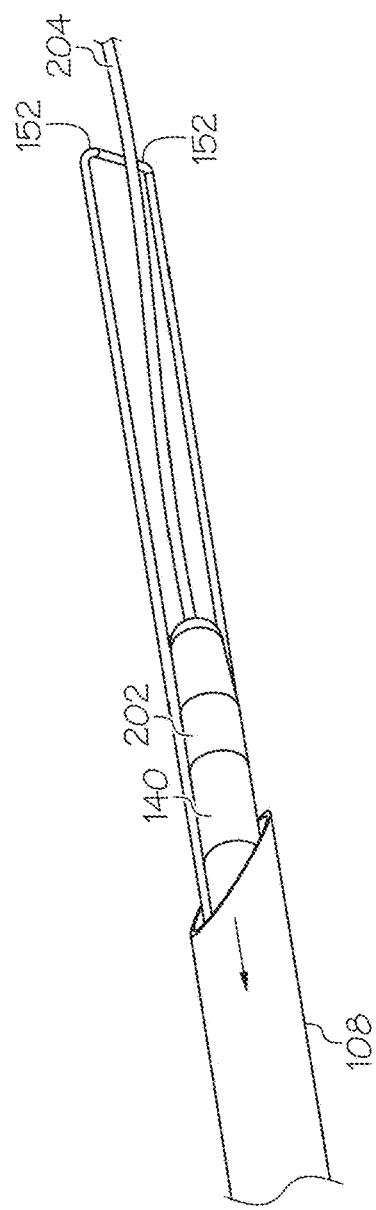
FIG. 67 is a perspective view of the fourth alternate embodiment of the grasper arm of FIG. 64, in which the grasper magnet is attracting a magnetic suture and in contact with the magnetic suture, such that the magnetic suture has been captured within the needle lumen of the suture retrieval needle of the magnet-assisted suture grasper.
Figure 68:
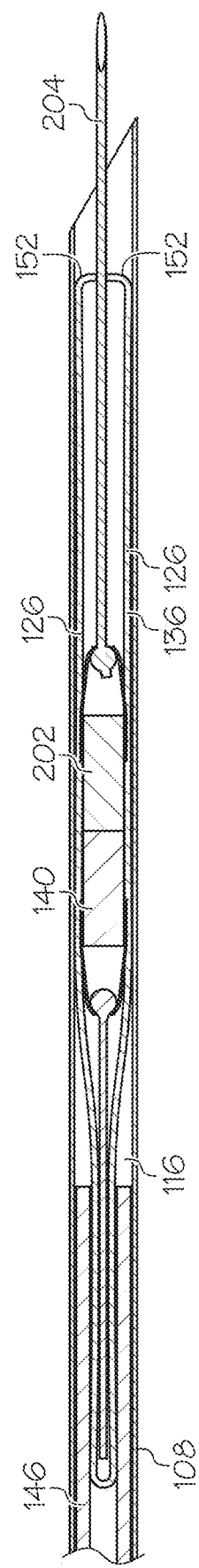
FIG. 68 is a sectional view of the fourth alternate embodiment of the grasper arm of FIG. 64, in which the grasper magnet is attracting a magnetic suture and in contact with the magnetic suture, such that the magnetic suture has been captured within the needle lumen of the suture retrieval needle of the magnet-assisted suture grasper.
Figure 69:
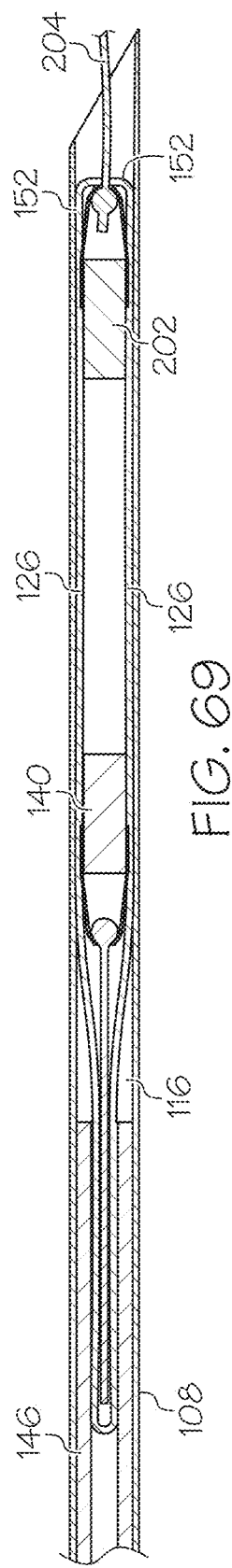
FIG. 69 is a sectional view of the fourth alternate embodiment of the grasper arm of FIG. 64, in which the distal end of the grasper arm is grasping the magnetic suture, such that the magnetic suture remains captured within the needle lumen of the suture retrieval needle of the magnet-assisted suture grasper.

As shown in FIG. 52 and FIG. 53, in some embodiments the grasper wire 120 is a first grasper wire 120 and the grasper arm 126 is a first grasper arm 126. In these embodiments, the magnet-assisted suture grasper 100 further comprises: (a) a second grasper wire 120 having a proximal end 122 and a distal end 124 and being fixedly disposed within the retriever body 146; and (b) a second grasper arm 126 comprising a proximal end 128, a proximal-to-intermediate portion 130, a distal portion 132, and a distal end 134, the second grasper arm 126 extending from the distal end 124 of the second grasper wire 120 and being reversibly moveable between the first position 136 and the second position 138. In these embodiments, the first grasper arm 126 further comprises an enlarged distal terminus 148 at the distal end 134 of the first grasper arm 126, and the second grasper arm 126 further comprises an enlarged distal terminus 148 at the distal end 134 of the second grasper arm 126. In these embodiments, the first and second grasper arms 126 are reversibly moveable between the first position 136 and the second position 138 based on translation of the first and second grasper arms 126 from inside of the needle lumen 116 to outside of the needle lumen 116 through the distal hole 114 of the needle body 108. In these embodiments, the enlarged distal termini 148 of the first and second grasper arms 126 have sizes sufficiently small to allow contact between the grasper magnet 140 and a suture magnet 202 of a magnetic suture 200 attracted thereto when the first and second grasper arms 126 are in the second position 138 and to allow a suture 204 of a magnetic suture 200 to pass when the first and second grasper arms 126 are in the first position 136, and sufficiently large to block the suture magnet 202 of the magnetic suture 200 from exiting the needle lumen 116 through the distal hole 114 of the needle body 108 when the first and second grasper arms 126 are in the first position 136. In some of these embodiments, the magnet-assisted suture grasper 100 further comprises at least one additional grasper wire 120 and at least one additional grasper arm 126 extending distally from the at least one additional grasper wire 120. These embodiments can be advantageous by allowing for a larger grasper magnet 140 than an equivalent single grasper arm 126 having the same total cross-sectional area. This is because the two or more grasper arms 126 can be positioned radially about the inner surface of a needle lumen 116, allowing for the cross-sectional area of the grasper arms 126 to be distributed unequally. This leaves more usable space for the grasper magnet 140 to occupy. For example, a dual grasper arm design provides a 12% increase in usable space over a single grasper arm design, while a quadruple grasper arm design provides a 20% increase in usable space over the single grasper arm design. Moreover, the same effect could be achieved by using a wire with a non-round profile for the grasper arm 126.

Also in some embodiments the grasper wire 120 is a first grasper wire 120 and the grasper arm 126 is a first grasper arm 126. In these embodiments, the magnet-assisted suture grasper 100 further comprises: (a) a second grasper wire 120 having a proximal end 122 and a distal end 124 and being fixedly disposed within the retriever body 146; and (b) a second grasper arm 126 comprising a proximal end 128, a proximal-to-intermediate portion 130, a distal portion 132, and a distal end 134, the second grasper arm 126 extending from the distal end 124 of the second grasper wire 120 and being reversibly moveable between the first position 136 and the second position 138. In these embodiments, the first and second grasper arms 126 are connected at their distal ends 134, thereby forming a grasper arm loop 150. In these embodiments, the grasper arm loop 150 is reversibly moveable between the first position 136 and the second position 138 based on translation of the grasper arm loop 150 from inside of the needle lumen 116 to outside of the needle lumen 116 through the distal hole 114 of the needle body 108. In these embodiments, the grasper arm loop 150 circumscribes an area sufficiently large to allow contact between the grasper magnet 140 and a suture magnet 202 of a magnetic suture 200 attracted thereto when the grasper arm loop 150 is in the second position 138. In these embodiments, the grasper arm loop 150 has a thickness sufficiently great to block the suture magnet 202 of the magnetic suture 200 from exiting the needle lumen 116 through the distal hole 114 of the suture retrieval needle 102 when the grasper arm loop 150 is in the first position 136. For these embodiments in which the grasper arms 126 do not comprise an enlarged distal terminus 148 at their distal ends 134, advantages include ease of manufacture and the possibility of using a larger grasper magnet 140. In some of these embodiments the mean diameter of the grasper arm loop 150 is about 0.5% to about 10%, preferably about 2% to about 4%, more preferably about 2.3% to about 3.5% of the inner diameter of the needle lumen 116.

Also in some embodiments the grasper wire 120 is a first grasper wire 120 and the grasper arm 126 is a first grasper arm 126. In these embodiments, the magnet-assisted suture grasper 100 further comprises: (a) a second grasper wire 120 having a proximal end 122 and a distal end 124 and being fixedly disposed within the retriever body 146; and (b) a second grasper arm 126 comprising a proximal end 128, a proximal-to-intermediate portion 130, a distal portion 132, and a distal end 134, the second grasper arm 126 extending from the distal end 124 of the second grasper wire 120 and being reversibly moveable between the first position 136 and the second position 138. In these embodiments, the first and second grasper arms 126 are connected at their distal ends 134, thereby forming a grasper arm loop 150. In these embodiments, the grasper arm loop 150 is reversibly moveable between the first position 136 and the second position 138 based on translation of the grasper arm loop 150 from inside of the needle lumen 116 to outside of the needle lumen 116 through the distal hole 114 of the needle body 108. In these embodiments, the grasper arm loop 150 is in an elastically deformed closed state when the grasper arm loop 150 is in the first position 136, and the grasper arm loop 150 reversibly expands to an open state when the grasper arm loop 150 is in the second position 138. In these embodiments, the grasper arm loop 150 circumscribes an area sufficiently large to allow contact between the grasper magnet 140 and a suture magnet 202 of a magnetic suture 200 attracted thereto when the grasper arm loop 150 is in the second position 138. In these embodiments, the grasper arm loop 150 snares the suture magnet 202 of the magnetic suture 200 to block the suture magnet 202 from exiting the needle lumen 116 through the distal hole 114 of the suture retrieval needle 102 when the grasper arm loop 150 is in the first position 136. In some of these embodiments, the grasper arm loop 150 is formed of a shape memory alloy. In these embodiments, the grasper arm loop 150 can be a snare, and the snare can include a crotch. In such embodiments, the grasper magnet 140 can advantageously be attached to the crotch of the snare to attract and hold a magnetic suture 200 in place, thereby eliminating the difficult step of threading a suture through the eye of the snare under two-dimensional visualization. In some of these embodiments the mean diameter of the grasper arm loop 150 is about 0.5% to about 10%, preferably about 2% to about 4%, more preferably about 2.3% to about 3.5% of the inner diameter of the needle lumen 116.

Considering the first embodiment 1001 of the magnet-assisted suture grasper 100 further, in some embodiments the magnet-assisted suture grasper 100 further comprises the hub 119 of the suture retrieval needle 102 and a handle attached to the retriever body 146. This is advantageous for improving the ergonomics of the magnet-assisted suture grasper 100 by allowing for single-handed operation. The handle would preferentially include a non-axisymmetric design so as to rotationally fix the handle and the retriever body 146.

Also in some embodiments the magnet-assisted suture grasper 100 further comprises a return mechanism, such as a spring. In these embodiments, the retriever body 146 can be attached directly to the handle, so that when the handle is depressed, the retriever body 146 is advanced, which in turn advances the grasper arm 126 and the grasper magnet 140 from the needle lumen 116. When the handle is released, the spring returns the handle to the original position. This returns the grasper arm 126 and the grasper magnet 140 to the needle lumen 116.

The embodiment 1001 of the magnet-assisted suture grasper 100 including a retriever body 146 can be operated as follows.

After a magnetic suture 200 has been deposited inside a patient, the suture retrieval needle 102 is introduced into the patient to gain access to the site of the suture. The retriever body 146 is used to advance the grasper arm 126 and the grasper magnet 140 through the needle lumen 116 of the suture retrieval needle 102 until the grasper arm 126 and the grasper magnet 140 exit the needle lumen 116, extending past the distal hole 114 of the suture retrieval needle 102. The grasper arm 126 and the grasper magnet 140 are brought near the suture magnet 202 of the magnetic suture 200, so that the magnetic fields of the grasper magnet 140 and the suture magnet 202 can interact. The attractive force between the grasper magnet 140 and the suture magnet 202 pulls the suture magnet 202 towards the grasper magnet 140 and brings them into contact and axial alignment.

Then the retriever body 146 is used to pull the grasper arm 126 and the grasper magnet 140 back inside the needle lumen 116 of the suture retrieval needle 102. The attractive force between the grasper magnet 140 and the suture magnet 202 allows the grasper magnet 140 to tow the suture magnet 202, and the attached suture 204, along with it. The retriever body 146 is pulled back until the grasper magnet 140 and the suture magnet 202 are brought entirely inside the needle lumen 116. At this point, the magnetic suture 200 cannot escape the suture retrieval needle 102, because the distal end 134 of the grasper arm 126 blocks the exit path. The proximal end 128 of the grasper arm 126 is attached to the retriever body 146, so the grasper arm 126 is not moved by the suture 204.

Once the magnetic suture 200 has been captured, the magnet-assisted suture grasper 100 can be used to pull or push the magnetic suture 200 to a new location. The grasper arm 126 allows the magnet-assisted suture grasper 100 to hold the magnetic suture 200 securely, even when the magnetic suture 200 is heavily loaded to the point that the load exceeds the attractive force between grasper magnet 140 and the suture magnet 202. The grasper arm 126 prevents the suture magnet 202 of the magnetic suture 200 from being pulled back out of the needle lumen 116, even when the force applied exceeds the strength of attraction between the grasper magnet 140 and the suture magnet 202.

Once the magnetic suture 200 has been passed to the desired location, the magnetic suture 200 can be released from the magnet-assisted suture grasper 100. To release the magnetic suture 200, the retriever body 146 is used to advance the grasper arm 126, the grasper magnet 140, and the suture magnet 202 out of the needle lumen 116, and the suture 204 can then be pulled to disconnect the grasper magnet 140 and the suture magnet 202.

Considering the second embodiment 1002 of the magnet-assisted suture grasper 100 further, as shown in FIGS. 21-43 the second embodiment 1002 further comprises a lock mechanism 300 that can be reversibly engaged to prevent translation of the retriever body 146 within the needle lumen 116 in the first direction and/or the second direction. The lock mechanism 300 can be advantageous for bearing fully a tensile load applied to a magnetic suture 200 in the same direction.

In some embodiments, the lock mechanism 300 that can be reversibly engaged in a first setting that prevents translation of the retriever body 146 within the needle lumen 116 when the distal end 134 of the grasper arm 126 is inside the needle lumen 116 and reversibly engaged in a second setting that prevents translation of the retriever body 146 within the needle lumen 116 when the grasper magnet 140 is outside the needle lumen 116. In some examples of these embodiments, maintaining the lock mechanism 300 in the first setting or the second setting does not require energy input.

Figure 21:
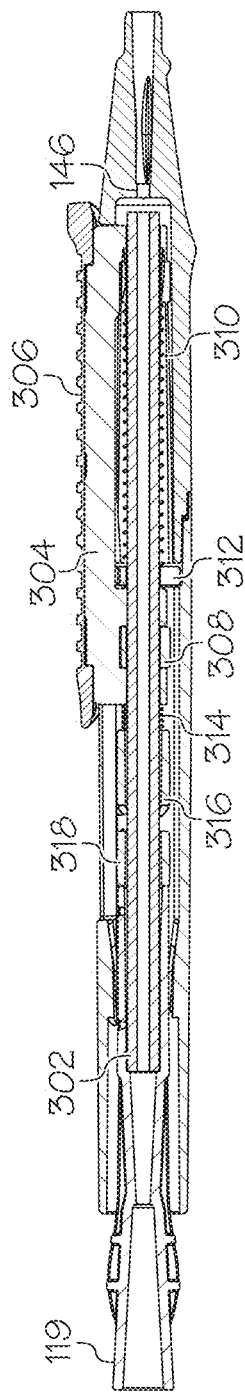
FIG. 21 a sectional view of the magnet-assisted suture grasper of FIG. 11.

The embodiment 1002 of the magnet-assisted suture grasper 100 is such an example. With reference to FIG. 21 and FIG. 22, the embodiment 1002 includes an advancer assembly comprising the retriever body 146, a stabilizer tube 302, an advancer frame 304, an advancer pad 306, guide bushings 308, a return spring 310, a spring keeper 312, a cam spring 314, a drive cam 316, a lock cam 318, a hub 119, and an end effector 320 comprising the trap wire 151 and the magnet wire 160 with the magnet 140 attached. In accordance with these examples, the retriever body 146 passes through a lumen of the stabilizer tube 302, and is rigidly fixed to the stabilizer tube 302. The end effector 320 is rigidly fixed to the retriever body 146. The stabilizer tube 302 passes through ventral rings of the advancer frame 304, both guide bushings 308, the spring keeper 312, the drive cam 316, and the lock cam 318, terminating within the body of the hub 119. The hub 119 and the advancer frame 304 are rigidly fixed to the stabilizer tube 302, and the advancer pad 306 is rigidly fixed to the advancer frame 304. The guide bushings 308 are non-rigidly fixed, but are constrained rotationally and laterally by the advancer frame 304, such that these components move in unison as a single unit. The spring keeper 312 is not fixed within the advancer assembly, but is laterally constrained by a barrel 322 and nose cone 324, such that the spring keeper 312 has a longitudinal position that is fixed relative to these components. The entire advancer assembly slides within the inner channel of the barrel 322 and nose cone 324, such that the return spring 310 compresses between the first guide bushing 308 and the spring keeper 312 during this motion.

In accordance with these examples, the second embodiment 1002 of the magnet-assisted suture grasper 100 can be operated as follows.

With reference to FIGS. 23-30 and FIGS. 32-35, initially the advancer assembly of the second embodiment 1002 of the magnet-assisted suture grasper 100 is in an unlocked intermediate position and the grasper arm 126 is in a position intermediate between the first position 136 and the second position 138. To begin operation, an operator slides the advancer assembly back, with sufficient force to compress the return spring 310, until the advancer frame 304 engages the maximal boundary of a travel slot 326. This pulls the end effector 320 into the needle lumen 116 and pushes the lock cam 318 into the relieved space 340 proximal to the locking features of the barrel 322. With the guide lugs 328 of the lock cam 318 now freed from the rotational constraint imposed by linear guide channels 330 of the barrel 322, the force exerted by the (preloaded) cam spring 314 is translated into a rotational movement of the lock cam 318 by way of mating lock cam teeth 332 and drive cam teeth 334 between the lock cam 318 and drive cam 316. Rotation of the lock cam 318 is halted when crests of the lock cam teeth 332 become nested in valleys between drive cam teeth 334. At this point, the advancer assembly is in an unlocked retracted position and the grasper arm 126 is in the first position 136. This is designated "Position A." A continual application of external force, e.g., as applied by the operator, sufficient to overcome the elastic strain that has been loaded into the return spring 310, is required to maintain the advancer assembly in this position.

With reference to FIGS. 23-30 and FIGS. 36-39, to continue operation, the operator releases the advancer assembly, which, in the absence of any external force, is pushed forward by the return spring 310, which had been compressed in the previous position. As the advancer assembly moves forward, the lock cam teeth 332 slide along the lock ramps 336 of the barrel 322, resulting in simultaneous linear and rotational translation of the lock cam 318. This continues until the lock cam teeth 332 meet the lock stops 338 in the barrel 322, at which point the advancer assembly becomes mechanically locked against any further movement in this direction. At this point, the advancer assembly is in a locked intermediate position and the grasper arm 126 is in a position intermediate between the first position 136 and the second position 138. This is designated "Position B." The system is in a state of equilibrium in this position, such that no external force is required to maintain this position.

With reference to FIGS. 23-30 and FIGS. 40-43, to continue operation, the operator briefly pulls the advancer assembly back to return the advancer assembly to the previous unlocked retracted position. During this movement, the lock cam 318 once again engages the drive cam 316, and the lock cam teeth 332 are rotated into the next valley in the crown of the drive cam 316. When the advancer assembly is released from this position, the return spring 310 pushes the advancer assembly forward, and the lock cam teeth 332 engage the channel ramps 342 in the barrel 322. The channel ramps 342 guide the teeth 332 and guide lugs 328 of the lock cam 318 into the linear guide channels 330. The return spring 310 continues to push the advancer assembly forward until the advancer frame 304 engages the minimum boundary of the travel slot 326, pushing the end effector 320 out of the cannula. At this point, the advancer assembly is in the locked extended position and the grasper arm 126 is in the second position 138. This is designated "Position C." The system is in a state of equilibrium in this position, where no external force is required to maintain this position.

To continue operation, the operator briefly pulls the advancer assembly back. This returns the advancer assembly to the unlocked intermediate position and the grasper arm 126 to the position intermediate between the first position 136 and the second position 138.

The second embodiment 1002 of the magnet-assisted suture grasper 100 relies on magnetic attraction to establish a steady-state connection between the magnet-assisted suture passer 100 and a magnetic suture 200 when in Position C as follows. With reference to FIGS. 43-45, the operator moves the advancer assembly forward such that the advancer assembly is in the locked extended position and the grasper arm 126 is in the second position 138, i.e. Position C. The trap wire 151 and the grasper magnet 140 are brought near the suture magnet 202 of the magnetic suture 200. The trap wire 151 and the grasper magnet 140 do not need to be precisely aligned with the suture magnet 202, but only brought near so that the magnetic fields of the grasper magnet 140 and the suture magnet 202 may interact, allowing the magnetic moments to pull the southern pole of the suture magnet 202 into contact with the northern pole of the grasper magnet 140, thereby establishing a steady-state connection between the magnet-assisted suture passer 100 and a magnetic suture 200.

With reference to FIG. 46, the second embodiment 1002 of the magnet-assisted suture grasper 100 can then accomplish mechanical capture of the magnetic suture 200 by moving from Position C to Position A as follows. After initial attraction, the operator briefly pulls the advancer assembly back, thereby bringing the advancer assembly through the initial unlocked intermediate position and returning the advancer assembly to an unlocked retracted position in which the grasper arm 126 is in the first position 136, i.e. Position A. The steady-state connection between grasper magnet 140 and the suture magnet 202 allows the grasper magnet 140 to tow the magnetic suture 200 into the needle lumen 116. The length of the trap wire 151 is designed such that the enlarged distal terminus 148 at the end of the trap wire 151 maintains a distal position relative to the suture magnet 202 inside the cannula. This allows the enlarged distal terminus 148 to act as a plug, creating a physical blockage inside the needle lumen 116 by which the suture magnet 202 of the magnetic suture 200 cannot pass.

Figure 47:
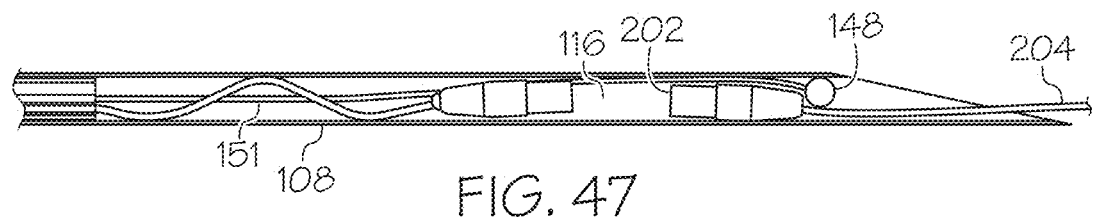
FIG. 47 is a sectional view of the distal end of the magnet-assisted suture grasper of FIG. 1, in which the grasper arm is in a position intermediate between the first position and the second position, and an enlarged distal terminus at the distal end of the grasper arm is grasping the magnetic suture, such that the magnetic suture remains captured within the needle lumen of the suture retrieval needle of the magnet-assisted suture grasper. This also is a sectional view of the distal end of the magnet-assisted suture grasper of FIG. 11, in which the advancer assembly is in the locked intermediate position, the grasper arm is in a position intermediate between the first position and the second position, and an enlarged distal terminus at the distal end of the grasper arm is grasping the magnetic suture, such that the magnetic suture remains captured within the needle lumen of the suture retrieval needle of the magnet-assisted suture grasper.

With reference to FIG. 47, the second embodiment 1002 of the magnet-assisted suture grasper 100 can then accomplish mechanical retention of the magnetic suture 200 in Position B as follows. The operator releases the advancer assembly, which is pushed forward by the return spring 310, moving the advancer assembly from the unlocked retracted position, which is energetically unfavorable, to the locked intermediate position, i.e. Position B, which is equipoised. The grasper arm 126 is then in a position intermediate between the first position 136 and the second position 138. While the advancer assembly remains in the locked intermediate position, when the magnetic suture 200 is tensely loaded with a force that exceeds the attractive strength between the grasper magnet 140 and the suture magnet 202, the suture magnet 202 will be pulled away from grasper magnet 140, but will be stopped from exiting the needle lumen 116 by the trap wire 151. The tensile load applied to the magnetic suture 200 is thereby borne by the trap wire 151, which is translated through the trap wire 151 into the retriever body 146 by way of a rigid joint between these two elements, into the stabilizer tube 302 by way of the joint between these two elements, and into the lock cam 318 by way of the hub 119, which is also rigidly joined to the stabilizer tube 302. As the lock cam 318 is fixedly engaged with mechanical locking features of the barrel 322, this load is ultimately born by the interface between the lock cam 318 and the barrel 322. The ability of the device to resist tensile loading of the magnetic suture 200 is therefore limited by the tensile strength of these individual elements and the joints between them, as well as the shear strength of the lock cam teeth 332 and the lock stops 338 of the barrel 322. The material selections and cross-sectional areas of these elements ultimately define a much higher capacity for load bearing than that of the 3-0 suture this system is designed to work with, so that the suture itself becomes the limiting factor in the system. This is preferable to having another part of the system fail before the magnetic suture 200 because the surgeon is not artificially limited as to the amount of tension that can be applied by way of the magnetic suture 200. Another reason this is preferable is that when the system is overloaded and the magnetic suture 200 breaks, the suture magnet 202 of the magnetic suture 200 remains captured within the needle lumen 116, allowing for safe retrieval and disposal.

With reference to FIG. 48 and FIG. 49A-C, the second embodiment 1002 of the magnet-assisted suture grasper 100 also is designed so that the retriever body 146 and stabilizer tube 302 run centrally through all components. The retriever body 146 is designed with an open retriever tube lumen 182 that runs the length of the retriever body 146. The hub 119 component at the proximal end of the device is structured with an open hub lumen 346 that runs the entire length of the hub 119. At the distal end, the needle body 108 is also lumenally patent. When assembled, the retriever tube lumen 182 opens to the hub lumen 346 of the hub 119 at the proximal end, and the needle lumen 116 of the needle body 108 at this distal end, creating a lumenal path that extends from end to end through the entire device.

Considering the lock mechanism 300 of the second embodiment 1002 in more detail, this lock mechanism 300 is formed between three components, the lock cam 318, the drive cam 316, and the barrel 322. The guide lugs 328 of the lock cam 318 and the guide lugs 344 of the drive cam 316 extend from the outer surface of their respective lock cam 318 and drive cam 316 and are disposed 180° apart. The barrel 322 features two guide channels 330, which are relieved into the inner surface and are also disposed 180° apart. When assembled, the guide lugs 328 of the lock cam 318 and the guide lugs 344 of the drive cam 316 fit into and slide within the guide channels 330. The lock cam 318 and drive cam 316 are assembled over the stabilizer tube 302, distal to the hub 119 and proximal to the advancer frame 304. The cam spring 314 is placed between the advancer frame 304 and the drive cam 316. The cam spring 314 is pre-compressed during assembly so that it exerts a continual force upon the drive cam 316, acting to push the drive cam 316 towards the lock cam 318. The drive cam 316 features a crown of radially disposed V-shaped teeth 334. The lock cam 318 features right-triangle shaped teeth 332 with a matching ramp angle to that of the drive cam teeth 334. The barrel 322 features right angle teeth relieved into the inner surface of the barrel 322, proximal to the guide channels 330, also with ramp angles matching the lock and drive cams 316. The width of the lock cam teeth 332 is wider than the teeth 334 of the drive cam 316, so that the lock cam teeth 332 extend beyond the outer diameter of the drive cam teeth 334. The arrangement of teeth 332 on the lock cam 318 is such that when the lugs 328 of the lock cam 318 and the lugs 344 of the drive cam 316 are aligned, the apexes of the lock cam teeth 332 are slightly aft of the apexes of the nearest drive cam teeth 334. The arrangement of the barrel teeth is such that with the lock cam teeth 332 nested in the valley between drive cam teeth 334, the apexes of the lock cam teeth 332 sit slightly aft to the apex of the barrel teeth 334.

Operationally, the guide lugs 344 of the drive cam 316 remain within the guide channel 330 along all points of linear travel by the sliding assembly. As such, the drive cam 316 is always constrained against rotation about the neutral axis. The lock cam 318 is constrained in the same manner while the guide lugs 328 are positioned within the guide channel 330, but the lock cam 318 fully enters the relieved space 340 created by the barrel teeth 334 at the maximal extent of travel, i.e. Position A, which frees the guide lugs 328 of the lock cam 318 from guide channel 330, allowing the lock cam 318 to rotate about the neutral axis. When the guide lugs 328 of the lock cam 318 are freed from the constraints of the guide channel 330, the force exerted by the cam spring 314 drives the drive cam 316 towards the lock cam 318. The ramp angle of the mating lock cam teeth 332 and drive cam teeth 334 causes the lock cam 318 to slide along the drive cam tooth 334 towards the valley between drive cam teeth 334. As the drive cam 316 is rotationally constrained, but the lock cam 318 is not, this movement results in a counter-clockwise rotation of the lock cam 318 (approximately 45°). From this position, the sliding components of the assembly are moved back in the opposite direction, toward Position C, which causes the lock cam teeth 332 to make contact with the lock ramps 336 of the barrel 322. Sliding contact of the lock cam teeth 332 with the lock ramps 336 causes a further counterclockwise rotation of the lock cam 318, until the teeth 332 make contact with the lock stops 338 (approximately 45°). This is the locked position. In this position, further movement from Position A to Position C is not possible. The lock is released by the sliding the moving assembly back to Position A, which drives the lock cam teeth 332 beyond the extends of the lock stops 338, at which point the lock cam 318 is rotationally driven further clockwise by the drive cam teeth 334. From this position, the sliding assembly can be driven to Position C. As the lock cam 318 advances linearly towards Position C, the lock cam teeth 332 contact the channel ramps 342 in the barrel 322, and the sliding contact results in further counterclockwise rotation of the lock cam 318. At the lower apex of the channel ramps 342 are the guide channels 330, so that as the lock cam teeth 332 slide along the channel ramps 342 the guide lugs 328 are guided into the guide channels 330, allowing the entire sliding assembly to move towards Position C. The rotational nature of this cycle is such that one lock/unlock cycle results in 180° translation of the lock cam 318, and two complete lock/unlock cycles returns the components to their original position (360° rotation). This allows for the lock/unlock cycle to be repeated indefinitely.

As will be appreciated, other lock mechanisms can also be used with the magnet-assisted suture grasper 100. For example, the lock mechanism 300 can include a simple lever arm molded into a hub 119 of the suture retrieval needle 102 and serrations on the outer surface of a retriever body 146 such that the lever arm can engage with the serrations to lock the retriever body 146, and thus the grasper wire 120, against translation relative to the suture retrieval needle 102. Other suitable lock mechanisms 300 also can be used.

With reference to FIGS. 54-58, a magnetic suture loop 400 also is disclosed. The magnetic suture loop 400 comprises a suture magnet 402 and a bifurcated suture 404 extending from the suture magnet 402 and forming a suture loop 406.

The magnetic suture loop 400 can be made similarly as described in U.S. Pub. No. 2021/0059667, as discussed above. Thus, in some embodiments the magnetic suture loop 400 further comprises a ferrule 408 with a tapered region 410 in which the bifurcated suture 404 is provided knotted and secured with an adhesive and a straight region 412 in which the suture magnet 402 is provided.

The magnetic suture loop 400 is advantageous for providing a means of snaring a second suture, for the purpose of pulling the second suture through the suture loop 406 created by the first suture. A surgeon can accomplish this as follows. The magnetic suture loop 400 is first passed through a tissue of a patient, so that the magnetic suture loop 400 has an entrance point and an exit point from the patient. The entrance point and exit points can be separate points or the same point. A strand of a second suture is then passed through the suture loop 406 of the magnetic suture loop 400. The magnetic suture loop 400 is then pulled through the tissue from the opposite end. As the magnetic suture loop 400 is pulled through the entrance point of the tissue, the suture loop 406 is closed around the second suture by the tissue, effectively snaring the second suture. This snaring action allows the magnetic suture loop to pull the second suture through the tissue and out the exit point, so that the second suture now occupies the path that was previously occupied by the magnetic suture loop 400. This is advantageous because it allows limiting permutations of suture size, material, and construction, without restricting choice as to the type of suture that will be used. For example, if a surgeon wishes to use a different style of suture than the magnetic suture loop 400, the surgeon can use the magnetic suture loop 400 to establish the path, and then use the technique described above to quickly and easily exchange the magnetic suture loop 400 for a different second suture.

With reference to FIGS. 59-63, a preloaded magnetic suture cartridge 500 also is disclosed. The preloaded magnetic suture cartridge 500 comprises a magnetic suture loop 400 and a cartridge tube 502. The magnetic suture loop 400 can be as described above. The cartridge tube 502 comprises a cartridge tube proximal opening 504, a cartridge tube distal opening 506, and a cartridge tube lumen 508 therebetween.

The magnetic suture loop 400 can be preloaded into the cartridge tube 502 during manufacture, such that the suture loop 406 of the magnetic suture loop 400 traverses the cartridge tube lumen 508, which is sized such that the suture loop 406 is free to enter the cartridge tube lumen 508 but the suture magnet 402 of the suture loop 406 does not enter the cartridge tube lumen 508, so that the suture loop 406 can freely pass through the cartridge tube lumen 508 in one direction but is captured in the opposite direction. The wall thickness of the cartridge tube 502 and the modulus of the material used in its construction are such that the cartridge tube 502 has greater column strength than the suture loop 406, allowing the preloaded magnetic suture cartridge 500, including the magnetic suture loop 400, to be easily inserted into and advanced through a cannula by pushing from one end.

This is advantageous because the suture loop 406 itself does not have sufficient column strength to allow the suture loop 406 to be pushed through a cannula from one end. The cartridge tube 502 therefore facilitates advancing the suture loop 406 through a cannula and into the intracorporeal working space. The cannula and the cartridge tube 502 can then be removed, leaving only the suture loop 406 behind. Alternatively, the cannula can be removed and the cartridge tube 502 with captured suture loop 406 can be left behind. Leaving the cartridge tube 502 in this manner may provide some benefit during the procedure because the stiffness of the cartridge tube 502 provides the operator with a means for directionally manipulating the suture magnet 402 of the magnetic suture loop 400 at the distal end of the suture loop 406 from outside the body. To this effect, a curve can be added to the distal end of the cartridge tube 502, which further enhances the operator's ability to directionally manipulate the suture magnet 402 of the magnetic suture loop 400 within the intracorporeal space.

A system for passing a magnetic suture also is disclosed. The system comprises the magnet-assisted suture grasper as described above. The system also comprises a magnetic suture comprising a suture magnet and a suture extending from the suture magnet as described above.

Another system for passing a magnetic suture also is disclosed. The system comprises the magnet-assisted suture grasper as described above. The system also comprises a magnetic suture loop comprising a suture magnet and a bifurcated suture extending from the suture magnet and forming a suture loop as described above.

In some embodiments, this system further comprises a cartridge tube as described above. The cartridge tube comprises a cartridge tube proximal opening, a cartridge tube distal opening, and a cartridge tube lumen therebetween. The suture loop traverses the cartridge tube lumen based on having been inserted through the cartridge tube distal opening. The suture magnet is disposed outside of the cartridge tube lumen adjacent the cartridge tube distal opening.

The magnet-assisted suture grasper disclosed herein can be used for passing a magnetic suture that includes a suture magnet at an end of the suture. Such a magnetic suture can be made, for example, as described in U.S. Pub. No. 2021/0059667. The magnet-assisted suture grasper disclosed herein also can be used for passing a magnetic suture that is magnetic based on including a magnetic metal within the suture.

The magnet-assisted suture grasper disclosed herein may be useful in procedures including, among others: (1) Inguinal hernia repair through high ligation of the patent processus vaginalis as described above; (2) Laparoscopic port closure (typical suture size 2-0 and larger); (3) Microsurgery (typical suture size 7-0 and smaller); (4) General surgery (typical suture size 2-0 to 0); and (5) Orthopedic surgery (typical suture size 0 and larger).

The magnet-assisted suture grasper also may be modified for use in ultrasound-guided surgical techniques. The magnet-assisted suture grasper would be modified by making the distal end of the suture retrieval needle echogenic. This could be done, for example, by applying an echogenic treatment at the distal tip of the suture retrieval needle. The modified magnet-assisted suture grasper would then be used with a hypodermic needle for introducing a suture wherein the hypodermic needle also is echogenic at its distal end. Optionally the magnets of the magnet-assisted suture grasper and the magnetic suture and/or the ferrules that attach the magnets to the wire of the magnet-assisted suture grasper and to the suture also may be made echogenic, for example by applying an echogenic treatment to the magnets and/or the ferrules.

Use of the modified magnet-assisted suture grasper in ultrasound-guided surgical techniques could result in reductions in operative time and complexity by eliminating the need for suction equipment. Suction equipment currently is needed to pass the suture through the needle.

The modified magnet-assisted suture grasper also may allow an alternative technique whereby the suture is dropped off and retrieved from inside the abdominal cavity. This would allow the repair to be completed entirely through a single needle-access point, which would provide improved cosmesis, and could result in less post-operative pain. Under the current laparoscopic approach (termed the PEAR/PIRS technique), the needle is introduced through the skin and directed medial around the defect, exiting inferior to the defect through the peritoneum into the abdominal cavity. Drop-off and retrieval of the suture occurs in this space inside the abdominal cavity. This is not currently possible under ultrasonic guidance because the suture is not echogenic, so the surgeon would have to retrieve the suture from inside the abdominal cavity completely blind. This would be nearly impossible with the current state of suture passer technology (i.e., snares, graspers, etc.). In contrast, the modified magnet-assisted suture grasper may allow this to work, especially if the needle points and ferrules are echogenic.

The mechanical grasper arm technology described herein could be integrated into the magnetic U-stitch suturing device disclosed in U.S. Pat. No. 10,245,021 to provide a more secure means of holding a magnetic suture during retrieval. In addition, this could allow the operation of the device to be changed such that the suture does not need to be pulled completely out of the body through the second cannula, but could simply be captured, and then the whole device removed, pulling the suture through the tissue directly. This should allow the magnetic U-stitch suturing device to be used to place multiple sutures with a single device.

In addition, the magnet-assisted suture grasper described herein could be integrated as end-of-arm tooling for robot-assisted surgery or into the end of an endoscope for direct manipulation of a suture with the endoscope.

Although the magnet-assisted suture grasper is described for grasping a magnetic suture, the magnet-assisted suture grasper also can be used for grasping sutures that include ferromagnetic elements that are attracted by magnets without necessarily including a suture magnet.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

CLAUSES

1. A magnet-assisted suture grasper for grasping a magnetic suture comprising:
   (a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis;
   (b) a retriever body disposed within the needle lumen and translatable therein along the needle body axis;
   (c) a grasper wire having a proximal end and a distal end and being fixedly disposed within the retriever body;
   (d) a grasper arm comprising a proximal end, a proximal-to-intermediate portion, a distal portion, and a distal end, the grasper arm extending from the distal end of the grasper wire and being reversibly moveable between a first position and a second position; and
   (e) a grasper magnet being disposed adjacent the proximal-to-intermediate portion of the grasper arm, the magnet-assisted suture grasper sequestering the grasper magnet within the needle lumen when the grasper arm is in the first position and exposing the grasper magnet from the needle lumen when the grasper arm is in the second position, wherein:
   the distal end of the grasper arm extends further distally than the grasper magnet,
   translation of the retriever body within the needle lumen in a first direction along the needle body axis causes the grasper arm to move from the first position to the second position, thereby exposing the grasper magnet and allowing contact between the grasper magnet and a magnetic suture attracted thereto, and
   translation of the retriever body within the needle lumen in a second direction opposite the first direction along the needle body axis causes the grasper arm to move from the second position to the first position, thereby sequestering the grasper magnet and grasping the magnetic suture within the needle lumen.

2. The magnet-assisted suture grasper according to clause 1, wherein the suture retrieval needle is a hypodermic needle.

3. The magnet-assisted suture grasper according to clause 1 or 2, wherein the suture retrieval needle is straight, the needle body axis thereby being straight.

4. The magnet-assisted suture grasper according to clause 1 or 2, wherein the suture retrieval needle is curved, the needle body axis thereby being curved.

5. The magnet-assisted suture grasper according to any one of clauses 1 to 4, wherein the suture retrieval needle has a sharp tip.

6. The magnet-assisted suture grasper according to any one of clauses 1 to 5, wherein the suture retrieval needle further comprises a hub.

7. The magnet-assisted suture grasper according to any one of clauses 1 to 6, wherein the retriever body and the grasper wire are more flexible than the needle body.

8. The magnet-assisted suture grasper according to any one of clauses 1 to 7, wherein:
the retriever body comprises a proximal end, a distal end, and a retriever tube extending therebetween, the retriever tube defining a retriever tube axis between the proximal and distal ends of the retriever body, the retriever tube having a proximal hole, a distal hole, and a retriever tube lumen extending therebetween along the retriever tube axis; and
the proximal hole of the retriever tube is in fluid communication with the distal hole of the needle body through the retriever tube lumen and the needle lumen.

9. The magnet-assisted suture grasper according to any one of clauses 1 to 8, wherein the grasper arm is integral to the grasper wire.

10. The magnet-assisted suture grasper according to any one of clauses 1 to 9, further comprising a magnet wire having a proximal end and a distal end, wherein the proximal end of the magnet wire is fixedly disposed within the retriever body and the grasper magnet is fixedly attached to the distal end of the magnet wire, either directly or indirectly.

11. The magnet-assisted suture grasper according to clause 10, wherein the magnet wire further comprises a magnet wire distal terminus at the distal end of the magnet wire, the magnet-assisted suture grasper further comprises a ferrule attached to the magnet wire distal terminus, and the grasper magnet is attached to the ferrule.

12. The magnet-assisted suture grasper according to any one of clauses 1 to 9, wherein the grasper magnet is fixedly attached to the grasper arm, either directly or indirectly.

13. The magnet-assisted suture grasper according to any one of clauses 1 to 9, wherein the grasper magnet is fixedly attached to the grasper wire, either directly or indirectly.

14. The magnet-assisted suture grasper according to any one of clauses 1 to 13, wherein:
the grasper arm further comprises an enlarged distal terminus at the distal end of the grasper arm;
the grasper arm is reversibly moveable between the first position and the second position based on translation of the grasper arm from inside of the needle lumen to outside of the needle lumen through the distal hole of the needle body; and
the enlarged distal terminus at the distal end of the grasper arm has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

15. The magnet-assisted suture grasper according to any one of clauses 1 to 13, wherein:
the grasper wire is a first grasper wire;
the grasper arm is a first grasper arm;
the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position;
the first grasper arm further comprises an enlarged distal terminus at the distal end of the first grasper arm;
the second grasper arm further comprises an enlarged distal terminus at the distal end of the second grasper arm;
the first and second grasper arms are reversibly moveable between the first position and the second position based on translation of the first and second grasper arms from inside of the needle lumen to outside of the needle lumen through the distal hole of the needle body; and
the enlarged distal termini of the first and second grasper arms have sizes sufficiently small to allow contact between the grasper magnet and a suture magnet of a magnetic suture attracted thereto when the first and second grasper arms are in the second position and to allow a suture of the magnetic suture to pass when the first and second grasper arms are in the first position, and sufficiently large to block the suture magnet of the magnetic suture from exiting the needle lumen through the distal hole of the needle body when the first and second grasper arms are in the first position.

16. The magnet-assisted suture grasper according to clause 15, further comprising at least one additional grasper wire and at least one additional grasper arm extending distally from the at least one additional grasper wire.

17. The magnet-assisted suture grasper according to any one of clauses 1 to 13, wherein:
the grasper wire is a first grasper wire;
the grasper arm is a first grasper arm;
the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position;
the first and second grasper arms are connected at their distal ends, thereby forming a grasper arm loop;
the grasper arm loop is reversibly moveable between the first position and the second position based on translation of the grasper arm loop from inside of the needle lumen to outside of the needle lumen through the distal hole of the needle body;
the grasper arm loop circumscribes an area sufficiently large to allow contact between the grasper magnet and a suture magnet of a magnetic suture attracted thereto when the grasper arm loop is in the second position; and
the grasper arm loop has a thickness sufficiently great to block the suture magnet of the magnetic suture from exiting the needle lumen through the distal hole of the suture retrieval needle when the grasper arm loop is in the first position.

18. The magnet-assisted suture grasper according to any one of clauses 1 to 13, wherein:
   the grasper wire is a first grasper wire;
   the grasper arm is a first grasper arm;
   the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position;
   the first and second grasper arms are connected at their distal ends, thereby forming a grasper arm loop;
   the first and second grasper arms further comprise an enlarged distal terminus at the distal ends of the first and second grasper arms;
   the grasper arm loop is reversibly moveable between the first position and the second position based on translation of the grasper arm loop from inside of the needle lumen to outside of the needle lumen through the distal hole of the needle body;
   the grasper arm loop circumscribes an area sufficiently large, and the enlarged distal terminus at the distal ends of the first and second grasper arms has a size sufficiently small, to allow contact between the grasper magnet and a suture magnet of a magnetic suture attracted thereto when the grasper arm loop is in the second position;
   the enlarged distal terminus at the distal ends of the first and second grasper arms has a size sufficiently small to allow a suture of the magnetic suture to pass when the grasper arm loop is in the first position; and
   the enlarged distal terminus at the distal ends of the first and second grasper arms has a size sufficiently large to block the suture magnet of the magnetic suture from exiting the needle lumen through the distal hole of the needle body when the grasper arm loop is in the first position.

19. The magnet-assisted suture grasper according to any one of clauses 1 to 13, wherein:
   the grasper wire is a first grasper wire;
   the grasper arm is a first grasper arm;
   the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position;
   the first and second grasper arms are connected at their distal ends, thereby forming a grasper arm loop;
   the grasper arm loop is reversibly moveable between the first position and the second position based on translation of the grasper arm loop from inside of the needle lumen to outside of the needle lumen through the distal hole of the needle body;
   the grasper arm loop is in an elastically deformed closed state when the grasper arm loop is in the first position;
   the grasper arm loop reversibly expands to an open state when the grasper arm loop is in the second position;
   the grasper arm loop circumscribes an area sufficiently large to allow contact between the grasper magnet and a suture magnet of a magnetic suture attracted thereto when the grasper arm loop is in the second position; and
   the grasper arm loop snares the suture magnet of the magnetic suture to block the suture magnet from exiting the needle lumen through the distal hole of the suture retrieval needle when the grasper arm loop is in the first position.

20. The magnet-assisted suture grasper according to clause 19, wherein the grasper arm loop is formed of a shape memory alloy.

21. The magnet-assisted suture grasper according to any one of clauses 1 to 13, wherein:
   the grasper wire is a first grasper wire;
   the grasper arm is a first grasper arm;
   the magnet-assisted suture grasper further comprises: (a) a second grasper wire having a proximal end and a distal end and being fixedly disposed within the retriever body; and (b) a second grasper arm comprising a proximal end, a proximal-to-intermediate portion, a distal portion, and a distal end, the second grasper arm extending from the distal end of the second grasper wire and being reversibly moveable between the first position and the second position;
   the first and second grasper arms comprise curved portions adjacent their distal ends;
   the first and second grasper arms are reversibly moveable between the first position and the second position based on translation of the first and second grasper arms from inside of the needle lumen to outside of the needle lumen through the distal hole of the needle body;
   the proximal-to-intermediate portions of the first and second grasper arms are substantially parallel to the needle body axis and the curved portions adjacent the distal ends of the first and second grasper arms curve inwardly toward the needle body axis when the first and second grasper arms are in the first position;
   at least one of the first or second grasper arms pivots reversibly outwardly from the needle body axis sufficiently far to allow contact between the grasper magnet and a magnetic suture attracted thereto when the first and second grasper arms are in the second position; and
   the curved portions adjacent the distal ends of the two grasper arms contact the magnetic suture to block the magnetic suture from exiting the needle lumen through the distal hole of the suture retrieval needle when the first and second grasper arms are in the first position.

22. The magnet-assisted suture grasper according to any one of clauses 1 to 21, further comprising a lock mechanism that can be reversibly engaged to prevent translation of the retriever body within the needle lumen in the first direction and/or the second direction.

23. The magnet-assisted suture grasper according to clause 22, wherein the lock mechanism can be reversibly engaged in a first setting that prevents translation of the retriever body within the needle lumen when the distal end of the grasper arm is inside the needle lumen and reversibly engaged in a second setting that prevents translation of the retriever body within the needle lumen when the grasper magnet is outside of the needle lumen.

24. The magnet-assisted suture grasper according to clause 23, wherein maintaining the lock mechanism in the first setting or the second setting does not require energy input.

25. A system for passing a magnetic suture comprising:
the magnet-assisted suture grasper of any one of clauses 1-24; and
a magnetic suture comprising a suture magnet and a suture extending from the suture magnet.

26. A system for passing a magnetic suture comprising:
the magnet-assisted suture grasper of any one of clauses 1-24; and
a magnetic suture loop comprising a suture magnet and a bifurcated suture extending from the suture magnet and forming a suture loop.

27. The system according to clause 26, further comprising a cartridge tube, wherein:
the cartridge tube comprises a cartridge tube proximal opening, a cartridge tube distal opening, and a cartridge tube lumen therebetween;
the suture loop traverses the cartridge tube lumen based on having been inserted through the cartridge tube distal opening; and
the suture magnet is disposed outside of the cartridge tube lumen adjacent the cartridge tube distal opening.

What is claimed is:

1. A magnetic suture loop comprising a suture magnet, a bifurcated suture, and a cartridge tube, wherein:
the bifurcated suture extends from the suture magnet and forms a suture loop;
the cartridge tube comprises a cartridge tube proximal end, a cartridge tube distal end, and a cartridge tube wall extending therebetween;
the cartridge tube has a cartridge tube proximal opening at the cartridge tube proximal end, a cartridge tube distal opening at the cartridge tube distal end, and a cartridge tube lumen extending from the cartridge tube proximal opening to the cartridge tube distal opening;
the suture loop traverses the cartridge tube lumen based on having been inserted through the cartridge tube distal opening; and
the suture magnet is disposed outside of the cartridge tube lumen adjacent the cartridge tube distal opening.

2. The magnetic suture loop according to claim 1, wherein the suture magnet is a dipole magnet.

3. The magnetic suture loop according to claim 1, wherein the bifurcated suture has a tensile strength of at least 0.96 kgf.

4. The magnetic suture loop according to claim 3, wherein the bifurcated suture has a tensile strength of 1.5 to 2.0 kgf.

5. The magnetic suture loop according to claim 1, wherein the bifurcated suture has a mean diameter of at least the mean diameter of a 7-0 suture.

6. The magnetic suture loop according to claim 5, wherein the bifurcated suture is one or more of a 7-0 suture, a 3-0 suture, a 2-0 suture, or a 0 suture.

7. The magnetic suture loop according to claim 1, wherein the bifurcated suture further comprises a ferrule comprising (i) a tapered region in which the bifurcated suture is secured and (ii) a straight region in which the suture magnet is provided.

8. The magnetic suture loop according to claim 1, wherein the cartridge tube lumen is sized such that the suture loop of the bifurcated suture is free to enter the cartridge tube lumen but the suture magnet cannot enter the cartridge tube lumen, thereby allowing the suture loop of the bifurcated suture to freely pass through the cartridge tube lumen in one direction but to be captured in the opposite direction.

9. The magnetic suture loop according to claim 1, wherein the cartridge tube wall has a wall thickness and a modulus providing the cartridge tube with a greater column strength than the suture loop of the bifurcated suture.

10. The magnetic suture loop according to claim 1, wherein the cartridge tube distal end is straight.

11. The magnetic suture loop according to claim 1, wherein the cartridge tube distal end is curved.

\* \* \* \* \*